US009345745B2

(12) United States Patent
Wang et al.

(10) Patent No.: US 9,345,745 B2
(45) Date of Patent: May 24, 2016

(54) METHODS FOR TREATING INFLAMMATORY DISORDERS AND TRAUMATIC BRAIN INJURY USING STABILIZED NON-HEMATOPOIETIC EPO SHORT PEPTIDES

(76) Inventors: Bo Wang, Fort Lee, NJ (US); Rui Rong Yuan, Fort Lee, NJ (US); Wei Lu, Harrison, NJ (US); Peter C. Dowling, Fort Lee, NJ (US)

( * ) Notice: Subject to any disclaimer, the term of this patent is extended or adjusted under 35 U.S.C. 154(b) by 168 days.

(21) Appl. No.: 13/073,275

(22) Filed: Mar. 28, 2011

(65) Prior Publication Data

US 2011/0190217 A1     Aug. 4, 2011

Related U.S. Application Data

(63) Continuation-in-part of application No. 11/913,038, filed as application No. PCT/IB2006/003581 on May 1, 2006, now Pat. No. 8,653,028.

(60) Provisional application No. 61/319,008, filed on Mar. 30, 2010, provisional application No. 60/676,592, filed on Apr. 29, 2005.

(51) Int. Cl.
A61K 38/18       (2006.01)
C07K 14/505    (2006.01)
A61K 38/12       (2006.01)

(52) U.S. Cl.
CPC ............. *A61K 38/12* (2013.01); *A61K 38/1808* (2013.01); *C07K 14/505* (2013.01)

(58) Field of Classification Search
None
See application file for complete search history.

(56) References Cited

U.S. PATENT DOCUMENTS

| | | | |
|---|---|---|---|
| 4,105,027 A | 8/1978 | Lundquist | |
| 4,192,309 A | 3/1980 | Poulsen | |
| 4,227,522 A | 10/1980 | Carris | |
| 4,627,432 A | 12/1986 | Newell et al. | |
| 4,778,054 A | 10/1988 | Newell et al. | |
| 4,811,731 A | 3/1989 | Newell et al. | |
| 5,035,237 A | 7/1991 | Newell et al. | |
| 5,986,047 A | 11/1999 | Wrighton et al. | |
| 6,531,121 B2 | 3/2003 | Brines et al. | |
| 6,831,060 B2 | 12/2004 | DeSauvage et al. | |
| 6,849,602 B1 | 2/2005 | O' Brien | |
| 6,921,527 B2 | 7/2005 | Platz et al. | |
| 7,211,253 B1 | 5/2007 | Way | |
| 7,410,941 B1 | 8/2008 | Brines et al. | |
| 2004/0171123 A1 | 9/2004 | Rosen et al. | |
| 2009/0221482 A1* | 9/2009 | Cerami et al. | 514/12 |
| 2009/0258821 A1* | 10/2009 | Cerami et al. | 514/8 |
| 2011/0263504 A1* | 10/2011 | Cerami | C07K 14/505 514/15.4 |

FOREIGN PATENT DOCUMENTS

| | | |
|---|---|---|
| WO | 91 16038 A1 | 10/1991 |
| WO | 2004 108667 A2 | 12/2004 |

OTHER PUBLICATIONS

Wells, J.A. Additivity of Mutational Effects in Proteins. Biochemistry, vol. 29, No. 37, pp. 8509-8517 (Sep. 18, 1990).*
Ngo et al. Computational Complexity, Protein Structure Prediction and the Levinthal Paradox. The Protein Folding Problem and Tertiary Structure Prediction, pp. 433-440 and 492-495 (1994).*
Kirsch et al. EMBO J. BMP-2 antagonists emerge from alterations in the low affinity binding epitope for receptor BMPR-II. vol. 19(13):3314-3324 (2000).*
Farooq et al. The in vivo and in vitro induction of anterior chamber associated immune deviation to myelin antigens in C57BL/6 mice. Brain, Behavior, and Immunity 42:118-122 (2014).*
Habek et al. Pathology of Acute Disseminated Encephalomyelitis. Translational Neuroscience 2(3) 252-255 (2011).*
Brines, et al., Erythropoietin crosses the blood-brain barrier to protect against experimental brain injury, Proc. Nat'l. Acad. Sci. USA 97, pp. 10526-10531 (2000).
Siren et al., Erythropoietin—a novel concept for neuroprotection, Eur. Arch. Psychiatry Clin. Neurosci. 251, pp. 179-184 (2001).
Buemi et al., The Pleiotropic Effects of Erythropoietin in the Central Nervous System, Neuropathol. Ex. Neurol. 62, pp. 228-236 (2003).
Li et al., Beneficial Effect of Erythropoietin on Experimental Allergic Encephalomyelitis, Ann. Neurol. 56. pp. 767-777 (2004).
Sakanaka et al., In vivo evidence that erythropoietin protects neurons from ischemic damage, Proc. Nat'l Acad. Sci. USA 95 pp. 4635-4640 (1988).
Tsai et al., A Critical Role of Erythropoietin Receptor in Neurogenesis and Post-Stroke Recovery, J. Neurosci. 26, pp. 1269-1274 (2006).
Buemi et al., Erythropoietin and the brain: from neurodevelopment to neuroprotection, Clin. Sci (Lond.) 103, pp. 275-282 (2002).
Erbayraktar et al., Asialoerythropoietin is a nonerythropoietic cytokine with broad neuroprotective activity in vivo, Proc. Nat'l. Acad. Sci. USA 100, pp. 6741-6746 (2003).
Leist et al., Derivatives of Erythropoietin that are Tissue Protective But Not Erythropoietic, Science 305, pp. 239-242 (2004).
Mun, et al., Impaired Biological Activity of Erythropoietin Cyanate Carbamylation, Blood Purif. 18, pp. 13-17 )2000).
Brines, et al., Erythropoietin mediates tissue protectioh through an erythropoietin and common Beta-subunit heterorecptor, Proc. Nat'l. Acad. Sci. USA 101, 14907-12 (2004).
Campana et al., Identification of a neurotrophic sequence in erythropoietin, Int'l J. Mol. Med. 1, pp. 235-241 (1998).
Watowich et al., Activation and Inhibition of Erythropoietin Receptor Function: Role of Receptor Dimerization, Mol. Cell Biol. 14, 3535-49 (1994).
Livnha, et al., Functional Mimicry of a Protein Hormone by a Peptide Agonist: The ERO Receptor Complex at 2.8 Angstroms, Science 273, pp. 464-471 (1996).

(Continued)

*Primary Examiner* — Elizabeth C Kemmerer
*Assistant Examiner* — Regina M Deberry
(74) *Attorney, Agent, or Firm* — Bryan D. Zerhusen; Locke Lord LLP

(57) ABSTRACT

The described invention provides methods for treating an inflammatory brain disease, disorder or condition and for treating a traumatic brain injury having an inflammatory component in a subject in need thereof using isolated erythropoietin (EPO)-derived oligopeptides.

13 Claims, 13 Drawing Sheets

(56) References Cited

OTHER PUBLICATIONS

Wrighton, et al., Small Peptides as Potent Mimetics of the Protein Hormone Erythropoietin, Science 273, pp. 458-463 (1996).
Wen, Erythropoietin Structure-Function Realtionships, J. Biol. Chem. 269, pp. 22839-22846 (1994).
Trapp, et al., Pathogenesis of tissue injury in MS lesions, J. Neuroimmunol. 98. pp. 49-56 (1999).
Bettelli et al., Myelin Oligodendrocyte Glycoprotein-specific T Cell Receptor Transgenic Mice Development Spotaneious Autoimmune Optic Neuritis, J. Exp. Med. 197, pp. 1073-1081 (2003).
Crawford et al., High prevalance of autoreactive, neuroantigen-specific CD8+ T cells in multiple sclerosis revealed by novel flow cytometric assay, Blood 103(11), pp. 4222-4231 (2004).
Abdul-Majid, et al., Comparing the pathogenesis of experimental autoimmune encephalomyelitis in CD4-/- and CD8-/- DBA/1 mice defines qualitative roles of different T cell subsets, J. Neuroimmunol. 141, pp. 10-19 (2003).
Battistini et al., CD8+ T cells from patients with acute multiple sclerosis display selective increase of adhesiveness in brain venules: a critical role for P-selectin glycoprotein ligand-1, Blood 101, pp. 2775-2782 (2003).
Ghosh et al., Transdermal & Tropical Drug Delivery Systems 249-97 (1997).
Tuohy et al., Identification of an Encephalitogenic Determinant of Myelin Proteolipid Protein for SJL Mice, J. Immunol. 142, pp. 1523-1527 (1989).
Bebo et al., Low-Dose Estrogen Therapy Ameliorates Experimental Autoimmune Encephalomyelitis in Two Different Inbred Mouse Strains, J. Immunol. 166, pp. 2080-2089 (2001).
Yoshimura et al., Chronic Experimental Allergic Encephalomyelitis in Guinea Pigs Induced by Proteolipid Protein, J. Neurol. Sci. 69, pp. 47-58 (1985).
Sobel et al., The Immunopathology of Chronic Experimental Allergic Encephalomyelitis Induced in Rabbits with Bovine Proteolipid Protein, J. Immunol. 136, pp. 157-163 (1986).
Bernard et al., Myelin oligodendrite glycoprotein: a novel candidate authoantigen in multiple sclerosis, J. Mol. Med. 75, pp. 77-88 (1997).
Brines, et al., Emerging biological roles for erythropoietin in the nervous system, Nature Reviews (Neuroscience) 6, pp. 484-494 (2005).
Schindler et al., Transcriptional Responses to Polypeptide Ligands: The JAK STAT Pathway, Ann. Rev. Biochem. 64, pp. 621-651 (1995).
McColl, et al., Extension of cerebral hypoperfusion and ischaemic pathology beyond MCA territory after intraluminal filament occlusion in C57Bl/6J mice, Brain Res. 997, pp. 14-22 (2004).
Belayev et al., Milddle cerebral artery occlusion in the mouse by intraluminal suture coated with poly-L-lysine: neurological and histological validation, Brain Res. 8933, pp. 181-190 (1999).
Engesser-Cesar et al., Voluntary Wheel Running Improves Recovery from a Moderate Spinal Cord Injury, J. Neurotrama 22, pp. 151-171 (2005).
Scheff, et al., Experimental Modeling of Spinal Cord Injury: Characterization of a Force-Defined Injury Device, J. Neurotrama 20, pp. 179-193 (2003).

\* cited by examiner

METHODS FOR TREATING INFLAMMATORY DISORDERS AND TRAUMATIC BRAIN INJURY USING STABILIZED NON-HEMATOPOIETIC EPO SHORT PEPTIDES

CROSS-REFERENCE TO RELATED APPLICATIONS

This application claims priority from U.S. Provisional Application No. 61/319,008, filed Mar. 30, 2010, and is a continuation-in-part of U.S. application Ser. No. 11/913,038, entitled "Erythropoietin-Derived Short Peptide and Its Mimics as Immunoinflammatory Modulators, filed Aug. 18, 2008 now U.S. Pat. No. 8,653,028, which is the national phase of PCT/IB2006/003581 filed May 1, 2006, which claims priority from U.S. provisional application No. 60/676,592, filed Apr. 29, 2005, each of which is incorporated herein by reference.

FIELD OF USE

The invention relates to peptides useful for treating inflammatory brain disorders, including, but not limited to, traumatic brain injury.

BACKGROUND

1. Traumatic Brain Injury

Traumatic brain injury (TBI) is caused by a head injury that can result in lasting damage to the brain and affects up to 10 million patients worldwide each year. The health effects of TBI can be debilitating, result in long term disability, and have significant financial burdens.

Traumatic brain injury is caused by an external mechanical force, such as a blow to the head, concussive forces, acceleration-deceleration forces, or a projectile. It may occur both when the skull fractures and the brain is directly penetrated (open head injury) and also when the skull remains intact but the brain still sustains damage (closed head injury).

Symptoms of a TBI range in severity, depending on the extent of damage to the brain, and may include headaches, neck pain, confusion, difficulty remembering, concentrating, or making decisions, dizziness, fatigue, mood changes, nausea, irritability, photophobia, blurred vision, ringing in the ears, loss of sense of taste or smell, seizures, sleep disturbances, hypoxemia, hypotension and brain swelling, muscle weakness, paralysis, coma, and a progressive decline in neurologic function following the traumatic brain injury.

TBI is graded as mild (meaning a brief change in mental status or consciousness), moderate, or severe (meaning an extended period of unconsciousness or amnesia after the injury) on the basis of the level of consciousness or Glasgow coma scale (GCS) score after resuscitation. The GCS scores eye opening (spontaneous=4, to speech=3, to pain=3, none=1), motor response (obeys=6, localizes=5, withdraws=4, abnormal flexion=3, extensor response=2, none=1), and verbal response (oriented=5, confused=4, inappropriate=3, incomprehensible=2, none=1). Mild TBI (GCS 13-15) is in most cases a concussion and there is full neurological recovery, although many of these patients have short-term memory and concentration difficulties. In moderate TBI (GCS 9-13) the patient is lethargic or stuporous, and in severe injury (GCS 3-8) the patient is comatose, unable to open his or her eyes or follow commands.

Patients with severe TBI (comatose) have a significant risk of hypotension, hypoxaemia, and brain swelling. If these sequalae are not prevented or treated properly, they can exacerbate brain damage and increase the risk of death.

The term "traumatic intracerebral hemorrhage" as used herein refers to such bleeding that is caused, caused by, or associated with traumatic injury. Intracerebral hemorrhages commonly occur in the basal ganglia, thalamus, brain stem (predominantly the pons), cerebral hemispheres, and the cerebellum. Extension into the ventricles occurs in association with deep, large hematomas. Edematous parenchyma, often discolored by degradation products of hemoglobin, is visible adjacent to the clot. Histologic sections are characterized by the presence of edema, neuronal damage, macrophages, and neutrophils in the region surrounding the hematoma. The hemorrhage spreads between planes of white-matter cleavage, causing some destruction of the brain structure, and leaving intact neural tissue within and surrounding the hematoma.

Intraparenchymal bleeding results from the rupture of the small penetrating arterioles that originate from basilar arteries or from the anterior, middle, or posterior cerebral arteries. Degenerative changes in the arteriolar walls by chronic hypertension reduce compliance, weaken the wall, and increase the likelihood of spontaneous rupture. Studies suggest that most bleeding occurs at or near the bifurcation of affected arteries, where prominent degeneration of the tunica media and smooth muscles can be seen.

Neurological damage after TBI does not all occur immediately at the moment of impact (primary injury), but instead evolves afterwards (secondary injury). Secondary brain injury is the leading cause of in-hospital deaths after TBI. Most secondary brain injury is caused by brain swelling, with an increase in intracranial pressure and a subsequent decrease in cerebral perfusion leading to ischemia. Within hours of TBI, due to a breakdown of tight endothelial junctions which make up the blood-brain barrier (BBB), normally excluded intravascular proteins and fluid penetrate into cerebral parenchymal extracellular space (vasogenic edema). Once plasma constituents cross the BBB, the edema spreads. The vasogenic fluid accumulating in brain causes cerebral edema, raises intracranial pressure, and lowers the threshold of systemic blood pressure for cerebral ischemia. A reduction in cerebral blood flow or oxygenation below a threshold value or increased intracranial pressure leading to cerebral herniation increases brain damage and morbidity.

Approximately 10% of TBIs (1,400,000 annual U.S. cases) are complicated by intracerebral hemorrhage requiring surgery. The delay in the breakdown of the blood-brain barrier and the development of cerebral edema after an intracerebral hemorrhage (ICH) suggest that there may be secondary mediators of both neural injury and edema. It generally is believed that blood and plasma products mediate most secondary processes that are initiated after an ICH.

Several pharmacological agents, such as free-radical scavengers, antagonists of N-methyl-D-aspartate, and calcium-channel blockers, have been studied in attempt to prevent the secondary injury associated with TBI, but none has proven effective.

Hypoxemia and hypotension commonly occur before the patient reaches a hospital and significantly increase the risk of secondary brain injury and the likelihood of a poor outcome. Studies have reported that in children with TBI, 13% had a documented hypoxemic (meaning having a decreased partial pressure of oxygen in the blood) episode and 6% had hypercapnia (meaning the condition of having an abnormally high level of carbon dioxide in the circulating blood). Various studies have reported that 27% to 55% of patients with TBI were hypoxemic (meaning causing hemoglobin oxygen saturation less than 90%) at the scene, in the ambulance, or on arrival at the emergency department. Intubation at the scene of the accident or in the emergency department was required for all patients if the GCS score was 3-5, 73% if the GCS was 6-7, and 62% if the GCS was 8-9.

In adults, hypotension is defined as a single measurement of a systolic blood pressure below 90 mm Hg. Some studies have reported that hypotensive episodes were observed in 16% and 32% of patients with severe TBI at the time of hospital arrival and during surgical procedures, respectively. A single episode of hypotension was associated with increased morbidity and doubling of mortality. In children, a low systolic blood pressure, sustained for at least 5 minutes, is associated with a poor outcome.

2. Erythropoietin

Erythropoietin (hEPO), a 165 amino acid glycoprotein hormone, is the principal hormone involved in the regulation and maintenance of a physiological level of circulating erythrocyte mass. It is produced primarily by the kidney in the adult and by the liver during fetal life; and is maintained in the circulation at a concentration of about 15 mU/ml to about 20 mU/ml of serum, or about 0.01 nM under normal physiological conditions. EPO has been used extensively for the treatment of anemia in humans.

The hematopoietic effect of EPO is mediated by binding and inducing dimerization of two molecules of the EPO receptor (EpoR) on the cell surface [Watowich, S. S., et al., Mol Cell Biol, 14: 3535-49 (1994)]. The EpoR belongs to a cytokine receptor superfamily that is also related to the cytokines granulocyte colony-stimulating factor (G-CSF), granulocyte macrophage colony-stimulating factor (GM-CSF), interleukins 2-7 and ciliary neurotrophic factor (CNTF). The signaling pathway involves the autophosphorylation and activation of the Janus family protein tyrosine kinase, JAK-2, which further activates additional signaling proteins including STATS, Ras-mitogen-activated protein kinase (MAPK) and phosphatidylinositol 3-kinase (PI3K). Studies on structure activity relationships of EPO have identified regions and amino acids essential for binding to the erythropoietin receptor (EpoR) [Livnah, O., et al., Science, 273: 464-71 (1996); Wrighton, N. C., et al., Science, 273: 458-64 (1996); Wen, D., J Biol Chem, 269: 22839-46 (1994)].

In addition to its hematopoietic effects, studies have reported that EPO may have broad neuroprotective capabilities following CNS injury. [Brines, M. L., et al., Proc Natl Acad Sci USA, 97: 10526-31 (2000); Siren, A. L. and Ehrenreich, H., Eur Arch Psychiatry Clin Neurosci, 251: 179-84 (2001); Buemi, M., et al., J. Neuropathol Exp Neurol, 62: 228-36 (2003); Li, W., et al., Ann Neurol, 56: 767-77 (2004); Sakanaka, M., et al., Proc Natl Acad Sci USA, 95: 4635-40 (1998)]. Therapeutic effects of exogenously administered EPO on several diverse forms of neurologic injury, including occlusive cerebral vascular disease, acute brain trauma, epilepsy, and an autoimmune model of demyelinating disease, experimental autoimmune encephalomyelitis (EAE), have been tested and the degree of neurologic impairment was significantly reduced [Brines, M. L. et al., Proc Natl Acad Sci USA, 97: 10526-31 (2000); Li, W. et al., Ann Neurol, 56: 767-77 (2004); Tsai, P. T., et al., J Neurosci, 26: 1269-74 (2006); Buemi, M., et al., Clin Sci (Loud), 103: 275-82 (2002)]. Studies in which recombinant EPO and EPO mutants have been tested for their biological effects in a variety of animal models have suggested that the neuroprotection mediated by EPO might not occur through a conventional interaction between EPO and classic EpoR. The common β receptor (βcR) or CD131, which is also an important component for other ligands including IL-3, IL-5 and GM-CSF, has been proposed to be a key subunit associated with the EpoR that is responsible for EPO mediated non-hematopoietic effects. Additional unknown receptor(s) also may play critical roles in the non-hematopoietic effects induced by chemically modified or mutant EPO.

Long-term EPO therapy remains significantly limited in non-anemic patients with neurological injury because EPO treatment may overly stimulate erythropoiesis. To overcome this concern, EPO therapy would have to be limited to very short term use. Other EPO molecular preparations, such as an asialo-form of EPO, carbamylated EPO (CEPO), or certain EPO mutants, have been shown to be neuroprotective in animals following experimental traumatic spinal cord injury or acute stroke without provoking an increase in red blood cell mass [Erbayraktar, S., et al., Proc Natl Acad Sci USA, 100: 6741-46 (2003); Leist, M., et al., Science, 305: 239-42 (2004); Mun, K. C. and Golper, T. A. Blood Purif, 18: 13-17 (2000); Brines, M., et al., Proc Natl Acad Sci USA, 101: 14907-12 (2004)]. A short 17 amino acid EPO-derived linear peptide also was reported to have neuroprotective effects in cell culture, but its in vivo biologic effects were not certain [Campana, W. M., et al., Int'l J Mol Med, 1: 235-41 (1998)]. Taken all together, the evidence suggests that specific functional and structural domains may co-exist within the full 165 amino acid EPO molecule.

U.S. Published Application No. 2009/0029906, which is incorporated by reference herein in its entirety, describes a library of stabilized isolated small EPO-derived peptides comprising about 7 to about 25 amino acids in length that are highly protective in mouse models of EAE, acute stroke, and brain injury as well as arthritis and reverse and/or reduce manifestations of the associated disease. This protection was maintained during long term observation in EAE mice and was not associated with hematological side effects. The short peptides protect against tissue damage by modulating the immune-mediated inflammatory network, i.e. by reducing major histocompatibility complex (MHC) class I and class II over-expression; by reducing inflammatory cytokines; and by suppressing antigen-specific T cell function in peripheral lymphoid tissue and brain tissue as well as in in vitro tissue culture assays. Moreover, addition of a small bicyclic compound, such as d-biotin, to the N- or C-terminal of the short EPO linear peptides, increased the stability of these peptides without hampering their biologic activity.

3. Immunomodulations

Lymphocytes are the cells that determine in part the specificity of immunity. Cells that interact with lymphocytes, including monocytes/macrophages, dendritic cells (an antigen-presenting immune cell that initiates the immune response by activating lymphocytes and stimulating the secretion of cytokines and that prevents autoimmune reactions by instructing the T lymphocytes to be silent or tolerant to the body itself), Langerhans' cells (dendritic cells in the epidermis), natural killer (NK) cells (a type of cytotoxic lymphocyte that kill by releasing small cytoplasmic granules of proteins called perform and granzyme that cause the target cell to die by apoptosis), mast cells (long lived resident cells of several types of tissues that when activated release characteristic immune mediators, in part through Fc epsilon receptor (FceRI), the high affinity IgE receptor, expressed on the mast cell surface), granules and various hormonal mediators, basophils (a small population of short-lived, terminally differentiated circulating granulocyte leukocytes containing cytoplasmic granules that stain with basophilic dyes that can infiltrate tissues and are major sources of histamine (a vasodilator) and other potent chemical mediators of inflammation, constitutively express FceRI, express a variety of seven membrane transverse receptors that bind chemotactic factors, and in humans, express several cytokine receptors); and other members of the myeloid lineage of cells, play critical parts in the presentation of antigen and in the mediation of immune functions.

The cells of the immune system are found in peripheral organized tissues, such as the spleen, lymph nodes, Peyer's patches of the intestine, and tonsils. Lymphocytes also are found in the central lymphoid organs, the thymus and bone marrow. A substantial portion of the lymphocytes and macrophages comprise a recirculating pool of cells found in the blood and lymph.

Two broad classes of lymphocytes are recognized: the B-lymphocytes, or B-cells, which are precursors of antibody-secreting cells, and the T lymphocytes, or T-cells, which express important regulatory functions. T lymphocytes may be subdivided into two distinct classes based on the cell surface receptors they express: CD4+ cells, and CD8+ cells. The process of positive selection determines whether a T cell ultimately becomes a CD4+ cell or a CD8+ cell. Prior to positive selection, all thymocytes have both co-receptors (CD4+, CD8+); during positive selection these cells are transformed into either CD4+ CD8− T cells or CD8+CD4− T cells depending on whether they recognize MHC II or MHC I, respectively. Subsequent to positive selection, T cells undergo negative selection where developing T cells which recognize self-peptides bound to MHC presented by dendritic cells or macrophages in the thymus are signaled to undergo apoptosis and are deleted from the T cell population.

Most autoreactive T cells are negatively selected and eliminated during thymic development. However, the central selection process often is incomplete and autoreactive lymphocytes with pathogenic potential still circulate in the peripheral lymphoid tissues. These autoreactive T cells may attack self-organs when abnormally activated by self-antigens or mimics leading to development of autoimmune disorders.

T cells expressing CD4 molecules (and not CD8) on their surface usually are specific for antigens presented by MHC II and not antigens presented by MHC class I (i.e., they are MHC class II-restricted). T cells expressing CD8 on their surface are specific for antigens presented by MHC I and usually are MHC class I restricted.

CD4+ T cells commonly are divided into four distinct lineages: conventional T helper (Th) cells (T hp 1 and T hp 2, T hp 17) and Treg cells. Th cells control adaptive immunity by activating, in an antigen-specific fashion, other effector cells, such as CD8+ cytotoxic T cells, B cells and macrophages. T reg cells are T cells that suppress potentially deleterious activities of Th cells including Th17 cells. Many central aspects of Treg cell biology are not known.

Naïve T cells (meaning T cells that have matured and left the thymus where they are generated, but that have not yet encountered antigen) differentiate into at least four functional subsets following stimulation by antigen presented by dendritic cells (dendritic cells are specialized for driving the activation of T cells and are thought to help direct their differentiation by differential secretion of cytokines determining the different subsets). Three subsets—TH1, TH2, and TH17, activate other immune cells, including B cells, NK cells, and inflammatory cells, such as neutrophils and macrophages (which also have noninflammatory functions). Vrisekoop, N. et al., J. Biology 8:91.1-91.6 (2009). Th17 cells, a subset of CD4+ TH cells, produce interleukin 17 and are thought to play a role in inflammation and tissue injury. The fourth subset comprises regulatory T cells (Tregs, which express CD4, CD25, and Foxp3), and they suppress the activation of the other subsets, partly by communicating with dendritic cells. Id. Tregs and Th17 cells therefore usually have antagonistic activities.

4. Neuroinflammatory Responses

Notwithstanding that the blood brain barrier tries to restrict and tightly control peripheral immune access to the CNS, the CNS is capable of dynamic immune and inflammatory responses to a variety of insults, including trauma. The acute neuroinflammatory response includes activation of microglia, appearance of dendritic cells, resident tissue macrophages in the CNS and the principle mediators of neuroinflammation, resulting in phagocytosis and the release of inflammatory mediators such as cytokines and chemokines Chronic neuroinflammation includes long-standing activation of microglia and subsequent sustained release of inflammatory mediators, which works to perpetuate the inflammatory cycle, activating additional microglia, promoting their proliferation, and resulting in further release of inflammatory factors.

Neurodegenerative CNS disorders, including, but not limited to, multiple sclerosis, Alzheimer's disease, Parkinson's disease, Huntington's disease, amyotrophic lateral sclerosis, are associated with chronic neuroinflammation.

5. EAE Animal Model and Multiple Sclerosis

Multiple sclerosis (MS), a disorder of unknown cause, is defined clinically by characteristic symptoms, signs and progression, and is defined pathologically by scattered areas of inflammation and demyelination affecting the brain, optic nerves and spinal cord white matter. It is widely believed that the pathogenesis of MS involves an immune-mediated inflammatory demyelinating process.

Experimental autoimmune encephalomyelitis (EAE) is a central nervous system inflammatory demyelinating disease involving acute injury to the brain and spinal cord white matter. This animal model has been used widely by many investigators to study disease pathogenesis and to explore new therapies for its human counterpart, multiple sclerosis (MS). Pathogenesis of both MS and EAE is believed to involve (1) activation of myelin reactive T cells; (2) upregulated expression of chemokines and adhesion molecules; (3) focal T cells and macrophage infiltration into the CNS white matter; and (4) demyelination and axonal injury and loss of neurological function [Trapp., B. et al., J Neuroimmunol, 98: 49-56 (1999)]. In both EAE and MS, activated T-lymphocytes specific for self-antigens present in myelin are linked to CNS inflammation and to the breakdown of the blood brain barrier to peripheral blood leukocytes and plasma proteins; this is predominantly restricted to myelin rich white matter area of the CNS [Bettelli, E., et al., J Exp Med, 197: 1073-81 (2003); Crawford, M. P., et al., Blood 103(11): 4222-31 (2004); Abdul-Majid, K. B., et al., J Neuroimmunol, 141: 10-19 (2003); Battistini, L., et al., Blood, 101: 4775-82 (2003)].

EAE can be induced experimentally in genetically susceptible animals, such as mice, by immunization with immunodominant peptides from myelin proteins, such as myelin basic protein (MBP), proteolipid protein (PLP), and myelin oligodendrocytes glycoprotein (MOG), emulsified in complete Freund's adjuvant followed by injection of pertussis toxin as an additional adjuvant for certain mouse strains [Li, W., et al., Ann Neurol, 56: 767-77 (2004)]. Disease development is variable from strain to strain. For example, in SJL/J mice, PLP or MBP induces a relapsing-remitting progression, whereas C57BL/6 mice immunized with MOG often develop a chronic form of disease.

The described invention provides methods for using short stabilized EPO-derived peptides for treating traumatic brain injury that allow for the harnessing of the neuroprotective capabilities of EPO without unacceptable side effects brought about by its hematopoietic effects.

SUMMARY

According to one aspect, the described invention provides a method for treating an inflammatory brain disease, disorder, or condition in a subject, the method comprising: (a) providing a pharmaceutical composition comprising: (i) a therapeutically effective amount of at least one isolated erythropoietin (EPO)-derived oligopeptide; and (ii) a pharmaceutically acceptable carrier; (b) administering the pharmaceutical composition of (a) to the subject; (c) treating at least one symptom of the inflammatory brain disease, disorder or condition; and (d) maintaining red blood cell indices of the subject at substantially normal levels during treatment.

According to one embodiment of the method, the at least one isolated erythropoietin (EPO)-derived oligopeptide is a cyclic peptide. According to another embodiment, the at least one isolated erythropoietin (EPO)-derived oligopeptide is at least one cyclic peptide selected from the group consisting of JM-4 (SEQ ID NO: 1), JM-5 (SEQ ID NO: 9), and JM-7 (SEQ ID NO: 11). According to another embodiment, the at least one isolated erythropoietin (EPO)-derived oligopeptide is JM-4 (SEQ ID NO: 1). According to another embodiment, the at least one isolated erythropoietin (EPO)-derived oligopeptide has at least 90% amino acid sequence identity to JM-4 (SEQ ID NO: 1). According to another embodiment, the at least one isolated erythropoietin (EPO)-derived oligopeptide is a stabilized isolated erythropoietin (EPO)-derived oligopeptide, wherein the stabilized isolated erythropoietin (EPO)-derived oligopeptide comprises at least one small bicyclic compound added to either an N-terminal end or a C-terminal end of the isolated erythropoietin (EPO)-derived oligopeptide. According to another embodiment, the at least one small bicyclic molecule is biotin. According to another embodiment, the inflammatory brain disease is multiple sclerosis. According to another embodiment, the inflammatory brain disease is a demyelinating disease. According to another embodiment, the inflammatory brain disease is a chronic inflammatory brain disease. According to another embodiment, the chronic inflammatory brain disease is a neurodegenerative disease selected from the group consisting of Alzheimer's disease (AD), Parkinson's disease (PD), Huntington's disease, amyotrophic lateral sclerosis (ALS), and age-related macular degeneration (ARMD). According to another embodiment, the inflammatory brain disease, disorder or condition is a complication following a traumatic brain injury (TBI). According to another embodiment, administering step (b) occurs within about 15 minutes after the traumatic brain injury. According to another embodiment, administering step (b) occurs within about 1 hour after the traumatic brain injury. According to another embodiment, administering step (b) occurs within about 3 hours after the traumatic brain injury. According to another embodiment, administering step (b) occurs within about 6 hours after the traumatic brain injury. According to another embodiment, administering step (b) occurs within 9 hours after the traumatic brain injury. According to another embodiment, administering step (b) occurs within about 24 hours of the traumatic brain injury. According to another embodiment, administration of the pharmaceutical composition treats at least one symptom of the traumatic brain injury (TBI) selected from the group consisting of hypotension, hypoxemia, brain swelling, headache, a neck pain, a difficulty remembering, a difficulty concentrating, a difficulty making decisions, fatigue, a mood change, nausea, photophobia, blurred vision, ear ringings, a loss of sense of taste, and a loss of sense of smell, seizures, coma, muscle weakness, paralysis, and a progressive decline in neurologic function following the traumatic brain injury. According to another embodiment, treating step (c) further comprises reducing infiltration of a population of a mononuclear cell into the brain of the subject. According to another embodiment, treating step (c) further comprises reducing axonal damage in at least one region of the brain of the subject affected by the inflammatory disease, disorder or condition. According to another embodiment, treating step (c) further comprises reducing neuronal cell death in at least one region of the brain of the subject affected, directly or indirectly, by the disease, disorder or condition. According to another embodiment, treating step (c) further comprises reducing glial cell death in at least one region of the brain of the subject affected, directly or indirectly, by the disease, disorder or condition. According to another embodiment, treating step (c) further comprises reducing neuronal and glial cell death in at least one region of the brain of the subject affected, directly or indirectly, by the disease, disorder or condition. According to another embodiment, treating step (c) further comprises improving a neurological deficit. According to another embodiment, the therapeutically effective amount is from about 0.000001 mg/kg body weight to about 10 g/kg body weight. According to another embodiment, the red blood cell indices in (d) comprise a hematocrit, and wherein the hematocrit is maintained at a stable level. According to another embodiment, the red blood cell indices in (d) comprise a hematocrit, and wherein the hematocrit is maintained within about 20% of a reference value or baseline level. According to another embodiment, the isolated erythropoietin (EPO)-derived oligopeptide of the pharmaceutical composition, once administered, contacts at least one cell population that does not express erythropoietin receptor (EpoR). According to another embodiment, the cell population comprises dendritic cells. According to another embodiment, the cell population comprises T cells. According to another embodiment, the isolated erythropoietin (EPO)-derived oligopeptide of the pharmaceutical composition, once administered, contacts at least one cell population at a site of traumatic intracerebral hemorrhage. According to another embodiment, the isolated erythropoietin (EPO)-derived oligopeptide of the pharmaceutical composition, once administered, contacts at least one cell population at a site of intraparenchymal bleeding.

According to another aspect, the described invention provides a method for treating a traumatic brain injury having an inflammatory component in a subject in need thereof, the method comprising: (a) providing a pharmaceutical composition comprising: (i) a therapeutically effective amount of at least one isolated erythropoietin (EPO)-derived oligopeptide; and (ii) a pharmaceutically acceptable carrier; (b) administering the pharmaceutical composition of (a) to the subject; (c) treating at least one symptom of the traumatic brain injury; and (d) maintaining red blood cell indices of the subject at substantially normal levels during treatment.

According to one embodiment of the method, the at least one isolated erythropoietin (EPO)-derived oligopeptide is a cyclic peptide. According to another embodiment, the at least one isolated erythropoietin (EPO)-derived oligopeptide is at least one cyclic peptide selected from the group consisting of JM-4 (SEQ ID NO: 1), JM-5 (SEQ ID NO: 9), and JM-7 (SEQ ID NO: 11). According to another embodiment, the at least one isolated erythropoietin (EPO)-derived oligopeptide is JM-4 (SEQ ID NO: 1). According to another embodiment, the at least one isolated erythropoietin (EPO)-derived oligopeptide has at least 90% amino acid sequence identity to JM-4 (SEQ ID NO: 1). According to another embodiment, the isolated erythropoietin (EPO)-derived oligopeptide is a stabilized isolated erythropoietin (EPO)-derived oligopeptide, wherein the stabilized isolated erythropoietin (EPO)-derived oligopeptide comprises at least one small bicyclic compound added to either an N-terminal end or a C-terminal end of the isolated erythropoietin (EPO)-derived oligopeptide. According to another embodiment, the at least one small bicyclic molecule is biotin. According to another embodiment, the symptom of the traumatic brain injury is at least one symptom selected from the group consisting of hypotension, hypoxemia, brain swelling, headache, a neck pain, a difficulty remembering, a difficulty concentrating, a difficulty making decisions, fatigue, a mood change, nausea, photophobia, blurred vision, ear ringings, a loss of sense of taste, and a loss of sense of smell, seizures, coma, muscle weakness, paralysis, and a progressive decline in neurologic function following the traumatic brain injury. According to another embodiment, administering step (b) occurs within about 15 minutes after the traumatic brain injury. According to another embodiment, administering step (b) occurs within about 1 hour after the traumatic brain injury. According to another embodiment, administering step (b) occurs within about 3 hours after the traumatic brain injury. According to another embodiment, administering step (b) occurs within about 6 hours after the traumatic brain injury. According to another embodiment, administering step (b) occurs within about 9 hours after the traumatic brain injury. According to another embodiment, administering step (b) occurs within about 24 hours after the traumatic brain injury. According to another embodiment, treating step (c) further comprises reducing infiltration of a population of mononuclear cell in the brain of the subject. According to another embodiment, treating step (c) further comprises reducing axonal damage in at least one region of the brain of the subject affected by the traumatic brain injury. According to another embodiment, treating step (c) further comprises reducing neuronal cell death in at least one region of the brain of the subject affected by the traumatic brain injury. According to another embodiment, treating step (c) further comprises reducing neuronal cell death in at least one region of the brain of the subject affected, directly or indirectly, by the disease, disorder or condition. According to another embodiment, treating step (c) further comprises reducing glial cell death in at least one region of the brain of the subject affected, directly or indirectly, by the disease, disorder or condition. According to another embodiment, treating step (c) further comprises reducing neuronal and glial cell death in at least one region of the brain of the subject affected, directly or indirectly, by the disease, disorder or condition. According to another embodiment, treating step (c) further comprises improving a neurological deficit. According to another embodiment, the therapeutically effective amount is from about 0.000001 mg/kg body weight to about 10 g/kg body weight. According to another embodiment, the red blood cell indices in (d) comprise a hematocrit, and wherein the hematocrit is maintained at a stable level. According to another embodiment, the red blood cell indices in (d) comprise a hematocrit, and wherein the hematocrit is maintained within about 20% of a reference value or baseline level. According to another embodiment, the isolated erythropoietin (EPO)-derived oligopeptide of the pharmaceutical composition, once administered, contacts at least one cell population that does not express erythropoietin receptor (EpoR). According to another embodiment, the cell population comprises dendritic cells. According to another embodiment, the cell population comprises T cells. According to another embodiment, the isolated erythropoietin (EPO)-derived oligopeptide of the pharmaceutical composition, once administered, contacts at least one cell population at a site of traumatic intracerebral hemorrhage. According to another embodiment, the isolated erythropoietin (EPO)-derived oligopeptide of the pharmaceutical composition, once administered, contacts at least one cell population at a site of intraparenchymal bleeding.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

DETAILED DESCRIPTION OF THE INVENTION

Glossary

Figure 1:
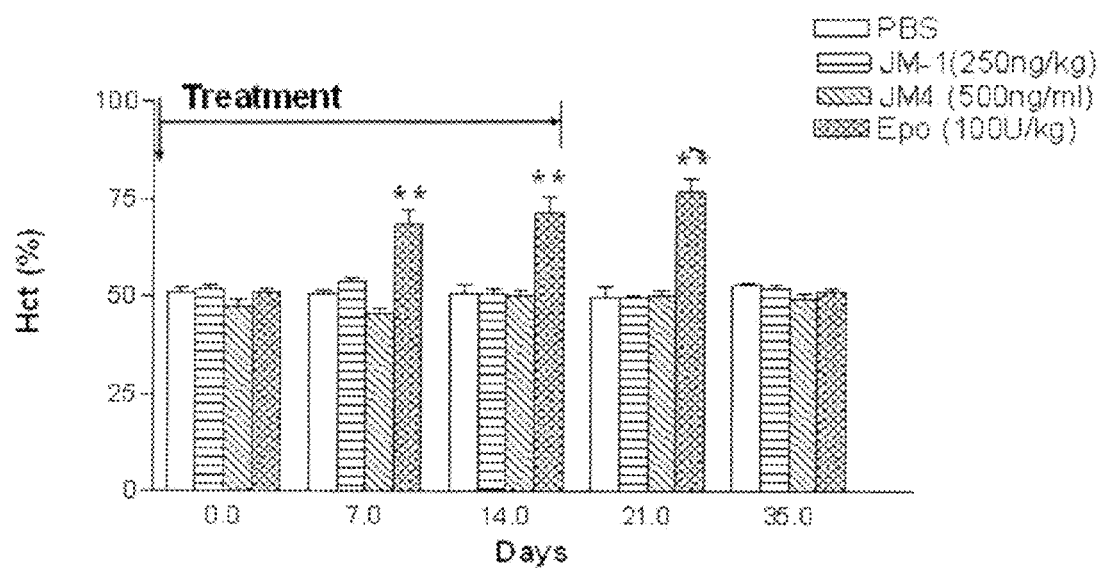
FIG. 1 shows a graph of the level of hematocrit (%) versus time (days) for mice treated with PBS, JM-1 peptide, JM-4 peptide, and rhEPO.

The term "adjuvant" as used herein refers to any component which improves the characteristics, efficacy or potency of a formulation, drug, or immunological agent.

The term "administer" as used herein refers to dispensing, supplying, applying, giving, apportioning or contributing. The terms "administering" or "administration" are used interchangeably and include in vivo administration, as well as administration directly to tissue ex vivo. Generally, compositions may be administered systemically either orally, buccally, parenterally, topically, by inhalation or insufflation (i.e., through the mouth or through the nose), or rectally in dosage unit formulations containing the conventional nontoxic pharmaceutically acceptable carriers, adjuvants, and vehicles as desired, or may be locally administered by means such as, but not limited to, injection, implantation, grafting, topical application, or parenterally. The term "parenteral" as used herein refers to introduction into the body by way of an injection (i.e., administration by injection), including, for example, subcutaneously (i.e., an injection beneath the skin), intramuscularly (i.e., an injection into a muscle), intravenously (i.e., an injection into a vein), intrathecally (i.e., an injection into the space around the spinal cord or under the arachnoid membrane of the brain), intrasternal injection or infusion techniques. A parenterally administered composition is delivered using a needle, e.g., a surgical needle. The term "surgical needle" as used herein, refers to any needle adapted for delivery of fluid (i.e., capable of flow) compositions into a selected anatomical structure. Injectable preparations, such as sterile injectable aqueous or oleaginous suspensions, may be formulated according to the known art using suitable dispersing or wetting agents and suspending agents.

Additional administration may be performed, for example, intravenously, pericardially, orally, via implant, transmucosally, transdermally, intramuscularly, subcutaneously, intraperitoneally, intrathecally, intralymphatically, intralesionally, or epidurally. Administration can be performed, for example, once, a plurality of times, and/or over one or more extended periods. The term "topical administration" and "topically applying" as used herein are used interchangeably to refer to delivering a peptide, the nucleic acid, or a vector comprising the peptide or the nucleic acid onto one or more surfaces of a tissue or cell, including epithelial surfaces.'

Topical administration, in contrast to transdermal administration, generally provides a local rather than a systemic effect. The terms "topical administration" and "transdermal administration" as used herein, unless otherwise stated or implied, are used interchangeably.

The term "agonist" as used herein refers to a chemical substance capable of activating a receptor to induce a full or partial pharmacological response. Receptors can be activated or inactivated by either endogenous or exogenous agonists and antagonists, resulting in stimulating or inhibiting a biological response. A physiological agonist is a substance that creates the same bodily responses, but does not bind to the same receptor. An endogenous agonist for a particular receptor is a compound naturally produced by the body which binds to and activates that receptor. A superagonist is a compound that is capable of producing a greater maximal response than the endogenous agonist for the target receptor, and thus an efficiency greater than 100%. This does not necessarily mean that it is more potent than the endogenous agonist, but is rather a comparison of the maximum possible response that can be produced inside a cell following receptor binding. Full agonists bind and activate a receptor, displaying full efficacy at that receptor. Partial agonists also bind and activate a given receptor, but have only partial efficacy at the receptor relative to a full agonist. An inverse agonist is an agent which binds to the same receptor binding-site as an agonist for that receptor and reverses constitutive activity of receptors. Inverse agonists exert the opposite pharmacological effect of a receptor agonist. An irreversible agonist is a type of agonist that binds permanently to a receptor in such a manner that the receptor is permanently activated. It is distinct from a mere agonist in that the association of an agonist to a receptor is reversible, whereas the binding of an irreversible agonist to a receptor is believed to be irreversible. This causes the compound to produce a brief burst of agonist activity, followed by desensitization and internalization of the receptor, which with long-term treatment produces an effect more like an antagonist. A selective agonist is specific for one certain type of receptor.

The terms "amino acid residue" or "amino acid" or "residue" are used interchangeably to refer to an amino acid that is incorporated into a protein, a polypeptide, or a peptide, including, but not limited to, a naturally occurring amino acid and known analogs of natural amino acids that can function in a similar manner as naturally occurring amino acids.

The abbreviations used herein for amino acids are those abbreviations which are conventionally used: A=Ala=Alanine; R=Arg=Arginine; N=Asn=Asparagine; D=Asp=Aspartic acid; C=Cys=Cysteine; Q=Gln=Glutamine; E=Glu=Glutamic acid; G=Gly=Glycine; H=His=Histidine; I=Ile=Isoleucine; L=Leu=Leucine; K=Lys=Lysine; M=Met=Methionine; F=Phe=Phenylalanine; P=Pro=Proline; S=Ser=Serine; T=Thr=Threonine; W=Trp=Tryptophan; Y=Tyr=Tyrosine; V=Val=Valine. The amino acids may be L- or D-amino acids. An amino acid may be replaced by a synthetic amino acid which is altered so as to increase the half-life of the peptide or to increase the potency of the peptide, or to increase the bioavailability of the peptide.

The following represent groups of amino acids that are conservative substitutions for one another:

Alanine (A), Serine (S), Threonine (T);
Aspartic Acid (D), Glutamic Acid (E);
Asparagine (N), Glutamic Acid (Q);
Arginine (R), Lysine (K);
Isoleucine (I), Leucine (L), Methionine (M), Valine (V); and
Phenylalanine (F), Tyrosine (Y), Tryptophan (W).

The term "antagonist" as used herein refers to a substance that counteracts the effects of another substance.

"Anesthetic agents" as used herein refers to agents that result in a reduction or loss of sensation. Non-limiting examples of anesthetic drugs that are suitable for use in the context of the present invention include pharmaceutically acceptable salts of lidocaine, bupivacaine, chlorprocaine, dibucaine, etidocaine, mepivacaine, tetracaine, dyclonine, hexylcaine, procaine, cocaine, ketamine, pramoxine and phenol.

The term "associate" and its various grammatical forms as used herein refers to joining, connecting, or combining to, either directly, indirectly, actively, inactively, inertly, non-inertly, completely or incompletely.

The term "attenuate" and its various grammatical forms as used herein means to weaken or reduce in force, intensity, effect, or quantity.

The term "biocompatible" as used herein refers to causing no clinically relevant tissue irritation, injury, toxic reaction, or immunological reaction to living tissue based on a clinical risk/benefit assessment.

The term "biodegradable" as used herein refers to material that will degrade actively or passively over time by simple chemical processes, by action of body enzymes or by other similar mechanisms in the human body.

The term "biomarkers" (or "biosignatures") as used herein refers to peptides, proteins, nucleic acids, antibodies, genes, metabolites, or any other substances used as indicators of a biologic state. It is a characteristic that is measured objectively and evaluated as a cellular or molecular indicator of normal biologic processes, pathogenic processes, or pharmacologic responses to a therapeutic intervention. The term "indicator" as used herein refers to any substance, number or ratio derived from a series of observed facts that may reveal relative changes as a function of time; or a signal, sign, mark, note or symptom that is visible or evidence of the existence or presence thereof. Once a proposed biomarker has been validated, it may be used to diagnose disease risk, presence of disease in an individual, or to tailor treatments for the disease in an individual (choices of drug treatment or administration regimes). In evaluating potential drug therapies, a biomarker may be used as a surrogate for a natural endpoint, such as survival or irreversible morbidity. If a treatment alters the biomarker, and that alteration has a direct connection to improved health, the biomarker may serve as a surrogate endpoint for evaluating clinical benefit. Clinical endpoints are variables that can be used to measure how patients feel, function or survive. Surrogate endpoints are biomarkers that are intended to substitute for a clinical endpoint; these biomarkers are demonstrated to predict a clinical endpoint with a confidence level acceptable to regulators and the clinical community.

The term "carrier" as used herein refers to an organic or inorganic ingredient, natural or synthetic, with which the active ingredient is combined to facilitate the application that does not cause significant irritation to an organism and does not abrogate the biological activity and properties of the composition of the described invention. Carriers must be of sufficiently high purity and of sufficiently low toxicity to render them suitable for administration to a subject being treated. The carrier can be inert, or it can possess pharmaceutical benefits, cosmetic benefits or both.

The term "concomitant" as used herein means associated with or occurring with.

The term "condition" as used herein refers to a variety of health states and is meant to include disorders or diseases caused by any underlying mechanism or disorder, injury, and the promotion of healthy tissues and organs.

The term "contact" as used herein refers to a state or condition of touching or of immediate or local proximity. The term "contacting" as used herein refers to bringing or putting in contact. Contacting a composition to a target destination, such as, but not limited to, an organ, tissue, cell, or tumor, may occur by any means of administration known to the skilled artisan.

The term "compatible" as used herein refers to the components of a composition are capable of being combined with each other in a manner such that there is no interaction that would substantially reduce the efficacy of the composition under ordinary use conditions.

The term "cytokine" as used herein refers to small soluble protein substances secreted by cells which have a variety of effects on other cells. Cytokines mediate many important physiological functions including growth, development, wound healing, and the immune response. They act by binding to their cell-specific receptors located in the cell membrane, which allows a distinct signal transduction cascade to start in the cell, which eventually will lead to biochemical and phenotypic changes in target cells. Generally, cytokines act locally. They include type I cytokines, which encompass many of the interleukins, as well as several hematopoietic growth factors; type II cytokines, including the interferons and interleukin-10; tumor necrosis factor ("TNF")-related molecules, including TNFα and lymphotoxin; immunoglobulin super-family members, including interleukin 1 ("IL-1"); and the chemokines, a family of molecules that play a critical role in a wide variety of immune and inflammatory functions. The same cytokine can have different effects on a cell depending on the state of the cell. Cytokines often regulate the expression of, and trigger cascades of, other cytokines.

The term "delayed release" is used herein in its conventional sense to refer to a drug formulation in which there is a time delay between administration of the formulation and the release of the drug there from. "Delayed release" may or may not involve gradual release of drug over an extended period of time, and thus may or may not be "sustained release."

The term "derivative" as used herein means a compound that may be produced from another compound of similar structure in one or more steps. A "derivative" or "derivatives" of a peptide or a compound retains at least a degree of the desired function of the peptide or compound. Accordingly, an alternate term for "derivative" may be "functional derivative."

The term "disease" or "disorder" as used herein generally refers to an impairment of health or a condition of abnormal functioning.

The term "domain" as used herein refers to a structural unit of a protein that folds more or less independently to form a globular compact structure.

The term "drug" as used herein refers to a therapeutic agent or any substance, other than food, used in the prevention, diagnosis, alleviation, treatment, or cure of disease.

The term "effective amount" refers to the amount necessary or sufficient to realize a desired biologic effect.

The term "emulsion" as used herein refers to a two-phase system prepared by combining two immiscible liquid carriers, one of which is disbursed uniformly throughout the other and consists of globules that have diameters equal to or greater than those of the largest colloidal particles. The globule size is critical and must be such that the system achieves maximum stability. A stable basic emulsion contains at least the two liquids and an emulsifying agent. Common types of emulsions are oil-in-water, where oil is the dispersed liquid and an aqueous solution, such as water, is the dispersion medium, and water-in-oil, where, conversely, an aqueous solution is the dispersed phase. It also is possible to prepare emulsions that are nonaqueous.

The term "EPO-derived oligopeptide," "erythropoietin (EPO)-derived oligopeptide," "EPO AB loop peptide," and "short EPO peptide" are used interchangeably to refer to an isolated or synthetic peptide encoding a fragment of mammalian erythropoietin (EPO). The term "oligopeptide" as used herein refers to any molecule that contains a small number (for example, 2 to about 30) of amino acid residues connected by peptide bonds. The term "EPO-derived oligopeptide" as used herein also includes an isolated or synthetic peptide encoding a fragment of mammalian erythropoietin (EPO), which contains additional chemical moieties, which are not normally a part of the peptide.

Examples of erythropoietin (EPO)-derived oligopeptides include, but are not limited to, the following peptides, each of whose amino acid sequence is shown from its N-terminal end to its C terminal end:

EPOp2 peptide, whose amino acid sequence is TTGCAEHCSLNENITVPDTK (SEQ ID NO: 3);

JM peptide, whose amino acid sequence is AEHCSLNENITVPDTKVNFYAWRME (SEQ ID NO: 4);

JM-1L peptide, whose amino acid sequence is CAEHCSLNENITVPDTKV (SEQ ID NO: 5);

JM-0biotin N-peptide, a biotinylated derivative of JM0 peptide, whose amino acid sequence is d-biotin-AEHCSLNENITVPDTKV (SEQ ID NO: 6);

JM-3S peptide, whose amino acid sequence is CAEHCS (SEQ ID NO: 7);

JM-3L peptide, whose amino acid sequence is GCAEHCSL (SEQ ID NO: 8);

JM-4 peptide, whose amino acid sequence is GCAEHCSLNENITVPDTKV (SEQ ID NO: 1);

JM-4biotin peptide, a biotinylated derivative of JM-4 peptide, whose amino acid sequence is dBiotin-GCAEHCSLNENITVPDTKV (SEQ ID NO: 23);

JM-5 peptide, whose amino acid sequence is CAEHCSLNENITVP (SEQ ID NO: 9);

JM-5biotin-N peptide, a biotinylated derivative of JM-5 peptide, whose amino acid sequence is d-biotin-AEHCSLNENITVP (SEQ ID NO: 24);

JM-6 peptide, whose amino acid sequence is TTGCAEHCSLNENITVPDTKV (SEQ ID NO: 10);

JM-7 peptide, whose amino acid sequence is TTGCAEHCSLNENITVP (SEQ ID NO: 11);

JM-14 peptide, whose amino acid sequence is SLNENITVPDTKV (SEQ ID NO: 12);

JM0biotin-C peptide, a biotinylated derivative of JM0 peptide, whose amino acid sequence is AEHCSLNENITVPDTKV-biotin (SEQ ID NO: 25);

BW2L peptide, whose amino acid sequence is CAEHCSLNKNINLDSVDGVP (SEQ ID NO: 13);

BW2biotin peptide, a biotinylated derivative of -hCNTF peptide, whose amino acid sequence is YVKHQGLNKNINLDSVDGVP-biotin (SEQ ID NO: 26);

BW3L peptide, whose amino acid sequence is GCAEHCSLMENNLRRPNL (SEQ ID NO: 14);

BW3Lbiotin peptide, a biotinylated derivative of BW3L peptide, whose amino acid sequence is dBiotin-GCAEHCSLMENNLRRPNL (SEQ ID NO: 27);

BW3biotin-N peptide, a biotinylated derivative of hIL-3 peptide, whose amino acid sequence is dBiotin-ILMENNLRRPNL (SEQ ID NO: 28);

BW4biotin-N peptide, a biotinylated derivative of a truncated EPO-hIL-3 peptide, whose amino acid sequence is dBiotin-AEHCSLMENNLRRPNL (SEQ ID NO: 29);

JM0 peptide, whose amino acid sequence is AEHCSLNENITVPDTKV (SEQ ID NO: 15);

JM5biotin-C peptide, whose amino acid sequence is AEHCSLNENITVP-d-biotin (SEQ ID NO: 30);

hCNTF peptide, whose amino acid sequence is YVKHQGLNKNINLDSVDGVP (SEQ ID NO: 16);

hIL-3 peptide, whose amino acid sequence is LMENNLRRPNL (SEQ ID NO: 17); and

BW4 peptide, whose amino acid sequence is AEHCSLMENNLRRPNL (SEQ ID NO: 18).

The term "erythropoietin" (EPO) refers to the principal hormone involved in the regulation of erythrocyte differentiation and the maintenance of a physiological level of circulating erythrocyte mass. The EPO molecule is an 193 amino acid peptide having amino acid sequence MGVHECPAWLWLLLSLLSLPLGLPVLGAPPRLICDSRVLERYLLEAKEAENITTGCAEHC SLNENITVPDTKVNFYAWKRMEVGQQAVEVWQGLALLSEAVLRGQALLVNSSQPWEP LQLHVDKAVSGLRSLTTLLRALGAQKEAISPPDAASAAPLRTITADTFRKLFRVYSNFLR GKLKLYTGEACRTGDR (SEQ ID NO: 19) that is further processed into a mature form. The EPO molecule comprises:

1) signal peptide (positions 1-27) having amino acid sequence MGVHECPAWLWLLLSLLSLPLGLPVLG (SEQ ID NO: 20);

2) chain (positions 28-193) having amino acid sequence APPRLICDSRVLERYLLEAKEAENITTGCAEHCSLNENITVPDTKVNFYAWKRMEVGQQ AVEVWQGLALLSEAVLRGQALLVNSSQPWEPLQLHVDKAVSGLRSLTTLLRALGAQKE AISPPDAASAAPLRTITADTFRKLFRVYSNFLRGKLKLYTGEACRTGDR (SEQ ID NO: 21);

3) propeptide (positions 190-193) having amino acid sequence TGDR (SEQ ID NO: 23); and 4) propeptide (position 193) (R).

The terms "whole EPO" and "whole EPO molecule" are used interchangeably herein to refer to the 165 amino acid peptide backbone (chain) of recombinant EPO protein, having substantial identity to amino acid sequence APPRLICDSRVLERYLLEAKEAENITTGCAEHCSLNENITVPNTKVNFYAWKRMEVGQQ AVEVWQGLALLSEAVLRGQALLVNSSQPWEPLQLHVDLAVSGLRSLTTLLRALGAQLE AISPPDAASAAPLRTITANTFRKLFRVYSNRLRGKLKLYTQEACRTGD (SEQ ID NO: 22). This backbone contains three N-linked carbohydrates attached to Asp24, Asp38, and Asp83 and one O-linked carbohydrate attached to Ser126. (see Browne, J K, et al., Erythropoietin: gene cloning, protein structure, and biological properties. Cold Spring Harb. Symp. Quant. Biol. 51:693-702, 1986; the contents of which are incorporated herein by reference in their entirety).

The term "glioma" as used herein refers to type of tumor that arises from cells of neuroglial origin, including astrocytes, oligodendrocytes, and ependymal cells, respectively.

The term "hematocrit" (Ht, packed cell volume (PCV), erythrocyte volume fraction (EVF)) refers to the proportion of blood volume that is occupied by red blood cells. "Red Blood Cell Count" (RBC) refers to the total number of red blood cells in a quantity of blood.

"Hormone" as used herein refers to natural substances produced by organs of the body that travel by blood to trigger activity in other locations or their synthetic analogs.

The term "hybridization" refers to the binding of two single stranded nucleic acid molecules to each other through base pairing. Nucleotides will bind to their complement under normal conditions, so two perfectly complementary strands will bind (or 'anneal') to each other readily. However, due to the different molecular geometries of the nucleotides, a single inconsistency between the two strands will make binding between them more energetically unfavorable. The effects of base incompatibility may be measured by quantifying the rate at which two strands anneal, this may provide information as to the similarity in base sequence between the two strands being annealed.

The term "hydrogel" as used herein refers to a substance resulting in a solid, semisolid, pseudoplastic, or plastic structure containing a necessary aqueous component to produce a gelatinous or jelly-like mass. The hydrogel incorporates and retains significant amounts of H2O, which eventually will reach an equilibrium content in the presence of an aqueous environment.

The term "hydrophilic" as used herein refers to a material or substance having an affinity for polar substances, such as water.

The term "hypotension" as used herein refers to decreased or lowered blood pressure.

The term "hypoxemia" as used herein refers to inadequate oxygenation of the blood.

The terms "in the body", "void volume", "resection pocket", "excavation", "injection site", "deposition site" or "implant site" as used herein are meant to include all tissues of the body without limit, and may refer to spaces formed therein from injections, surgical incisions, tumor or tissue removal, tissue injuries, abscess formation, or any other similar cavity, space, or pocket formed thus by action of clinical assessment, treatment or physiologic response to disease or pathology as non-limiting examples thereof.

The term "inflammatory brain disease or disorder" as used herein refers to a brain disease or disorder caused by acute or chronic inflammatory responses in the central nervous system. Acute inflammatory responses in the brain includes, for example, activation of microglia, appearance of dendritic cells, and the release of pro-inflammatory cytokines and chemokines in the central nervous system. Chronic inflammatory responses include, for example, long-standing activation of microglia and subsequent sustained release of inflammatory mediators. Such long-standing activation of microglia results in activation and proliferation of additional microglia, and further release of inflammatory factors. Examples of chronic inflammatory brain diseases or disorders include, but are not limited to, a neurodegenerative disease, such as, Alzheimer's disease (AD), Parkinson's disease (PD), Huntington's disease, amyotrophic lateral sclerosis (ALS), and age-related macular degeneration (ARMD).

The terms "inhibiting", "inhibit" or "inhibition" as used herein are used to refer to reducing the amount or rate of a process, to stopping the process entirely, or to decreasing, limiting, or blocking the action or function thereof. Inhibition may include a reduction or decrease of the amount, rate, action function, or process by at least 5%, at least 10%, at least 15%, at least 20%, at least 25%, at least 30%, at least 40%, at least 45%, at least 50%, at least 55%, at least 60%, at least 65%, at least 70%, at least 75%, at least 80%, at least 85%, at least 90%, at least 95%, at least 98%, or at least 99% when compared to a reference substance, wherein the reference substance is a substance that is not inhibited.

The term "injury" as used herein refers to damage or harm to a structure or function of the body caused by an outside agent or force, which may be physical or chemical.

The term "isolated" refers to material, such as a nucleic acid, a peptide, or a protein, which is: (1) substantially or essentially free from components that normally accompany or interact with it as found in its naturally occurring environment. The terms "substantially or essentially free" are used to refer to a material, which is at least 80% free from components that normally accompany or interact with it as found in its naturally occurring environment. The isolated material optionally comprises material not found with the material in its natural environment; or (2) if the material is in its natural environment, the material has been synthetically (non-naturally) altered by deliberate human intervention to a composition and/or placed at a location in the cell (e.g., genome or subcellular organelle) not native to a material found in that environment. The alteration to yield the synthetic material may be performed on the material within, or removed, from its natural state. For example, a naturally occurring nucleic acid becomes an isolated nucleic acid if it is altered, or if it is transcribed from DNA that has been altered, by means of human intervention performed within the cell from which it originates. See, for example, Compounds and Methods for Site Directed Mutagenesis in Eukaryotic Cells, Kmiec, U.S. Pat. No. 5,565,350; In Vivo Homologous Sequence Targeting in Eukaryotic Cells; Zarling et al., PCT/US93/03868. Likewise, a naturally occurring nucleic acid (for example, a promoter) becomes isolated if it is introduced by non-naturally occurring means to a locus of the genome not native to that nucleic acid. Nucleic acids that are "isolated" as defined herein also are referred to as "heterologous" nucleic acids.

The term "lipophilic" as used herein refers to preferring or possessing an affinity for a non-polar environment compared to a polar or aqueous environment.

The term "long-term release", as used herein, means that an implant is constructed and arranged to deliver therapeutic levels of an active ingredient for at least 7 days, or about 30 to about 60 days.

The term "macrophage" as used herein refers to a mononuclear, actively phagocytic cell arising from monocytic stem cells in the bone marrow. These cells are widely distributed in the body and vary in morphology and motility. Phagocytic activity is typically mediated by serum recognition factors, including certain immunoglobulins and components of the complement system, but also may be nonspecific. Macrophages also are involved in both the production of antibodies and in cell-mediated immune responses, particularly in presenting antigens to lymphocytes. They secrete a variety of immunoregulatory molecules.

The term "microglia" as used herein refers to the smallest of the glial cells that can act as phagocytic cells, cleaning up CNS debris. They are considered to be a type of immune cell found in the brain. Microglia are close cousins of other phagocytic cells including macrophages and dendritic cells. Like macrophages, microglia are derived from myeloid progenitor cells from the bone marrow. During embryonic development, these cells migrate to the CNS where they differentiate into microglia.

The term "mimetic" is used to refer to chemicals containing chemical moieties that mimic or the function of a peptide. For example, if a peptide contains two charged chemical moieties having functional activity, a mimetic places two charged chemical moieties in a spatial orientation and constrained structure so that the charged chemical function is maintained in three-dimensional space.

The term "mimic" refers to a substance that imitates, simulates, duplicates, or copies an activity or domain of EPO protein and a stabilizing domain of EPO protein (to stabilize the molecule) alone or in combination with another molecule which will produce a biological effect, namely immunomodulation and/or anti-inflammation.

The term "modulate" as used herein means to regulate, alter, adapt, or adjust to a certain measure or proportion.

The term "normal" refers to a standard, model, median or average of a large group.

The term "normal healthy subject" refers to a subject having no symptoms or other evidence of a traumatic brain injury or inflammatory disorder.

The term "nucleic acid" refers to a deoxyribonucleotide or ribonucleotide polymer in either single- or double-stranded form, and unless otherwise limited, encompasses known analogues having the essential nature of natural nucleotides in that they hybridize to single-stranded nucleic acids in a manner similar to naturally occurring nucleotides (e.g., peptide nucleic acids).

The term "nucleotide" refers to a chemical compound that consists of a heterocyclic base, a sugar, and one or more phosphate groups. In the most common nucleotides the base is a derivative of purine or pyrimidine, and the sugar is the pentose deoxyribose or ribose. Nucleotides are the monomers of nucleic acids, with three or more bonding together in order to form a nucleic acid. Nucleotides are the structural units of RNA, DNA, and several cofactors, including, but not limited to, CoA, FAD, DMN, NAD, and NADP. The purines include adenine (A), and guanine (G); the pyrimidines include cytosine (C), thymine (T), and uracil (U).

The term "parenteral" as used herein refers to introduction into the body by way of an injection (i.e., administration by injection), including, for example, subcutaneously (i.e., an injection beneath the skin), intramuscularly (i.e., an injection into a muscle); intravenously (i.e., an injection into a vein), intrathecally (i.e., an injection into the space around the spinal cord or under the arachnoid membrane of the brain), intrasternal injection, or infusion techniques. A parenterally administered composition is delivered using a needle, e.g., a surgical needle. The term "surgical needle" as used herein, refers to any needle adapted for delivery of fluid (i.e., capable of flow) compositions into a selected anatomical structure. Injectable preparations, such as sterile injectable aqueous or oleaginous suspensions, may be formulated according to the known art using suitable dispersing or wetting agents and suspending agents.

The term "particles" as used herein refers to refers to an extremely small constituent (e.g., nanoparticles, microparticles, or in some instances larger) that may contain in whole or in part the short EPO peptide composition as described herein.

The term "peptide" as used herein refers to two or more amino acids joined by a peptide bond.

The terms "polypeptide", "peptide" and "protein" are used interchangeably herein to refer to a polymer of amino acid residues. The terms apply to amino acid polymers in which one or more amino acid residue is an artificial chemical analogue of a corresponding naturally occurring amino acid, as well as to naturally occurring amino acid polymers. The essential nature of such analogues of naturally occurring amino acids is that, when incorporated into a protein that protein is specifically reactive to antibodies elicited to the same protein but consisting entirely of naturally occurring amino acids. The terms "polypeptide", "peptide" and "protein" also are inclusive of modifications including, but not limited to, glycosylation, lipid attachment, sulfation, gamma-carboxylation of glutamic acid residues, hydroxylation and ADP-ribosylation. It will be appreciated, as is well known and as noted above, that polypeptides may not be entirely linear. For instance, polypeptides may be branched as a result of ubiquitination, and they may be circular, with or without branching, generally as a result of posttranslational events, including natural processing event and events brought about by human manipulation which do not occur naturally. Circular, branched and branched circular polypeptides may be synthesized by non-translation natural process and by entirely synthetic methods, as well.

The term "peptidomimetic" as used herein refers to a small protein-like chain designed to mimic a peptide. A peptidomimetic typically arises from modification of an existing peptide in order to alter the molecule's properties.

The term "pharmaceutically acceptable carrier" as used herein refers to one or more compatible solid or liquid filler, diluents or encapsulating substances which are suitable for administration to a human or other vertebrate animal.

The term "pharmaceutical composition" is used herein to refer to a composition that is employed to prevent, reduce in intensity, cure or otherwise treat a target condition or disease.

As used herein the phrase "pharmaceutically acceptable carrier" refers to any substantially non-toxic carrier useable for formulation and administration of the composition of the described invention in which the product of the described invention will remain stable and bioavailable. the pharmaceutically acceptable carrier must be of sufficiently high purity and of sufficiently low toxicity to render it suitable for administration to the mammal being treated. It further should maintain the stability and bioavailability of an active agent. The pharmaceutically acceptable carrier can be liquid or solid and is selected, with the planned manner of administration in mind, to provide for the desired bulk, consistency, etc., when combined with an active agent and other components of a given composition. The term "pharmaceutically-acceptable carrier" as used herein refers to one or more compatible solid or liquid filler, diluents or encapsulating substances which are suitable for administration to a human or other vertebrate animal.

The term "pharmaceutically acceptable salt" as used herein refers to those salts which are, within the scope of sound medical judgment, suitable for use in contact with the tissues of humans and lower animals without undue toxicity, irritation, allergic response and the like and are commensurate with a reasonable benefit/risk ratio. When used in medicine the salts should be pharmaceutically acceptable, but non-pharmaceutically acceptable salts may conveniently be used to prepare pharmaceutically acceptable salts thereof. Such salts include, but are not limited to, those prepared from the following acids: hydrochloric, hydrobromic, sulphuric, nitric, phosphoric, maleic, acetic, salicylic, p-toluene sulphonic, tartaric, citric, methane sulphonic, formic, malonic, succinic, naphthalene-2-sulphonic, and benzene sulphonic. Also, such salts may be prepared as alkaline metal or alkaline earth salts, such as sodium, potassium or calcium salts of the carboxylic acid group. By "pharmaceutically acceptable salt" is meant those salts which are, within the scope of sound medical judgment, suitable for use in contact with the tissues of humans and lower animals without undue toxicity, irritation, allergic response and the like and are commensurate with a reasonable benefit/risk ratio. Pharmaceutically acceptable salts are well-known in the art. For example, P. H. Stahl, et al. describe pharmaceutically acceptable salts in detail in "Handbook of Pharmaceutical Salts: Properties, Selection, and Use" (Wiley VCH, Zurich, Switzerland: 2002). The salts may be prepared in situ during the final isolation and purification of the compounds described within the present invention or separately by reacting a free base function with a suitable organic acid. Representative acid addition salts include, but are not limited to, acetate, adipate, alginate, citrate, aspartate, benzoate, benzenesulfonate, bisulfate, butyrate, camphorate, camphorsufonate, digluconate, glycerophosphate, hemisulfate, heptanoate, hexanoate, fumarate, hydrochloride, hydrobromide, hydroiodide, 2-hydroxyethansulfonate (isethionate), lactate, maleate, methanesulfonate, nicotinate, 2-naphthalenesulfonate, oxalate, pamoate, pectinate, persulfate, 3-phenylpropionate, picrate, pivalate, propionate, succinate, tartrate, thiocyanate, phosphate, glutamate, bicarbonate, p-toluenesulfonate and undecanoate. Also, the basic nitrogen-containing groups may be quaternized with such agents as lower alkyl halides such as methyl, ethyl, propyl, and butyl chlorides, bromides and iodides; dialkyl sulfates like dimethyl, diethyl, dibutyl and diamyl sulfates; long chain halides such as decyl, lauryl, myristyl and stearyl chlorides, bromides and iodides; arylalkyl halides like benzyl and phenethyl bromides and others. Water or oil-soluble or dispersible products are thereby obtained. Examples of acids which may be employed to form pharmaceutically acceptable acid addition salts include such inorganic acids as hydrochloric acid, hydrobromic acid, sulphuric acid and phosphoric acid and such organic acids as oxalic acid, maleic acid, succinic acid and citric acid. Basic addition salts may be prepared in situ during the final isolation and purification of compounds described within the invention by reacting a carboxylic acid-containing moiety with a suitable base such as the hydroxide, carbonate or bicarbonate of a pharmaceutically acceptable metal cation or with ammonia or an organic primary, secondary or tertiary amine. Pharmaceutically acceptable salts include, but are not limited to, cations based on alkali metals or alkaline earth metals such as lithium, sodium, potassium, calcium, magnesium and aluminum salts and the like and nontoxic quaternary ammonia and amine cations including ammonium, tetramethylammonium, tetraethylammonium, methylamine, dimethylamine, trimethylamine, triethylamine, diethylamine, ethylamine and the like. Other representative organic amines useful for the formation of base addition salts include ethylenediamine, ethanolamine, diethanolamine, piperidine, piperazine and the like. Pharmaceutically acceptable salts also may be obtained using standard procedures well known in the art, for example by reacting a sufficiently basic compound such as an amine with a suitable acid affording a physiologically acceptable anion. Alkali metal (for example, sodium, potassium or lithium) or alkaline earth metal (for example calcium or magnesium) salts of carboxylic acids may also be made.

The term "polymer" as used herein refers to any of various chemical compounds made of smaller, identical molecules (called monomers) linked together. Polymers generally have high molecular weights. The process by which molecules are linked together to form polymers is called "polymerization."

The term "polynucleotide" refers to a deoxyribopolynucleotide, ribopolynucleotide, or analogs thereof that have the essential nature of a natural ribonucleotide in that they hybridize, under stringent hybridization conditions, to substantially the same nucleotide sequence as naturally occurring nucleotides and/or allow translation into the same amino acid(s) as the naturally occurring nucleotide(s). A polynucleotide may be full-length or a subsequence of a native or heterologous structural or regulatory gene. Unless otherwise indicated, the term includes reference to the specified sequence as well as the complementary sequence thereof. Thus, DNAs or RNAs with backbones modified for stability or for other reasons are "polynucleotides" as that term is intended herein. Moreover, DNAs or RNAs comprising unusual bases, such as inosine, or modified bases, such as tritylated bases, to name just two examples, are polynucleotides as the term is used herein. It will be appreciated that a great variety of modifications have been made to DNA and RNA that serve many useful purposes known to those of skill in the art. The term polynucleotide as it is employed herein embraces such chemically, enzymatically or metabolically modified forms of polynucleotides, as well as the chemical forms of DNA and RNA characteristic of viruses and cells, including among other things, simple and complex cells.

The term "primary sequence" as used herein refers to an amino acid sequence.

The term "prodrug" as used herein means a peptide or derivative, which is in an inactive form, and, which is converted to an active form by biological conversion following administration to a subject.

The term "progressive" as used herein refers to that which gradually advances in extent.

The term "prevent" as used herein refers to effectual stoppage of action or progress.

The following terms are used herein to describe the sequence relationships between two or more nucleic acids or polynucleotides: (a) "reference sequence", (b) "comparison window", (c) "sequence identity", (d) "percentage of sequence identity", and (e) "substantial identity".

The term "reference sequence" refers to a sequence used as a basis for sequence comparison. A reference sequence may be a subset or the entirety of a specified sequence; for example, as a segment of a full-length cDNA or gene sequence, or the complete cDNA or gene sequence.

The term "comparison window" refers to a contiguous and specified segment of a polynucleotide sequence, wherein the polynucleotide sequence may be compared to a reference sequence and wherein the portion of the polynucleotide sequence in the comparison window may comprise additions or deletions (i.e., gaps) compared to the reference sequence (which does not comprise additions or deletions) for optimal alignment of the two sequences. Generally, the comparison window is at least 20 contiguous nucleotides in length, and optionally can be at least 30 contiguous nucleotides in length, at least 40 contiguous nucleotides in length, at least 50 contiguous nucleotides in length, at least 100 contiguous nucleotides in length, or longer. Those of skill in the art understand that to avoid a high similarity to a reference sequence due to inclusion of gaps in the polynucleotide sequence, a gap penalty typically is introduced and is subtracted from the number of matches.

Methods of alignment of sequences for comparison are well-known in the art. Optimal alignment of sequences for comparison may be conducted by the local homology algorithm of Smith and Waterman, Adv. Appl. Math. 2:482 (1981); by the homology alignment algorithm of Needleman and Wunsch, J. Mol. Biol. 48:443 (1970); by the search for similarity method of Pearson and Lipman, Proc. Natl. Acad. Sci. 85:2444 (1988); by computerized implementations of these algorithms, including, but not limited to: CLUSTAL in the PC/Gene program by Intelligenetics, Mountain View, Calif.; GAP, BESTFIT, BLAST, FASTA, and TFASTA in the Wisconsin Genetics Software Package, Genetics Computer Group (GCG), 575 Science Dr., Madison, Wis., USA; the CLUSTAL program is well described by Higgins and Sharp, Gene 73:237-244 (1988); Higgins and Sharp, CABIOS 5:151-153 (1989); Corpet, et al., Nucleic Acids Research 16:10881-90 (1988); Huang, et al., Computer Applications in the Biosciences 8:155-65 (1992), and Pearson, et al., Methods in Molecular Biology 24:307-331 (1994). The BLAST family of programs, which can be used for database similarity searches, includes: BLASTN for nucleotide query sequences against nucleotide database sequences; BLASTX for nucleotide query sequences against protein database sequences; BLASTP for protein query sequences against protein database sequences; TBLASTN for protein query sequences against nucleotide database sequences; and TBLASTX for nucleotide query sequences against nucleotide database sequences. See, Current Protocols in Molecular Biology, Chapter 19, Ausubel, et al., Eds., Greene Publishing and Wiley-Interscience, New York (1995).

Unless otherwise stated, sequence identity/similarity values provided herein refer to the value obtained using the BLAST 2.0 suite of programs using default parameters. Altschul et al., Nucleic Acids Res. 25:3389-3402 (1997). Software for performing BLAST analyses is publicly available, e.g., through the National Center for Biotechnology-Information (http://www.hcbi.nlm.nih.gov/). This algorithm involves first identifying high scoring sequence pairs (HSPs) by identifying short words of length W in the query sequence, which either match or satisfy some positive-valued threshold score T when aligned with a word of the same length in a database sequence. T is referred to as the neighborhood word score threshold (Altschul et al., supra). These initial neighborhood word hits act as seeds for initiating searches to find longer HSPs containing them. The word hits then are extended in both directions along each sequence for as far as the cumulative alignment score can be increased. Cumulative scores are calculated using, for nucleotide sequences, the parameters M (reward score for a pair of matching residues; always>0) and N (penalty score for mismatching residues; always<0). For amino acid sequences, a scoring matrix is used to calculate the cumulative score. Extension of the word hits in each direction are halted when: the cumulative alignment score falls off by the quantity X from its maximum achieved value; the cumulative score goes to zero or below, due to the accumulation of one or more negative-scoring residue alignments; or the end of either sequence is reached. The BLAST algorithm parameters W, T, and X determine the sensitivity and speed of the alignment. The BLASTN program (for nucleotide sequences) uses as defaults a word length (W) of 11, an expectation (E) of 10, a cutoff of 100, M=5, N=−4, and a comparison of both strands. For amino acid sequences, the BLASTP program uses as defaults a word length (W) of 3, an expectation (E) of 10, and the BLOSUM62 scoring matrix (see Henikoff & Henikoff (1989) Proc. Natl. Acad. Sci. USA 89:10915).

In addition to calculating percent sequence identity, the BLAST algorithm also performs a statistical analysis of the similarity between two sequences (see, e.g., Karlin & Altschul, Proc. Natl. Acad. Sci. USA 90:5873-5787 (1993)). One measure of similarity provided by the BLAST algorithm is the smallest sum probability (P(N)), which provides an indication of the probability by which a match between two nucleotide or amino acid sequences would occur by chance. BLAST searches assume that proteins may be modeled as random sequences. However, many real proteins comprise regions of nonrandom sequences which may be homopolymeric tracts, short-period repeats, or regions enriched in one or more amino acids. Such low-complexity regions may be aligned between unrelated proteins even though other regions of the protein are entirely dissimilar. A number of low-complexity filter programs may be employed to reduce such low-complexity alignments. For example, the SEG (Wooten and Federhen, Comput. Chem., 17:149-163 (1993)) and XNU (Claverie and States, Comput. Chem., 17:191-201 (1993)) low-complexity filters may be employed alone or in combination.

As used herein, "sequence identity" or "identity" in the context of two nucleic acid or polypeptide sequences refers to the residues in the two sequences which are the same when aligned for maximum correspondence over a specified comparison window. When percentage of sequence identity is used in reference to proteins it is recognized that residue positions that are not identical often differ by conservative amino acid substitutions, i.e., where amino acid residues are substituted for other amino acid residues with similar chemical properties (e.g. charge or hydrophobicity) and therefore do not change the functional properties of the molecule. Where sequences differ in conservative substitutions, the percent sequence identity may be adjusted upwards to correct for the conservative nature of the substitution. Sequences that differ by such conservative substitutions are said to have "sequence similarity" or "similarity". Means for making this adjustment are well-known to those of skill in the art. Typically this involves scoring a conservative substitution as a partial rather than a full mismatch, thereby increasing the percentage sequence identity. Thus, for example, where an identical amino acid is given a score of 1 and a non-conservative substitution is given a score of zero, a conservative substitution is given a score between zero and 1. The scoring of conservative substitutions is calculated, e.g., according to the algorithm of Meyers and Miller, Computer Applic. Biol. Sci., 4:11-17 (1988) e.g., as implemented in the program PC/GENE (Intelligenetics, Mountain View, Calif., USA).

As used herein, "percentage of sequence identity" means the value determined by comparing two optimally aligned sequences over a comparison window, wherein the portion of the polynucleotide sequence in the comparison window may comprise additions or deletions (i.e., gaps) as compared to the reference sequence (which does not comprise additions or deletions) for optimal alignment of the two sequences. The percentage is calculated by determining the number of positions at which the identical nucleic acid base or amino acid residue occurs in both sequences to yield the number of matched positions, dividing the number of matched positions by the total number of positions in the window of comparison, and multiplying the result by 100 to yield the percentage of sequence identity.

The term "substantial identity" of polynucleotide sequences means that a polynucleotide comprises a sequence that has at least 70% sequence identity, at least 80% sequence identity, at least 90% sequence identity and at least 95% sequence identity, compared to a reference sequence using one of the alignment programs described using standard parameters. One of skill will recognize that these values may be adjusted appropriately to determine corresponding identity of proteins encoded by two nucleotide sequences by taking into account codon degeneracy, amino acid similarity, reading frame positioning and the like. Substantial identity of amino acid sequences for these purposes normally means sequence identity of at least 60%, or at least 70%, at least 80%, at least 90%, or at least 95%. Another indication that nucleotide sequences are substantially identical is if two molecules hybridize to each other under stringent conditions. However, nucleic acids that do not hybridize to each other under stringent conditions are still substantially identical if the polypeptides that they encode are substantially identical. This may occur, e.g., when a copy of a nucleic acid is created using the maximum codon degeneracy permitted by the genetic code. One indication that two nucleic acid sequences are substantially identical is that the polypeptide that the first nucleic acid encodes is immunologically cross reactive with the polypeptide encoded by the second nucleic acid.

The terms "substantial identity" in the context of a peptide indicates that a peptide comprises a sequence with at least 70% sequence identity to a reference sequence, at least 80%, at least 85%, at least 90% or 95% sequence identity to the reference sequence over a specified comparison window. Optionally, optimal alignment is conducted using the homology alignment algorithm of Needleman and Wunsch, J. Mol. Biol. 48:443 (1970). An indication that two peptide sequences are substantially identical is that one peptide is immunologically reactive with antibodies raised against the second peptide. Thus, a peptide is substantially identical to a second peptide, for example, where the two peptides differ only by a conservative substitution. Peptides which are "substantially similar" share sequences as noted above except that residue positions that are not identical may differ by conservative amino acid changes.

The term "recombinant" refers to a cell or vector that has been modified by the introduction of a heterologous nucleic acid or the cell that is derived from a cell so modified. Recombinant cells express genes that are not found in identical form within the native (non-recombinant) form of the cell or express native genes that are otherwise abnormally expressed, under-expressed or not expressed at all as a result of deliberate human intervention. The term "recombinant" as used herein does not encompass the alteration of the cell or vector by naturally occurring events (e.g., spontaneous mutation, natural transformation transduction/transposition) such as those occurring without deliberate human intervention.

The term "recombinant expression cassette" refers to a nucleic acid construct, generated recombinantly or synthetically, with a series of specified nucleic acid elements which permit transcription of a particular nucleic acid in a host cell. The recombinant expression cassette can be incorporated into a plasmid, chromosome, mitochondrial DNA, virus, or nucleic acid fragment. Typically, the recombinant expression cassette portion of an expression vector includes, among other sequences, a nucleic acid to be transcribed, a promoter, and a transcription termination signal such as a poly-A signal.

The term "recombinant host" refers to any prokaryotic or eukaryotic cell that contains either a cloning vector or an expression vector. This term also includes those prokaryotic or eukaryotic cells that have been genetically engineered to contain the cloned genes, or gene of interest, in the chromosome or genome of the host cell.

The term "recombinase" as used herein refers to an enzyme that catalyzes genetic recombination. A recombinase enzyme catalyzes the exchange of short pieces of DNA between two long DNA strands, particularly the exchange of homologous regions between the paired maternal and paternal chromosomes.

The term "recombinant protein" as used herein refers to a protein produced by genetic engineering.

The term "reduce" or "reducing" as used herein refers to a lowering or lessening in degree, intensity, state, condition, or extent.

The term "stable" as used herein means consistent. The term "stable" encompasses changes within 20% of a reference or baseline.

The term "subject" or "individual" or "patient" are used interchangeably to refer to a member of an animal species of mammalian origin, including but not limited to, a mouse, a rat, a cat, a goat, sheep, horse, hamster, ferret, platypus, pig, a dog, a guinea pig, a rabbit and a primate, such as, for example, a monkey, ape, or human.

The phrase "subject in need thereof" as used herein refers to a patient that (i) will be administered at least one short EPO peptide, (ii) is receiving at least one short EPO peptide; or (iii) has received at least one short EPO peptide, unless the context and usage of the phrase indicates otherwise.

The term "sustained release" (also referred to as "extended release") is used herein in its conventional sense to refer to a drug formulation that provides for gradual release of a drug over an extended period of time, and that preferably, although not necessarily, results in substantially constant blood levels of a drug over an extended time period.

The term "symptom" as used herein refers to an indication of disorder or disease, especially when experienced by an individual as a change from normal function, sensation, or appearance.

The term "syndrome" as used herein refers to a pattern of symptoms indicative of some disease or condition.

The term "therapeutic agent" as used herein refers to a drug, molecule, nucleic acid, protein, metabolite, peptide, composition or other substance that provides a therapeutic effect. The term "active" as used herein refers to the ingredient, component or constituent of the compositions of the present invention responsible for the intended therapeutic effect. The terms "therapeutic agent" and "active agent" are used interchangeably herein.

The term "therapeutic component" as used herein refers to a therapeutically effective dosage (i.e., dose and frequency of administration) that eliminates, reduces, or prevents the progression of a particular disease manifestation in a percentage of a population. An example of a commonly used therapeutic component is the ED50 which describes the dose in a particular dosage that is therapeutically effective for a particular disease manifestation in 50% of a population.

The term "therapeutic effect" as used herein refers to a consequence of treatment, the results of which are judged to be desirable and beneficial. A therapeutic effect may include, directly or indirectly, the arrest, reduction, or elimination of a disease manifestation. A therapeutic effect may also include, directly or indirectly, the arrest reduction or elimination of the progression of a disease manifestation. The term "therapeutically effective amount" or an "amount effective" of one or more of the active agents of the present invention is an amount that is sufficient to provide a therapeutic effect. Generally, an effective amount of the active agents that can be employed according to the described invention ranges from about 0.000001 mg/kg body weight to about 100 mg/kg body weight. However, dosage levels are based on a variety of factors, including the type of injury, the age, weight, sex, medical condition of the patient, the severity of the condition, the route of administration, and the particular active agent employed. Thus the dosage regimen may vary widely, but can be determined routinely by a physician using standard methods.

The term "topical" refers to administration of a composition at, or immediately beneath, the point of application. The phrase "topically applying" describes application onto one or more surfaces(s) including epithelial surfaces.

The term "treat" or "treating" includes abrogating, substantially inhibiting, slowing or reversing the progression of a disease, condition or disorder, substantially ameliorating clinical or esthetical symptoms of a condition, substantially preventing the appearance of clinical or esthetical symptoms of a disease, condition, or disorder, and protecting from harmful or annoying symptoms. Treating further refers to accomplishing one or more of the following: (a) reducing the severity of a disorder; (b) limiting the development of symptoms characteristic of a disorder being treated; (c) limiting the worsening of symptoms characteristic of a disorder being treated; (d) limiting the recurrence of a disorder in patients that previously had the disorder; and (e) limiting recurrence of symptoms in patients that were previously symptomatic for the disorder.

The term "TUNEL" refers to a histochemical protocol for the detection and quantification of apoptosis at the single cell level based on labeling of DNA strand breaks. DNA breaks occur late in the apoptotic pathway and are expressed by 95% of cell types. Nucleases that degrade the higher order chromatin structure of the DNA into fragments of 50 to 300 kilobases and subsequently into smaller DNA pieces of about 200 base pairs in length are activated during apoptosis. As the DNA strands are broken by the nucleases, a large number of 3'-hydroxyl ends of these strand fragments become exposed. This property is used to identify dying cells by labeling the 3'-hydroxyl ends. The enzyme terminal deoxynucleotidyl transferase (TdT) catalyzes a template independent addition of the dUTP's to the 3'-hydroxyl ends of double- or single-stranded DNA to blunt, recessed or overhanging ends. A substantial number of these sites are available in dying cells providing the basis for the method.

The term "variant" and its various grammatical forms as used herein refers to a nucleotide sequence or an amino acid sequence with substantial identity to a reference nucleotide sequence or reference amino acid sequence, respectively. The differences in the sequences may be the result of changes, either naturally or by design, in sequence or structure. Natural changes may arise during the course of normal replication or duplication in nature of a particular nucleic acid sequence. Designed changes may be specifically designed and introduced into the sequence for specific purposes. Such specific changes may be made in vitro using a variety of mutagenesis techniques. Such sequence variants generated specifically may be referred to as "mutants: or "derivatives" of the original sequence.

A skilled artisan likewise can produce polypeptide variants having single or multiple amino acid substitutions, deletions, additions or replacements. These variants may include inter alia: (a) variants in which one or more amino acid residues are substituted with conservative or non-conservative amino acids; (b) variants in which one or more amino acids are added; (c) variants in which at least on amino acid includes a substituent group; (d) variants in which a target protein is fused with another peptide or polypeptide such as a fusion partner, a protein tag or other chemical moiety, that may confer useful properties to the target protein, such as, for example, an epitope for an antibody. The techniques for obtaining such variants, including genetic (suppressions, deletions, mutations, etc.), chemical, and enzymatic techniques are known to the skilled artisan. As used herein, the term "mutation" refers to a change of the DNA sequence within a gene or chromosome of an organism resulting in the creation of a new character or trait not found in the parental type, or the process by which such a change occurs in a chromosome, either through an alteration in the nucleotide sequence of the DNA coding for a gene or through a change in the physical arrangement of a chromosome. Three mechanisms of mutation include substitution (exchange of one base pair for another), addition (the insertion of one or more bases into a sequence), and deletion (loss of one or more base pairs).

The term "substitution" is used herein to refer to that in which a base or bases are exchanged for another base or bases in the DNA. Substitutions may be synonymous substitutions or nonsynonymous substitutions. As used herein, "synonymous substitutions" refer to substitutions of one base for another in an exon of a gene coding for a protein, such that the amino acid sequence produced is not modified. The term "nonsynonymous substitutions" as used herein refer to substitutions of one base for another in an exon of a gene coding for a protein, such that the amino acid sequence produced is modified.

The term "deletion" and "deletion mutation" are used interchangeably herein to refer to that in which a base or bases are lost from the DNA.

The term "addition" as used herein refers to the insertion of one or more bases, or of one or more amino acids, into a sequence.

The term "vehicle" as used herein refers to a substance that facilitates the use of a drug or other material that is mixed with it.

1. Pharmaceutical Composition for Treating Traumatic Brain Injury or Inflammatory Brain Disease According to one aspect, the described invention provides a pharmaceutical composition for treating traumatic brain injury (TBI) or an inflammatory brain disease, disorder, or condition in a subject, the composition comprising:

(a) a therapeutically effective amount of at least one isolated erythropoietin (EPO)-derived oligopeptide; and
(b) a pharmaceutically acceptable carrier.

According to some embodiments, the at least one isolated erythropoietin (EPO)-derived oligopeptide is a cyclic peptide. According to some such embodiments, the cyclic peptide is JM-4 (SEQ ID NO: 1). According to some such embodiments, the cyclic peptide is JM-5 (SEQ ID NO: 9). According to some such embodiments, the cyclic peptide is JM-7 (SEQ ID NO: 11).

According to another embodiment, the at least one isolated erythropoietin (EPO)-derived peptide is JM-4 having amino acid sequence GCAEHCSLNENITVPDTKV (SEQ ID NO: 1). According to another embodiment, the at least one isolated erythropoietin (EPO)-derived the amino acid sequence of isolated JM-4 comprises a sequence having substantial amino acid sequence identity to amino acid sequence: GCAEHCSLNENITVPDTKV (SEQ ID NO: 1). According to another embodiment, the amino acid sequence of isolated JM-4 comprises a sequence at least 90% identical to amino acid sequence: GCAEHCSLNENITVPDTKV (SEQ ID NO: 1). According to another embodiment, the amino acid sequence of isolated JM-4 comprises a sequence at least 91% identical to amino acid sequence: GCAEHCSLNENITVPDTKV (SEQ ID NO: 1). According to another embodiment, the amino acid sequence of isolated JM-4 comprises a sequence at least 92% identical to amino acid sequence: GCAEHCSLNENITVPDTKV (SEQ ID NO: 1). According to another embodiment, the amino acid sequence of isolated JM-4 comprises a sequence at least 93% identical to amino acid sequence: GCAEHCSLNENITVPDTKV (SEQ ID NO: 1). According to another embodiment, the amino acid sequence of isolated JM-4 comprises a sequence at least 94% identical to amino acid sequence: GCAEHCSLNENITVPDTKV (SEQ ID NO: 1). According to another embodiment, the amino acid sequence of isolated JM-4 comprises a sequence at least 96% identical to amino acid sequence: GCAEHCSLNENITVPDTKV (SEQ ID NO: 1). According to another embodiment, the amino acid sequence of isolated JM-4 comprises a sequence at least 97% identical to amino acid sequence: GCAEHCSLNENITVPDTKV (SEQ ID NO: 1). According to another embodiment, the amino acid sequence of isolated JM-4 comprises a sequence at least 98% identical to amino acid sequence: GCAEHCSLNENITVPDTKV (SEQ ID NO: 1). According to another embodiment, the amino acid sequence of isolated JM-4 comprises a sequence at least 99% identical to amino acid sequence: GCAEHCSLNENITVPDTKV (SEQ ID NO: 1).

According to another embodiment, the at least one isolated erythropoietin (EPO)-derived oligopeptide is a stabilized isolated erythropoietin (EPO)-derived oligopeptide, wherein the stabilized isolated erythropoietin (EPO)-derived oligopeptide comprises at least one small bicyclic (meaning containing two fused rings) compound added to either an N-terminal end or a C-terminal end of the isolated erythropoietin (EPO)-derived oligopeptide.

According to another embodiment, the at least one small bicyclic molecule is biotin.

According to another embodiment, the carrier is a pharmaceutically acceptable carrier.

According to another embodiment, the pharmaceutical composition, when it is desirable to deliver the composition locally, may be formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. Pharmaceutical formulations for parenteral administration include aqueous solutions of the active compounds in water-soluble form. Additionally, suspensions of the active compounds may be prepared as appropriate oily injection suspensions. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions. Alternatively, the active compounds may be in powder form for constitution with a suitable vehicle, e.g., sterile pyrogen-free water, before use.

The pharmaceutical compositions also may comprise suitable solid or gel phase carriers or excipients. Examples of such carriers or excipients include, but are not limited to, calcium carbonate, calcium phosphate, various sugars, starches, cellulose derivatives, gelatin, and polymers such as polyethylene glycols.

Suitable liquid or solid pharmaceutical preparation forms are, for example, microencapsulated, and if appropriate, with one or more excipients, encochleated, coated onto microscopic gold particles, contained in liposomes, pellets for implantation into the tissue, or dried onto an object to be rubbed into the tissue. Such pharmaceutical compositions also may be in the form of granules, beads, powders, tablets, coated tablets, (micro)capsules, suppositories, syrups, emulsions, suspensions, creams, drops or preparations with protracted release of active compounds, in whose preparation excipients and additives and/or auxiliaries such as disintegrants, binders, coating agents, swelling agents, lubricants, or solubilizers are customarily used as described above. The pharmaceutical compositions are suitable for use in a variety of drug delivery systems. For a brief review of methods for drug delivery, see Langer 1990 Science 249, 1527-1533, which is incorporated herein by reference.

The pharmaceutical composition, and optionally other therapeutics, may be administered per se (neat) or in the form of a pharmaceutically acceptable salt. When used in medicine the salts should be pharmaceutically acceptable, but non-pharmaceutically acceptable salts may conveniently be used to prepare pharmaceutically acceptable salts thereof. Such salts also may be prepared as alkaline metal or alkaline earth salts, such as sodium, potassium or calcium salts of the carboxylic acid group.

The formulations may be presented conveniently in unit dosage form and may be prepared by any of the methods well known in the art of pharmacy. All methods include the step of bringing into association a JM-4 peptide (SEQ ID NO: 1), or a pharmaceutically acceptable ester, salt, hydrate, solvate or prodrug thereof ("active compound") with the carrier which constitutes one or more accessory agents. In general, the formulations are prepared by uniformly and intimately bringing into association the active agent with liquid carriers or finely divided solid carriers or both and then, if necessary, shaping the product into the desired formulation.

The pharmaceutical agent or a pharmaceutically acceptable ester, salt, hydrate, solvate, or prodrug thereof may be mixed with other active materials that do not impair the desired action, or with materials that supplement the desired action. Solutions or suspensions used for parenteral, intradermal, subcutaneous, intrathecal, or topical application may include, but are not limited to, for example, the following components: a sterile diluent such as water for injection, saline solution, fixed oils, polyethylene glycols, glycerine, propylene glycol or other synthetic solvents; antibacterial agents such as benzyl alcohol or methyl parabens; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. The parental preparation may be enclosed in ampoules, disposable syringes or multiple dose vials made of glass or plastic. Administered intravenously, particular carriers are physiological saline or phosphate buffered saline (PBS).

Pharmaceutical compositions for parenteral injection comprise pharmaceutically acceptable sterile aqueous or nonaqueous solutions, dispersions, suspensions or emulsions and sterile powders for reconstitution into sterile injectable solutions or dispersions. A "solution" generally is considered as a homogeneous mixture of two or more substances. It is frequently, though not necessarily, a liquid. In a solution, the molecules of the solute (or dissolved substance) are uniformly distributed among those of the solvent. As used herein, "dispersed system" or "dispersion" refers to a two-phase system in which one phase is distributed as particles or droplets in the second, or continuous, phase. The term "suspension" as used herein refers to preparations of finely divided, undissolved substances dispersed in liquid vehicles. The particulate matter of a suspension may settle slowly from the liquid vehicle in which it is dispersed; therefore, suspensions should be shaken well before use to ensure uniform distribution of solid in the vehicle and thereby uniform and proper dosage. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions also may contain adjuvants including preservative agents, wetting agents, emulsifying agents, and dispersing agents. Prevention of the action of microorganisms may be ensured by various antibacterial and antifungal agents, for example, parabens, chlorobutanol, phenol, sorbic acid, and the like. It also may be desirable to include isotonic agents, for example, sugars, sodium chloride and the like. Prolonged absorption of the injectable pharmaceutical form may be brought about by the use of agents delaying absorption, for example, aluminum monostearate and gelatin.

Suspensions, in addition to the active compounds, may contain suspending agents, as, for example, ethoxylated isostearyl alcohols, polyoxyethylene sorbitol and sorbitan esters, microcrystalline cellulose, aluminum metahydroxide, bentonite, agar-agar, tragacanth, and mixtures thereof.

Injectable depot forms are made by forming microencapsulated matrices of the drug in biodegradable polymers such as polylactide-polyglycolide. Depending upon the ratio of drug to polymer and the nature of the particular polymer employed, the rate of drug release may be controlled. Such long acting formulations may be formulated with suitable polymeric or hydrophobic materials (for example as an emulsion in an acceptable oil) or ion exchange resins, or as sparingly soluble derivatives, for example, as a sparingly soluble salt. Examples of other biodegradable polymers include poly (orthoesters) and poly(anhydrides). Depot injectable formulations also are prepared by entrapping the drug in liposomes or microemulsions which are compatible with body tissues.

The locally injectable formulations may be sterilized, for example, by filtration through a bacterial-retaining filter or by incorporating sterilizing agents in the form of sterile solid compositions that may be dissolved or dispersed in sterile water or other sterile injectable medium just prior to use. Injectable preparations, for example, sterile injectable aqueous or oleaginous suspensions may be formulated according to the known art using suitable dispersing or wetting agents and suspending agents. The sterile injectable preparation also may be a sterile injectable solution, suspension or emulsion in a nontoxic, parenterally acceptable diluent or solvent such as a solution in 1,3-butanediol. Among the acceptable vehicles and solvents that may be employed are water, Ringer's solution, U.S.P. and isotonic sodium chloride solution. In addition, sterile, fixed oils conventionally are employed or as a solvent or suspending medium. For this purpose any bland fixed oil may be employed including synthetic mono- or diglycerides. In addition, fatty acids such as oleic acid are used in the preparation of injectables.

Formulations for parenteral (including but not limited to, subcutaneous, intradermal, intramuscular, intravenous, intrathecal and intraarticular) administration include aqueous and non-aqueous sterile injection solutions that may contain anti-oxidants, buffers, bacteriostats and solutes, which render the formulation isotonic with the blood of the intended recipient; and aqueous and non-aqueous sterile suspensions, which may include suspending agents and thickening agents. The formulations may be presented in unit-dose or multi-dose containers, for example sealed ampules and vials, and may be stored in a freeze-dried (lyophilized) condition requiring only the addition of the sterile liquid carrier, for example, saline, water-for-injection, immediately prior to use. Extemporaneous injection solutions and suspensions may be prepared from sterile powders, granules and tablets of the kind previously described.

Another method of formulation of the compositions described herein involves conjugating the compounds described herein to a polymer that enhances aqueous solubility. Examples of suitable polymers include but are not limited to polyethylene glycol, poly-(d-glutamic acid), poly-(l-glutamic acid), poly-(1-glutamic acid), poly-(d-aspartic acid), poly-(1-aspartic acid), poly-(1-aspartic acid) and copolymers thereof. Polyglutamic acids having molecular weights between about 5,000 to about 100,000, with molecular weights between about 20,000 and about 80,000 may be used and with molecular weights between about 30,000 and about 60,000 may also be used. The polymer is conjugated via an ester linkage to one or more hydroxyls of an inventive therapeutic inhibitor peptide using a protocol as essentially described by U.S. Pat. No. 5,977,163, which is incorporated herein by reference.

Suitable buffering agents include: acetic acid and a salt (1-2% w/v); citric acid and a salt (1-3% w/v); boric acid and a salt (0.5-2.5% w/v); and phosphoric acid and a salt (0.8-2% w/v). Suitable preservatives include benzalkonium chloride (0.003-0.03% w/v); chlorobutanol (0.3-0.9% w/v); parabens (0.01-0.25% w/v) and thimerosal (0.004-0.02% w/v).

According to another embodiment, the therapeutically effective amount is from about 0.000001 mg/kg body weight to about 10 g/kg body weight. According to another embodiment, the therapeutically effective amount is from about 0.000002 mg/kg body weight to about 10 g/kg body weight. According to another embodiment, the therapeutically effective amount is from about 0.000003 mg/kg body weight to about 10 g/kg body weight. According to another embodiment, the therapeutically effective amount is from about 0.000004 mg/kg body weight to about 10 g/kg body weight. According to another embodiment, the therapeutically effective amount is from about 0.000005 mg/kg body weight to about 10 g/kg body weight. According to another embodiment, the therapeutically effective amount is from about 0.000006 mg/kg body weight to about 10 g/kg body weight. According to another embodiment, the therapeutically effective amount is from about 0.000007 mg/kg body weight to about 10 g/kg body weight. According to another embodiment, the therapeutically effective amount is from about 0.000008 mg/kg body weight to about 10 g/kg body weight. According to another embodiment, the therapeutically effective amount is from about 0.000009 mg/kg body weight to about 10 g/kg body weight. According to another embodiment, the therapeutically effective amount is from about 0.00001 mg/kg body weight to about 10 g/kg body weight. According to another embodiment, the therapeutically effective amount is from about 0.00002 mg/kg body weight to about 10 g/kg body weight. According to another embodiment, the therapeutically effective amount is from about 0.0003 mg/kg body weight to about 10 g/kg body weight. According to another embodiment, the therapeutically effective amount is from about 0.00004 mg/kg body weight to about 10 g/kg body weight. According to another embodiment, the therapeutically effective amount is from about 0.00005 mg/kg body weight to about 10 g/kg body weight. According to another embodiment, the therapeutically effective amount is from about 0.00006 mg/kg body weight to about 10 g/kg body weight. According to another embodiment, the therapeutically effective amount is from about 0.00007 mg/kg body weight to about 10 g/kg body weight. According to another embodiment, the therapeutically effective amount is from about 0.00008 mg/kg body weight to about 10 g/kg body weight. According to another embodiment, the therapeutically effective amount is from about 0.00009 mg/kg body weight to about 10 g/kg body weight. According to another embodiment, the therapeutically effective amount is from about 0.0001 mg/kg body weight to about 10 g/kg body weight. According to some such embodiments, the therapeutically effective amount is about 0.0005 mg/kg body weight. According to some such embodiments, the therapeutically effective amount is about 0.001 mg/kg body weight. According to some such embodiments, the therapeutically effective amount is about 0.005 mg/kg body weight. According to some such embodiments, the therapeutically effective amount is about 0.01 mg/kg body weight. According to some such embodiment, the therapeutically effective amount is about 0.1 mg/kg body weight. According to some such embodiments, the therapeutically effective amount is about 1 mg/kg body weight. According to some such embodiments, the therapeutically effective amount is about 10 mg/kg body weight. According to some such embodiments, the therapeutically effective amount is about 20 mg/kg body weight. According to some such embodiments, the therapeutically effective amount is about 30 mg/kg body weight. According to some such embodiments, the therapeutically effective amount is about 40 mg/kg body weight. According to some such embodiments, the therapeutically effective amount is about 50 mg/kg body weight. According to some such embodiments, the therapeutically effective amount is about 60 mg/kg body weight. According to some such embodiments, the therapeutically effective amount is about 70 mg/kg body weight. According to some such embodiments, the therapeutically effective amount about 80 mg/kg body weight. According to some such embodiments, the therapeutically effective amount is about 90 mg/kg body weight. According to some such embodiments, the therapeutically effective amount is about 100 mg/kg body weight. According to some such embodiments, the therapeutically effective amount is about 110 mg/kg body weight. According to some such embodiments, the therapeutically effective amount is about 120 mg/kg body weight. According to some such embodiments, the therapeutically effective amount is about 130 mg/kg body weight. According to some such embodiments, the therapeutically effective amount is about 140 mg/kg body weight. According to some such embodiments, the therapeutically effective amount is about 150 mg/kg body weight. According to some such embodiments, the therapeutically effective amount is about 160 mg/kg body weight. According to some such embodiments, the therapeutically effective amount is about 170 mg/kg body weight. According to some such embodiments, the therapeutically effective amount is about 180 mg/kg body weight. According to some such embodiments, the therapeutically effective is about 190 mg/kg body weight. According to some such embodiments, the therapeutically effective amount is about 200 mg/kg body weight. According to some such embodiments, the therapeutically effective amount is about 250 mg/kg body weight. According to some such embodiments, the therapeutically effective amount is about 500 mg/kg body weight.

According to another embodiment, the pharmaceutical composition further comprises at least one additional active ingredient.

According to another embodiment, the pharmaceutical composition further comprises at least one additional active ingredient. Examples of the active ingredient include, but are not limited to, an antibiotic agent, an antifungal agent, an antiviral agent, an antiprotozoal agent, an anesthetic agent, a steroidal anti-inflammatory agent, a non-steroidal anti-inflammatory agent, an antipruritic agent, an anti-oxidant agent, a chemotherapeutic agent, an anti-histamine agent, a vitamin, a hormone, a cytokine, or a cytokine antagonist.

2. Methods for Treating a Traumatic Brain Injury

According to another aspect, the described invention provides a method for treating a traumatic brain injury having an inflammatory component in a subject in need thereof, the method comprising:

(a) providing a pharmaceutical composition comprising:
(i) a therapeutically effective amount of at least one isolated erythropoietin (EPO)-derived oligopeptide; and
(ii) a pharmaceutically acceptable carrier;
(b) administering the therapeutically effective amount of the pharmaceutical composition of (a) to the subject;
(c) treating at least one symptom of the traumatic brain injury; and
(d) maintaining red blood cell indices of the subject at substantially normal levels during treatment.

According to some embodiments of the method, the at least one isolated erythropoietin (EPO)-derived peptide is a cyclic peptide. According to some such embodiments, the cyclic peptide is JM-4 (SEQ ID NO: 1). According to some such embodiments, the cyclic peptide is JM-5 (SEQ ID NO: 9). According to some such embodiments, the cyclic peptide is JM-7 (SEQ ID NO: 11).

According to another embodiment, the amino acid sequence of isolated JM-4 comprises a sequence having substantial amino acid sequence identity to amino acid sequence: GCAEHCSLNENITVPDTKV (SEQ ID NO: 1). According to another embodiment, the amino acid sequence of isolated JM-4 comprises a sequence at least 90% identical to amino acid sequence: GCAEHCSLNENITVPDTKV (SEQ ID NO: 1). According to another embodiment, the amino acid sequence of isolated JM-4 comprises a sequence at least 91% identical to amino acid sequence: GCAEHCSLNENITVPDTKV (SEQ ID NO: 1). According to another embodiment, the amino acid sequence of isolated JM-4 comprises a sequence at least 92% identical to amino acid sequence: GCAEHCSLNENITVPDTKV (SEQ ID NO: 1). According to another embodiment, the amino acid sequence of isolated JM-4 comprises a sequence at least 93% identical to amino acid sequence: GCAEHCSLNENITVPDTKV (SEQ ID NO: 1). According to another embodiment, the amino acid sequence of isolated JM-4 comprises a sequence at least 94% identical to amino acid sequence: GCAEHCSLNENITVPDTKV (SEQ ID NO: 1). According to another embodiment, the amino acid sequence of isolated JM-4 comprises a sequence at least 96% identical to amino acid sequence: GCAEHCSLNENITVPDTKV (SEQ ID NO: 1). According to another embodiment, the amino acid sequence of isolated JM-4 comprises a sequence at least 97% identical to amino acid sequence: GCAEHCSLNENITVPDTKV (SEQ ID NO: 1). According to another embodiment, the amino acid sequence of isolated JM-4 comprises a sequence at least 98% identical to amino acid sequence: GCAEHCSLNENITVPDTKV (SEQ ID NO: 1). According to another embodiment, the amino acid sequence of isolated JM-4 comprises a sequence at least 99% identical to amino acid sequence: GCAEHCSLNENITVPDTKV (SEQ ID NO: 1).

According to another embodiment, the at least one isolated erythropoietin (EPO)-derived oligopeptide is a stabilized isolated erythropoietin (EPO)-derived oligopeptide, wherein the stabilized isolated erythropoietin (EPO)-derived oligopeptide comprises at least one small bicyclic (meaning containing two fused rings) compound added to either an N-terminal end or a C-terminal end of the isolated erythropoietin (EPO)-derived oligopeptide.

According to another embodiment, the at least one small bicyclic molecule is biotin According to some such embodiments, administering step (b) occurs within about 15 minutes after the traumatic brain injury. According to another embodiment, administering step (b) occurs within about 1 hour after the traumatic brain injury. According to another embodiment, administering step (b) occurs within about 2 hours after the traumatic brain injury. According to another embodiment, administering step (b) occurs within about 3 hours after the traumatic brain injury. According to another embodiment, administering step (b) occurs within about 4 hours after the traumatic brain injury. According to another embodiment, administering step (b) occurs within about 5 hours after the traumatic brain injury. According to another embodiment, administering step (b) occurs within about 6 hours after the traumatic brain injury. According to another embodiment, administering step (b) occurs within about 7 hours after the traumatic brain injury. According to another embodiment, administering step (b) occurs within about 8 hours after the traumatic brain injury. According to another embodiment, administering step (b) occurs within about 9 hours after the traumatic brain injury. According to another embodiment, administering step (b) occurs within about 10 hours after the traumatic brain injury. According to another embodiment, administering step (b) occurs within about 11 hours after the traumatic brain injury. According to another embodiment, administering step (b) occurs within about 12 hours after the traumatic brain injury. According to another embodiment, administering step (b) occurs within about 13 hours after the traumatic brain injury. According to another embodiment, administering step (b) occurs within about 14 hours after the traumatic brain injury. According to another embodiment, step (b) administering a therapeutically effective amount after the pharmaceutical composition after step (a) to the subject in need thereof, occurs within about 15 hours after a traumatic brain injury. According to another embodiment, administering step (b) occurs within about 16 hours after the traumatic brain injury. According to another embodiment, administering step (b) occurs within about 17 hours after the traumatic brain injury. According to another embodiment, step (b) administering a therapeutically effective amount of the pharmaceutical composition of step (a) to the subject in need thereof, occurs within about 18 hours after a traumatic brain injury. According to another embodiment, administering step (b) occurs within about 19 hours after the traumatic brain injury. According to another embodiment, administering step (b) occurs within about 20 hours after the traumatic brain injury. According to another embodiment, administering step (b) occurs within about 21 hours after the traumatic brain injury. According to another embodiment, administering step (b) occurs within about 22 hours after the traumatic brain injury.

According to another embodiment, administering step (b) occurs within about 23 hours after the traumatic brain injury. According to another embodiment, administering step (b) occurs within about 24 hours after the traumatic brain injury.

According to some embodiments, administering step (b) occurs after the subject exhibits at least one symptom of traumatic brain injury. Symptoms of traumatic brain injury include, without limitation, headaches, neck pain, confusion, difficulty remembering, concentrating, or making decisions, dizziness, fatigue, mood changes, nausea, irritability, photophobia, blurred vision, ringing in the ears, loss of sense of taste or smell, seizures, sleep disturbances, hypoxemia, hypotension and brain swelling; coma, weakness, and paralysis. Traumatic brain injury may lead to a progressive decline in neurologic function that continue to evolve for months after the injury.

According to some embodiments, administration of the pharmaceutical composition treats at least one symptom of the traumatic brain injury (TBI). According to some such embodiments, the symptom of the traumatic brain injury is a headache. According to some such embodiments, the symptom of the traumatic brain injury is hypotension. According to some such embodiments, the symptom of the traumatic brain injury is hypoxemia. According to some such embodiments, the symptom of the traumatic brain injury is brain swelling. According to some such embodiments, the symptom of the traumatic brain injury is neck pain. According to some such embodiments, the symptom of the traumatic brain injury is difficulty remembering. According to some such embodiments, the symptom of the traumatic brain injury is difficulty concentrating. According to some such embodiments, the symptom of the traumatic brain injury is difficulty making decisions. According to some such embodiments, the symptom of the traumatic brain injury is fatigue. According to some such embodiments, the symptom of the traumatic brain injury is mood changes. According to some such embodiments, the symptom of the traumatic brain injury is nausea. According to some such embodiments, the symptom of the traumatic brain injury is photophobia. According to some such embodiments, the symptom of the traumatic brain injury is blurred vision. According to some such embodiments, the symptom of the traumatic brain injury is ringing in the ears. According to some such embodiments, the symptom of the traumatic brain injury is loss of sense of taste or smell.

According to another embodiment, treating step (c) further comprises reducing infiltration of a population of a mononuclear cell into the brain of the subject.

According to another embodiment, treating step (c) further comprises reducing axonal damage in at least one region of the brain of the subject affected by the traumatic brain injury.

According to another embodiment, treating step (c) further comprises reducing neuronal cell death in at least one region of the brain of the subject affected by the traumatic brain injury. According to another embodiment, treating step (c) further comprises reducing glial cell death in at least one region of the brain of the subject affected by the traumatic brain injury. According to another embodiment, treating step (c) further comprises reducing neuronal and glial cell death in at least one region of the brain of the subject affected by the traumatic brain injury.

According to another embodiment, treating step (c) further comprises improving a neurological deficit.

According to another embodiment, the therapeutically effective amount of the at least one isolated erythropoietin (EPO)-derived oligopeptide is from about 0.000001 mg/kg body weight to about 10 g/kg body weight. According to another embodiment, the therapeutically effective amount is from about 0.000002 mg/kg body weight to about 10 g/kg body weight. According to another embodiment, the therapeutically effective amount is from about 0.000003 mg/kg body weight to about 10 g/kg body weight. According to another embodiment, the therapeutically effective amount is from about 0.000004 mg/kg body weight to about 10 g/kg body weight. According to another embodiment, the therapeutically effective amount is from about 0.000005 mg/kg body weight to about 10 g/kg body weight. According to another embodiment, the therapeutically effective amount is from about 0.000006 mg/kg body weight to about 10 g/kg body weight. According to another embodiment, the therapeutically effective amount is from about 0.000007 mg/kg body weight to about 10 g/kg body weight. According to another embodiment, the therapeutically effective amount is from about 0.000008 mg/kg body weight to about 10 g/kg body weight. According to another embodiment, the therapeutically effective amount is from about 0.000009 mg/kg body weight to about 10 g/kg body weight. According to another embodiment, the therapeutically effective amount is from about 0.00001 mg/kg body weight to about 10 g/kg body weight. According to another embodiment, the therapeutically effective amount is from about 0.00002 mg/kg body weight to about 10 g/kg body weight. According to another embodiment, the therapeutically effective amount is from about 0.0003 mg/kg body weight to about 10 g/kg body weight. According to another embodiment, the therapeutically effective amount is from about 0.00004 mg/kg body weight to about 10 g/kg body weight. According to another embodiment, the therapeutically effective amount is from about 0.00005 mg/kg body weight to about 10 g/kg body weight. According to another embodiment, the therapeutically effective amount is from about 0.00006 mg/kg body weight to about 10 g/kg body weight. According to another embodiment, the therapeutically effective amount is from about 0.00007 mg/kg body weight to about 10 g/kg body weight. According to another embodiment, the therapeutically effective amount is from about 0.00008 mg/kg body weight to about 10 g/kg body weight. According to another embodiment, the therapeutically effective amount is from about 0.00009 mg/kg body weight to about 10 g/kg body weight. According to another embodiment, the therapeutically effective amount is from about 0.0001 mg/kg body weight to about 10 g/kg body weight. According to some such embodiments, the therapeutically effective amount is about 0.0005 mg/kg body weight. According to some such embodiments, the therapeutically effective amount is about 0.001 mg/kg body weight. According to some such embodiments, the therapeutically effective amount is about 0.005 mg/kg body weight. According to some such embodiments, the therapeutically effective amount is about 0.01 mg/kg body weight. According to some such embodiment, the therapeutically effective amount is about 0.1 mg/kg body weight. According to some such embodiments, the therapeutically effective amount is about 1 mg/kg body weight. According to some such embodiments, the therapeutically effective amount is about 10 mg/kg body weight. According to some such embodiments, the therapeutically effective amount is about 20 mg/kg body weight. According to some such embodiments, the therapeutically effective amount is about 30 mg/kg body weight. According to some such embodiments, the therapeutically effective amount is about 40 mg/kg body weight. According to some such embodiments, the therapeutically effective amount is about 50 mg/kg body weight. According to some such embodiments, the therapeutically effective amount is about 60 mg/kg body weight. According to some such embodiments, the therapeutically effective amount is about 70 mg/kg body weight. According to some such embodiments, the therapeutically effective amount about 80 mg/kg body weight. According to some such embodiments, the therapeutically effective amount is about 90 mg/kg body weight. According to some such embodiments, the therapeutically effective amount is about 100 mg/kg body weight. According to some such embodiments, the therapeutically effective amount is about 110 mg/kg body weight. According to some such embodiments, the therapeutically effective amount is about 120 mg/kg body weight. According to some such embodiments, the therapeutically effective amount is about 130 mg/kg body weight. According to some such embodiments, the therapeutically effective amount is about 140 mg/kg body weight. According to some such embodiments, the therapeutically effective amount is about 150 mg/kg body weight. According to some such embodiments, the therapeutically effective amount is about 160 mg/kg body weight. According to some such embodiments, the therapeutically effective amount is about 170 mg/kg body weight. According to some such embodiments, the therapeutically effective amount is about 180 mg/kg body weight. According to some such embodiments, the therapeutically effective is about 190 mg/kg body weight. According to some such embodiments, the therapeutically effective amount is about 200 mg/kg body weight. According to some such embodiments, the therapeutically effective amount is about 250 mg/kg body weight. According to some such embodiments, the therapeutically effective amount is about 500 mg/kg body weight.

According to some embodiments, the red blood cell indices comprise a hematocrit and the hematocrit is maintained at a stable level. According to some such embodiments, the hematocrit is maintained within about 20% of a reference value or baseline level. According to some such embodiments, the hematocrit is maintained within about 5% of a reference value or baseline level. According to some such embodiments, the hematocrit is maintained within about 6% of a reference value or baseline level. According to some such embodiments, the hematocrit is maintained within about 7% of a reference value or baseline level. According to some such embodiments, the hematocrit is maintained within about 8% of a reference value or baseline level. According to some such embodiments, the hematocrit is maintained within about 9% of a reference value or baseline level. According to some such embodiments, the hematocrit is maintained within 10% of a reference value or baseline level. According to some such embodiments, the hematocrit is maintained within about 11% of a reference value or baseline level. According to some such embodiments, the hematocrit is maintained within about 12% of a reference value or baseline level. According to some such embodiments, the hematocrit is maintained within about 13% of a reference value or baseline level. According to some such embodiments, the hematocrit is maintained within about 14% of a reference value or baseline level. According to some such embodiments, the hematocrit is maintained within 15% of a reference value or baseline level. According to some such embodiments, the hematocrit is maintained within 16% of a reference value or baseline level. According to some such embodiments, the hematocrit is maintained within 17% of a reference value or baseline level. According to some such embodiments, the hematocrit is maintained within 18% of a reference value or baseline level. According to some such embodiments, the hematocrit is maintained within 19% of a reference value or baseline level. According to some such embodiments the hematocrit is maintained within 20% of a reference value or baseline level.

According to another embodiment, the pharmaceutical composition further comprises at least one additional active ingredient.

According to another embodiment, the pharmaceutical composition further comprises at least one additional active ingredient. Examples of the active ingredient include, but are not limited to, an antibiotic agent, an antifungal agent, an antiviral agent, an antiprotozoal agent, an anesthetic agent, a steroidal anti-inflammatory agent, a non-steroidal anti-inflammatory agent, an antipruritic agent, an anti-oxidant agent, a chemotherapeutic agent, an anti-histamine agent, a vitamin, a hormone, a cytokine, or a cytokine antagonist.

According to another embodiment of the method, the isolated erythropoietin (EPO)-derived oligopeptide of the pharmaceutical composition, once administered, contacts at least one cell population that does not express erythropoietin receptor (EpoR)

According to another embodiment, the at least one cell population is a dendritic cell population. According to another embodiment, the at least one cell population is a T cell population.

3. Methods for Treating an Inflammatory Brain Disease

According to another aspect, the described invention provides a method for treating an inflammatory brain disease, disorder, or condition in a subject in need thereof, the method comprising steps:

(a) providing a pharmaceutical composition comprising:
(i) a therapeutically effective amount of at least one isolated erythropoietin (EPO)-derived oligopeptide; and
(ii) a pharmaceutically acceptable carrier;
(b) administering the therapeutically effective amount of the pharmaceutical composition of (a) to the subject in need thereof;
(c) treating a symptom of the inflammatory brain disease, disorder or condition; and
(d) maintaining red blood cell indices of the subject at substantially normal levels during treatment.

According to some embodiments of the method, the at least one isolated erythropoietin (EPO)-derived oligopeptide is a cyclic peptide. According to some such embodiments, the cyclic peptide is JM-4 (SEQ ID NO: 1). According to some such embodiments, the cyclic peptide is JM-5 (SEQ ID NO: 9). According to some such embodiments, the cyclic peptide is JM-7 (SEQ ID NO: 11).

According to another embodiment, the isolated erythropoietin (EPO)-derived peptide is JM-4 having amino acid sequence GCAEHCSLNENITVPDTKV (SEQ ID NO: 1). According to another embodiment, the amino acid sequence of isolated JM-4 comprises a sequence having substantial amino acid sequence identity to amino acid sequence: GCAEHCSLNENITVPDTKV (SEQ ID NO: 1). According to another embodiment, the amino acid sequence of isolated JM-4 comprises a sequence at least 90% identical to amino acid sequence: GCAEHCSLNENITVPDTKV (SEQ ID NO: 1). According to another embodiment, the amino acid sequence of isolated JM-4 comprises a sequence at least 91% identical to amino acid sequence: GCAEHCSLNENITVPDTKV (SEQ ID NO: 1). According to another embodiment, the amino acid sequence of isolated JM-4 comprises a sequence at least 92% identical to amino acid sequence: GCAEHCSLNENITVPDTKV (SEQ ID NO: 1). According to another embodiment, the amino acid sequence of isolated JM-4 comprises a sequence at least 93% identical to amino acid sequence: GCAEHCSLNENITVPDTKV (SEQ ID NO: 1). According to another embodiment, the amino acid sequence of isolated JM-4 comprises a sequence at least 94% identical to amino acid sequence: GCAEHCSLNENITVP- DTKV (SEQ ID NO: 1). According to another embodiment, the amino acid sequence of isolated JM-4 comprises a sequence at least 96% identical to amino acid sequence: GCAEHCSLNENITVPDTKV (SEQ ID NO: 1). According to another embodiment, the amino acid sequence of isolated JM-4 comprises a sequence at least 97% identical to amino acid sequence: GCAEHCSLNENITVPDTKV (SEQ ID NO: 1). According to another embodiment, the amino acid sequence of isolated JM-4 comprises a sequence at least 98% identical to amino acid sequence: GCAEHCSLNENITVPDTKV (SEQ ID NO: 1). According to another embodiment, the amino acid sequence of isolated JM-4 comprises a sequence at least 99% identical to amino acid sequence: GCAEHCSLNENITVPDTKV (SEQ ID NO: 1).

According to another embodiment, the isolated erythropoietin (EPO)-derived oligopeptide is a stabilized isolated erythropoietin (EPO)-derived oligopeptide, wherein the stabilized isolated erythropoietin (EPO)-derived oligopeptide comprises at least one small bicyclic (meaning containing two fused rings) compound added to either an N-terminal end or a C-terminal end of the isolated erythropoietin (EPO)-derived oligopeptide.

According to another embodiment, the at least one small bicyclic molecule is biotin.

According to some embodiments, the inflammatory brain disease is multiple sclerosis.

According to some embodiments, the inflammatory brain disease is a demyelinating disease.

According to some embodiments, the inflammatory brain disease is a chronic inflammatory brain disease, such as, neurodegenerative disease, including, but not limited to, Alzheimer's disease (AD), Parkinson's disease (PD), Huntington's disease, amyotrophic lateral sclerosis (ALS), and age-related macular degeneration (ARMD).

According to some embodiments, the inflammatory brain disease is a complication following a traumatic brain injury (TBI). According to some such embodiments, administering step (b) occurs within about 15 minutes after the traumatic brain injury. According to another embodiment, administering step (b) occurs within about 1 hour after the traumatic brain injury. According to another embodiment, administering step (b) occurs within about 2 hours after the traumatic brain injury. According to another embodiment, administering step (b) occurs within about 3 hours after the traumatic brain injury. According to another embodiment, administering step (b) occurs within about 4 hours after the traumatic brain injury. According to another embodiment, administering step (b) occurs within about 5 hours after the traumatic brain injury. According to another embodiment, administering step (b) occurs within about 6 hours after the traumatic brain injury. According to another embodiment, administering step (b) occurs within about 7 hours after the traumatic brain injury. According to another embodiment, administering step (b) occurs within about 8 hours after the traumatic brain injury. According to another embodiment, administering step (b) occurs within about 9 hours after the traumatic brain injury. According to another embodiment, administering step (b) occurs within about 10 hours after the traumatic brain injury. According to another embodiment, administering step (b) occurs within about 11 hours after the traumatic brain injury. According to another embodiment, administering step (b) occurs within about 12 hours after the traumatic brain injury. According to another embodiment, administering step (b) occurs within about 13 hours after the traumatic brain injury. According to another embodiment, administering step (b) occurs within about 14 hours after the traumatic brain injury. According to another embodiment, step (b) administering a therapeutically effective amount after the pharmaceutical composition after step (a) to the subject in need thereof, occurs within about 15 hours after a traumatic brain injury. According to another embodiment, administering step (b) occurs within about 16 hours after the traumatic brain injury. According to another embodiment, administering step (b) occurs within about 17 hours after the traumatic brain injury. According to another embodiment, step (b) administering a therapeutically effective amount of the pharmaceutical composition of step (a) to the subject in need thereof, occurs within about 18 hours after a traumatic brain injury. According to another embodiment, administering step (b) occurs within about 19 hours after the traumatic brain injury. According to another embodiment, administering step (b) occurs within about 20 hours after the traumatic brain injury. According to another embodiment, administering step (b) occurs within about 21 hours after the traumatic brain injury. According to another embodiment, administering step (b) occurs within about 22 hours after the traumatic brain injury. According to another embodiment, administering step (b) occurs within about 23 hours after the traumatic brain injury. According to another embodiment, administering step (b) occurs within about 24 hours after the traumatic brain injury.

According to some embodiments, administering step (b) occurs after the subject exhibits at least one symptom of traumatic brain injury. Symptoms of traumatic brain injury include, without limitation, headaches, neck pain, confusion, difficulty remembering, concentrating, or making decisions, dizziness, fatigue, mood changes, nausea, irritability, photophobia, blurred vision, ringing in the ears, loss of sense of taste or smell, seizures, sleep disturbances, hypoxemia, hypotension and brain swelling; coma, weakness, and paralysis. Traumatic brain injury may lead to a progressive decline in neurologic function that continue to evolve for months after the injury.

According to some embodiments, administration of the pharmaceutical composition treats at least one symptom of the traumatic brain injury (TBI). According to some such embodiments, the symptom of the traumatic brain injury is a headache. According to some such embodiments, the symptom of the traumatic brain injury is hypotension. According to some such embodiments, the symptom of the traumatic brain injury is hypoxemia. According to some such embodiments, the symptom of the traumatic brain injury is brain swelling. According to some such embodiments, the symptom of the traumatic brain injury is neck pain. According to some such embodiments, the symptom of the traumatic brain injury is difficulty remembering. According to some such embodiments, the symptom of the traumatic brain injury is difficulty concentrating. According to some such embodiments, the symptom of the traumatic brain injury is difficulty making decisions. According to some such embodiments, the symptom of the traumatic brain injury is fatigue. According to some such embodiments, the symptom of the traumatic brain injury is mood changes. According to some such embodiments, the symptom of the traumatic brain injury is nausea. According to some such embodiments, the symptom of the traumatic brain injury is photophobia. According to some such embodiments, the symptom of the traumatic brain injury is blurred vision. According to some such embodiments, the symptom of the traumatic brain injury is ringing in the ears. According to some such embodiments, the symptom of the traumatic brain injury is loss of sense of taste or smell. According to some such embodiments, the symptom of the traumatic brain injury is seizures. According to some such embodiments, the symptom of the traumatic brain injury is coma. According to some such embodiments, the symptom of the traumatic brain injury is muscle weakness. According to some such embodiments, the symptom of the traumatic brain injury is paralysis. According to some such embodiments, the symptom of the traumatic brain injury is a progressive decline in neurologic function following the traumatic brain injury.

According to one such embodiment, administering step (b) occurs within about 15 hours after the subject exhibits at least one symptom of traumatic brain injury. According to another embodiment, administering step (b) occurs within about 1 hour after the subject exhibits at least one symptom of traumatic brain injury. According to another embodiment, administering step (b) occurs within about 2 hours after the subject exhibits at least one symptom of traumatic brain injury. According to another embodiment, administering step (b) occurs within about 3 hours after the subject exhibits at least one symptom of traumatic brain injury. According to another embodiment, administering step (b) occurs within about 4 hours after the subject exhibits at least one symptom of traumatic brain injury. According to another embodiment, administering step (b) occurs within about 5 hours after the subject exhibits at least one symptom of traumatic brain injury. According to another embodiment, administering step (b) occurs within about 6 hours after the subject exhibits at least one symptom of traumatic brain injury. According to another embodiment, administering step (b) occurs within about 7 hours after the subject exhibits at least one symptom of traumatic brain injury. According to another embodiment, administering step (b) occurs within about 8 hours after the subject exhibits at least one symptom of traumatic brain injury. According to another embodiment, administering step (b) occurs within about 9 hours after the subject exhibits at least one symptom of traumatic brain injury. According to another embodiment, administering step (b) occurs within about 10 hours after the subject exhibits at least one symptom of traumatic brain injury. According to another embodiment, administering step (b) occurs within about 11 hours after the traumatic brain injury. According to another embodiment, administering step (b) occurs within about 12 hours after the subject exhibits at least one symptom of traumatic brain injury. According to another embodiment, administering step (b) occurs within about 13 hours after the traumatic brain injury. According to another embodiment, administering step (b) occurs within about 14 hours after the subject exhibits at least one symptom of traumatic brain injury. According to another embodiment, step (b) administering a therapeutically effective amount after the pharmaceutical composition after step (a) to the subject in need thereof, occurs within about 15 hours after the subject exhibits at least one symptom of traumatic brain injury. According to another embodiment, administering step (b) occurs within about 16 hours after the subject exhibits at least one symptom of traumatic brain injury. According to another embodiment, administering step (b) occurs within about 17 hours after the subject exhibits at least one symptom of traumatic brain injury. According to another embodiment, step (b) administering a therapeutically effective amount of the pharmaceutical composition of step (a) to the subject in need thereof, occurs within about 18 hours after the subject exhibits at least one symptom of a traumatic brain injury. According to another embodiment, administering step (b) occurs within about 19 hours after the traumatic brain injury. According to another embodiment, administering step (b) occurs within about 20 hours after the subject exhibits at least one symptom of traumatic brain injury. According to another embodiment, administering step (b) occurs within about 21 hours after the subject exhibits at least one symptom of traumatic brain injury. According to another embodiment, administering step (b) occurs within about 22 hours after the subject exhibits at least one symptom of traumatic brain injury. According to another embodiment, administering step (b) occurs within about 23 hours after the subject exhibits at least one symptom of traumatic brain injury. According to another embodiment, administering step (b) occurs within about 24 hours after the subject exhibits at least one symptom of traumatic brain injury.

According to another embodiment, treating step (c) further comprises reducing infiltration of a population of a mononuclear cell into the brain of the subject.

According to another embodiment, treating step (c) further comprises reducing axonal damage in at least one region of the brain of the subject affected by the inflammatory disease, disorder or condition.

According to another embodiment, treating step (c) further comprises reducing neuronal cell death in at least one region of the brain of the subject affected, directly or indirectly, by the inflammatory disease, disorder or condition. According to another embodiment, treating step (c) further comprises reducing glial cell death in at least one region of the brain of the subject affected, directly or indirectly, by the inflammatory disease, disorder or condition. According to another embodiment, treating step (c) further comprises reducing neuronal and glial cell death in at least one region of the brain of the subject affected, directly or indirectly, by the inflammatory disease, disorder or condition.

According to another embodiment, treating step (c) further comprises improving a neurological deficit.

According to another embodiment, the therapeutically effective amount of the at least one isolated erythropoietin (EPO)-derived oligopeptide is from about 0.000001 mg/kg body weight to about 10 g/kg body weight. According to another embodiment, the therapeutically effective amount is from about 0.000002 mg/kg body weight to about 10 g/kg body weight. According to another embodiment, the therapeutically effective amount is from about 0.000003 mg/kg body weight to about 10 g/kg body weight. According to another embodiment, the therapeutically effective amount is from about 0.000004 mg/kg body weight to about 10 g/kg body weight. According to another embodiment, the therapeutically effective amount is from about 0.000005 mg/kg body weight to about 10 g/kg body weight. According to another embodiment, the therapeutically effective amount is from about 0.000006 mg/kg body weight to about 10 g/kg body weight. According to another embodiment, the therapeutically effective amount is from about 0.000007 mg/kg body weight to about 10 g/kg body weight. According to another embodiment, the therapeutically effective amount is from about 0.000008 mg/kg body weight to about 10 g/kg body weight. According to another embodiment, the therapeutically effective amount is from about 0.000009 mg/kg body weight to about 10 g/kg body weight. According to another embodiment, the therapeutically effective amount is from about 0.00001 mg/kg body weight to about 10 g/kg body weight. According to another embodiment, the therapeutically effective amount is from about 0.00002 mg/kg body weight to about 10 g/kg body weight. According to another embodiment, the therapeutically effective amount is from about 0.0003 mg/kg body weight to about 10 g/kg body weight. According to another embodiment, the therapeutically effective amount is from about 0.00004 mg/kg body weight to about 10 g/kg body weight. According to another embodiment, the therapeutically effective amount is from about 0.00005 mg/kg body weight to about 10 g/kg body weight. According to another embodiment, the therapeutically effective amount is from about 0.00006 mg/kg body weight to about 10 g/kg body weight. According to another embodiment, the therapeutically effective amount is from about 0.00007 mg/kg body weight to about 10 g/kg body weight. According to another embodiment, the therapeutically effective amount is from about 0.00008 mg/kg body weight to about 10 g/kg body weight. According to another embodiment, the therapeutically effective amount is from about 0.00009 mg/kg body weight to about 10 g/kg body weight. According to another embodiment, the therapeutically effective amount is from about 0.0001 mg/kg body weight to about 10 g/kg body weight. According to some such embodiments, the therapeutically effective amount is about 0.0005 mg/kg body weight. According to some such embodiments, the therapeutically effective amount is about 0.001 mg/kg body weight. According to some such embodiments, the therapeutically effective amount is about 0.005 mg/kg body weight. According to some such embodiments, the therapeutically effective amount is about 0.01 mg/kg body weight. According to some such embodiment, the therapeutically effective amount is about 0.1 mg/kg body weight. According to some such embodiments, the therapeutically effective amount is about 1 mg/kg body weight. According to some such embodiments, the therapeutically effective amount is about 10 mg/kg body weight. According to some such embodiments, the therapeutically effective amount is about 20 mg/kg body weight. According to some such embodiments, the therapeutically effective amount is about 30 mg/kg body weight. According to some such embodiments, the therapeutically effective amount is about 40 mg/kg body weight. According to some such embodiments, the therapeutically effective amount is about 50 mg/kg body weight. According to some such embodiments, the therapeutically effective amount is about 60 mg/kg body weight. According to some such embodiments, the therapeutically effective amount is about 70 mg/kg body weight. According to some such embodiments, the therapeutically effective amount about 80 mg/kg body weight. According to some such embodiments, the therapeutically effective amount is about 90 mg/kg body weight. According to some such embodiments, the therapeutically effective amount is about 100 mg/kg body weight. According to some such embodiments, the therapeutically effective amount is about 110 mg/kg body weight. According to some such embodiments, the therapeutically effective amount is about 120 mg/kg body weight. According to some such embodiments, the therapeutically effective amount is about 130 mg/kg body weight. According to some such embodiments, the therapeutically effective amount is about 140 mg/kg body weight. According to some such embodiments, the therapeutically effective amount is about 150 mg/kg body weight. According to some such embodiments, the therapeutically effective amount is about 160 mg/kg body weight. According to some such embodiments, the therapeutically effective amount is about 170 mg/kg body weight. According to some such embodiments, the therapeutically effective amount is about 180 mg/kg body weight. According to some such embodiments, the therapeutically effective is about 190 mg/kg body weight. According to some such embodiments, the therapeutically effective amount is about 200 mg/kg body weight. According to some such embodiments, the therapeutically effective amount is about 250 mg/kg body weight. According to some such embodiments, the therapeutically effective amount is about 500 mg/kg body weight.

According to some embodiments, the red blood cell indices comprise a hematocrit and the hematocrit is maintained at a stable level. According to some such embodiments, the hematocrit is maintained within about 20% of a reference value or baseline level. According to some such embodiments, the hematocrit is maintained within about 5% of a reference value or baseline level. According to some such embodiments, the hematocrit is maintained within about 6% of a reference value or baseline level. According to some such embodiments, the hematocrit is maintained within about 7% of a reference value or baseline level. According to some such embodiments, the hematocrit is maintained within about 8% of a reference value or baseline level. According to some such embodiments, the hematocrit is maintained within about 9% of a reference value or baseline level. According to some such embodiments, the hematocrit is maintained within 10% of a reference value or baseline level. According to some such embodiments, the hematocrit is maintained within about 11% of a reference value or baseline level. According to some such embodiments, the hematocrit is maintained within about 12% of a reference value or baseline level. According to some such embodiments, the hematocrit is maintained within about 13% of a reference value or baseline level. According to some such embodiments, the hematocrit is maintained within about 14% of a reference value or baseline level. According to some such embodiments, the hematocrit is maintained within 15% of a reference value or baseline level. According to some such embodiments, the hematocrit is maintained within 16% of a reference value or baseline level. According to some such embodiments, the hematocrit is maintained within 17% of a reference value or baseline level. According to some such embodiments, the hematocrit is maintained within 18% of a reference value or baseline level. According to some such embodiments, the hematocrit is maintained within 19% of a reference value or baseline level. According to some such embodiments the hematocrit is maintained within 20% of a reference value or baseline level.

According to another embodiment, the pharmaceutical composition further comprises at least one additional active ingredient. Examples of the active ingredient include, but are not limited to, an antibiotic agent, an antifungal agent, an antiviral agent, an antiprotozoal agent, an anesthetic agent, a steroidal anti-inflammatory agent, a non-steroidal anti-inflammatory agent, an antipruritic agent, an anti-oxidant agent, a chemotherapeutic agent, an anti-histamine agent, a vitamin, a hormone, a cytokine, or a cytokine antagonist.

According to another embodiment of the method, the isolated erythropoietin (EPO)-derived oligopeptide of the pharmaceutical composition, once administered, contacts at least one cell population that does not express erythropoietin receptor (EpoR). According to another embodiment, the at least one cell population is a dendritic cell population. According to another embodiment, the at least one cell population is a T cell population.

According to another embodiment, the isolated erythropoietin (EPO)-derived oligopeptide of the pharmaceutical composition, once administered, contacts at least one cell population at a site of traumatic intracerebral hemorrhage. According to another embodiment, the isolated erythropoietin (EPO)-derived oligopeptide of the pharmaceutical composition, once administered, contacts at least one cell population at a site of intraparenchymal bleeding.

The zone of dysfunctional neuronal/glial cells may extend beyond the site directly affected by the primary injury to include a variable boundary of adjacent normal appearing tissue. Progressive neurologic decline occurs as neuronal/glial cell death progresses into this region. According to another embodiment, the isolated erythropoietin (EPO)-derived oligopeptide of the pharmaceutical composition, once administered, contacts at least one cell population in the variable boundary of adjacent normal appearing tissue.

General methods in molecular genetics and genetic engineering useful in the present invention are described in the current editions of Molecular Cloning: A Laboratory Manual (Sambrook, et al., 1989, Cold Spring Harbor Laboratory Press), Gene Expression Technology (Methods in Enzymology, Vol. 185, edited by D. Goeddel, 1991. Academic Press, San Diego, Calif.), "Guide to Protein Purification" in Methods in Enzymology (M. P. Deutshcer, ed., (1990) Academic Press, Inc.); PCR Protocols: A Guide to Methods and Applications (Innis, et al. 1990. Academic Press, San Diego, Calif.), Culture of Animal Cells: A Manual of Basic Technique, 2nd Ed. (R. I. Freshney. 1987. Liss, Inc. New York, N.Y.), and Gene Transfer and Expression Protocols, pp. 109-128, ed. E. J. Murray, The Humana Press Inc., Clifton, N.J.). Reagents, cloning vectors, and kits for genetic manipulation are available from commercial vendors such as BioRad, Stratagene, Invitrogen, ClonTech and Sigma-Aldrich Co.

Where a value of ranges is provided, it is understood that each intervening value, to the tenth of the unit of the lower limit unless the context clearly dictates otherwise, between the upper and lower limit of that range and any other stated or intervening value in that stated range is encompassed within the invention. The upper and lower limits of these smaller ranges which may independently be included in the smaller ranges is also encompassed within the invention, subject to any specifically excluded limit in the stated range. Where the stated range includes one or both of the limits, ranges excluding either both of those included limits are also included in the invention.

Unless defined otherwise, all technical and scientific terms used herein have the same meaning as commonly understood by one of ordinary skill in the art to which this invention belongs. Although any methods and materials similar or equivalent to those described herein can also be used in the practice or testing of the present invention, the preferred methods and materials are now described. All publications mentioned herein are incorporated herein by reference to disclose and describe the methods and/or materials in connection with which the publications are cited.

It must be noted that as used herein and in the appended claims, the singular forms "a", "and" and "the" include plural references unless the context clearly dictates otherwise. All technical and scientific terms used herein have the same meaning Publications disclosed herein are provided solely for their disclosure prior to the filing date of the present invention. Nothing herein is to be construed as an admission that the present invention is not entitled to antedate such publication by virtue of prior invention. Further, the dates of publication provided may be different from the actual publication dates which may need to be independently confirmed.

EXAMPLES

The following examples are put forth so as to provide those of ordinary skill in the art with a complete disclosure and description of how to make and use the present invention, and are not intended to limit the scope of what the inventors regard as their invention nor are they intended to represent that the experiments below are all or the only experiments performed. Efforts have been made to ensure accuracy with respect to numbers used (e.g., amounts, temperature, etc.) but some experimental errors and deviations should be accounted for. Unless indicated otherwise, parts are parts by weight, molecular weight is weight average molecular weight, temperature is in degrees Centigrade, and pressure is at or near atmospheric.

Methods
1. Peptide Synthesis and Purification

Whole erythropoietin (EPO) molecule was purchased from a commercial vendor (Epoetin Alfa, Ortho Biotech products, L.P.) (2000 U/ml) and stored at 4° C. Peptide JM-4 (GCAEHCSLNENITVPDTKV; SEQ ID NO: 1) was prepared commercially (Invitrogen, Carlsbad, Calif.; UMDNJ Molecular Resource Facility, Piscataway, N.J.; and United Biochemical Research, Seattle, Wash.).

Short EPO peptides were synthesized using Fmoc solid phase chemistry and isolated by high performance liquid chromatography (HPLC) to 90% purity. Each purified peptide is shipped with an HPLC document, showing the level of purity, and with a mass spectral analysis. All peptides are lyophilized and sealed under argon to minimize any potential degradation.

The cyclic nature of JM-4 peptide was established by MALDI mass spectrometry. JM-4 peptide was dissolved in phosphate buffered saline (1×PBS, pH 7.4) (at 1 mg/ml) and stored at −20° C. until use.

2. Animals

Male C57BL/6 mice (8 to 10 weeks old; each 20 g to 25 g body weight) were purchased (Charles River Laboratories, Wilmington, Mass.) and maintained in a conventional facility. The studies were conducted in accordance with the Animal Component of Research Protocol guidelines at the Veterans Affairs Hospital, East Orange, N.J.

3. Controlled Cortical Impact Animal Model

C57BL/6 mice were anesthetized with isofurane/oxygen inhalation and placed in a stereotaxic frame. The head position was established in the horizontal plane and a craniotomy (4 mm) was produced lateral to the sagittal suture between lambda and bregma, with the dura mater left intact over the cortex. A cortical contusion injury was produced utilizing a pneumatically driven 2.5 mm diameter rod tip at 3.5 m/s to a depth of 1 mm with a dwell time of 400 ms (Precision System Instruments TBI-0300 Impactor, Lexington, Ky.). After injury, a 5 mm disk constructed from dental cement was placed over the craniotomy site and adhered to the skull using cyanocrylate. During the early post-operative phase, animal temperature was maintained by placing the animals on heating pads.

Sham-operated mice received a craniotomy but no cortical impact, and the skull was sealed with a dental cement plate. Mice were assigned to treatment groups post-surgery.

4. Administration of rhEPO and JM-4 Peptide

Mice in the whole molecule EPO group received 5000 U/kg body weight rhEPO (Epoetin alpha, Amgen, Thousand Oaks, Calif.) intraperitoneally (i.p.). JM-4 peptide (10 µg/animal) was administered intraperitoneally (i.p.). Mice in the PBS and sham-operated groups received 200 µl filtered sterile PBS.

5. Cryosectioning

Mice were sacrificed at 3 days or 8 days post-injury; brains were collected and immediately frozen on dry ice. The frozen brains were serially sectioned in coronal cuts onto 15 slides with 12 sections (16 µm thickness) per slide extending from the anterior to the posterior edge of the lesion. Sections were placed such that each individual slide contained a representative sampling of the entire lesion within the injured hemisphere.

6. Detection of Cell Death: In Situ TUNEL Staining

Terminal deoxynucleotidyl transferase dUTP nick end labeling (TUNEL) is a method for detecting DNA fragmentation by labeling the terminal end of nucleic acids and is a common method for detecting the DNA fragmentation that accomplishes both necrosis and cell death by the apoptotic signaling cascade. In addition, this technique can detect early-stage apoptosis in systems where chromatin condensation has begun and strand breaks are fewer, even before the nucleus undergoes major morphological changes. The assay relies on the presence of nicks in the DNA which can be identified by terminal deoxynucleotidyl transferase (Tdt, an enzyme that will catalyze the addition of dUTPs that are secondarily labeled with a marker). Briefly, DNA strand breaks generated upon DNA fragmentation that typically are localized in morphologically identifiable nuclei and apoptotic bodies are detected by enzymatically labeling the free 3'-OH termini with modified nucleotides. In contrast, normal or proliferative nuclei, which have relatively insignificant numbers of DNA 3'-OH ends, are not labeled. Drug-induced DNA damage is not identified by the TUNEL assay unless it is coupled to the apoptotic response.

Cell death in the mouse brains was detected using a modification of the Apoptag® (Millipore, Billerica, Mass.) in situ TUNEL method. Cryosections (16 μm thickness) were mounted and fixed in 100% acetone for 10 minutes. The slides were rehydrated and post-fixed in 2:1 ethanol:acetic acid for 11 minutes at −20° C., and then washed thoroughly in Stop/Wash Buffer (Apoptag®). Slides were incubated with equilibration buffer for 10 minutes immediately followed by working strength TdT enzyme (33 parts enzyme/77 parts buffer (Apoptag®)) for 60 minutes at 37° C. The TUNEL reaction was detected with Cy3 anti-digox (1:200; Jackson Immunoresearch, West Grove, Pa.). IgG antibody (1.7 mg/ml) was dissolved in distilled water (350 μl) and then diluted 1:200 with PBS.

Micrographs of the processed slides were acquired with a fluorescent Olympus BX60 microscope fitted with a Retiga 2000R digital camera at 10 times magnification. The total number of TUNEL positive cells in lesioned hemispheres and the total area of the brain containing the TUNEL positive cells were quantified using digital imaging software (I.P. lab 4.0, Becton Dickinson, Franklin Lakes, N.J.).

7. Statistical Analysis

Data (mean+SEM) between groups were compared by one-way analysis of variance (ANOVA) tests, followed by the Tukey test for the post hoc comparison of individual group means between PBS, rhEPO, and JM-4 peptide treated animals. One way ANOVA was used in the analysis of composite SNAP clinical scoring. A value of p<0.05 was considered as statistically significant.

Example 1

Experimental Autoimmune Encephalomyelitis (EAE)

Experimental autoimmune encepahlomyelitis (EAE) is an animal model of brain inflammation. EAE is an inflammatory demyelinating disease of the central nervous system (CNS) and is widely used as an animal model of human CNS demyelinating diseases.

An EAE model was established in strain SJL/J mice that is characterized by a relapsing-remitting clinical course. Briefly, mice were immunized subcutaneously at the tail base with 100 μl (200 μg) myelin oligodendrocyte glycoprotein (MOG) peptide dissolved in distilled water and emulsified with an equal volume of complete Freund's adjuvant supplemented with 4 mg/ml mycobacterium tuberculosis H37Ra. Immediately after immunization, animals received an intravenous injection of 200 ng bordetella pertussis toxin in 200 μl PBS. Animals were weighed daily and assessed for clinical signs of EAE by two independent observers.

Five mice per group were given either daily i.v. full length EPO (50-500 U/kg) or short EPO-peptide JM-4 peptide (250-500 μg/kg; 5-10 μg/mouse) in PBS, or PBS alone for 9 to 14 days. Blood was collected for 5 weeks to document changes in hematocrit.

Hematocrit can be determined by centrifuging heparinized blood in a capillary tube (microhematocrit tube) at 10,000 rpm for 5 minutes. This separates the blood into layers. The volume of packed red blood cells, divided by the total volume of the blood sample gives the packed cell volume (PCV). Because a tube is used, this can be calculated by measuring the lengths of the layers.

FIG. 1 shows a graph of the level of hematocrit (%) versus time (days) for mice treated with PBS, JM-1 peptide, JM-4 peptide, and rhEPO. The hematocrit in full-length EPO treated SJL/J mice increased markedly within one week of EPO injection and continued to rise up to 75% on day 14. The hematocrit in both PBS sham-treated and JM-4 peptide treated groups remained unaltered (51±1%) over a five week follow-up. No deaths or clinical morbidity occurred in the short EPO-peptide treated groups. Blood chemistries from a small group treated with JM-4 peptide for 7 days remained unaltered and with stable hematocrit levels.

Mice treated with rhEPO developed red-blue ears and tails within 5 to 6 days, typically leading to death (partially due to an increase in red blood cell mass). In contrast, JM-4 peptide has no effect on hematocrit in SJL/J mice. FIG. 1 further shows that both short EPO-derived JM-1 peptide and PBS treatments similarly have no affect on levels of hematocrit within SJL EAE mice. The following experiments were done only with JM-4.

Example 2

JM-4 Peptide Reduces SJL Mice EAE Clinical Deficit

Figure 2:
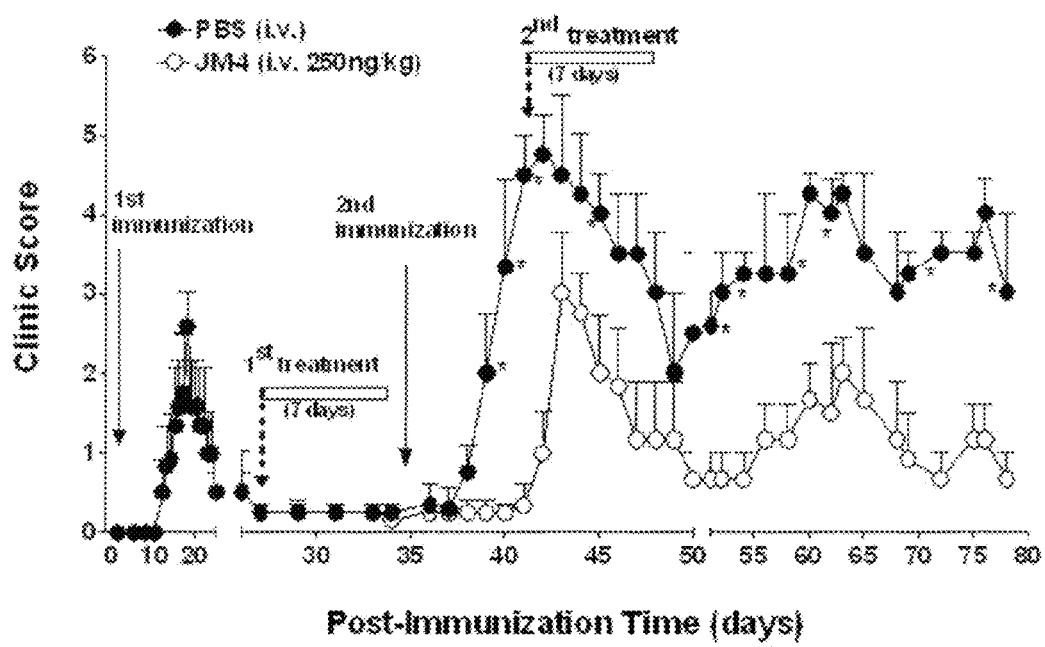
FIG. 2 shows a graph of clinical score in JM4 treated and sham treated versus time post-immunization with proteolipid protein (PLP) and adjuvant.

JM-4 peptide rapidly reduces neurologic deficit in EAE mice. FIG. 2 shows a graph of clinical score versus time post-immunization (days). Briefly, proteolipid (PLP) antigen immunization readily induced EAE in SJL/J mice and significant neurologic impairment occurred at about day 10 post-immunization. Mice first were immunized with a suboptimal dose of PLP antigen (100 μg) on day 0; the mice developed clinical deficits, and were allowed to recover for about 21 days. Recovered EAE mice received 7 days of treatment with either cyclic JM-4 peptide (i.v. 250 ng/kg) or PBS (i.v.) before receiving a second PLP antigen immunization (100 μg).

Marked clinical improvement was observed in JM-4 peptide treated EAE mice when compared to EAE animals sham treated with saline (p<0.05). JM-4 peptide treated animals developed less severe clinical signs at a later time in response to the second immunization compared to sham treated animals (p<0.05). Clinical improvement again was observed when the JM-4 peptide treated animals received a second seven-day treatment course with the JM-4 peptide compared to the PBS sham treated animals. Long term follow-up in EAE mice showed a relapsing-remitting disease course. The sham treated EAE mice continued to exhibit a more severe pattern of relapse, whereas EAE mice treated with JM-4 peptide had much milder disease after discontinuation of all therapy for 30 days (p<0.001). No alteration in hematocrit was induced by JM-4 peptide therapy, nor were any signs of toxicity observed in contrast to therapy with whole EPO.

Example 3

Effect of JM-4 Peptide Therapy on Acutely Symptomatic EAE Animals

The effect of JM-4 peptide therapy on acutely symptomatic EAE animals was studied. Five sham-treated animals with EAE were compared to five EAE animals that had received 4 days of therapy with JM-4 peptide. The sham-treated animals were barely capable of moving their heads with marked four limb weakness. The EAE animals treated with JM-4 peptide were mobile and markedly improved as compared to the sham-treated animals. The JM-4 peptide treated animals have some neurologic residua (they have a waddling gait and their tails drag).

Example 4

JM-4 Peptide Blocks CNS Inflammation and Induces Axonal Protection

Figure 3:
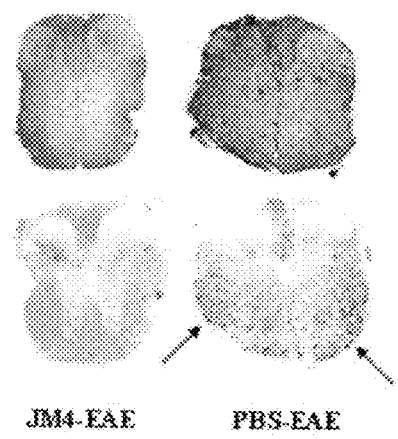
FIG. 3 shows micrographs of brain sections from SJL/EAE mice.

Groups of PLP antigen-induced symptomatic SJL/J EAE mice were treated with either JM-4 peptide or PBS for 7 days, and spinal cords were removed for pathologic examination. FIG. 3 shows micrographs of brain sections from the SJL/EAE mice. There was a marked reduction in white matter mononuclear infiltration and fewer vacuolar changes in mice treated with JM-4 peptide as compared to PBS treated controls (FIG. 3, top panel). MHC class II expression was markedly upregulated in both central gray and white matter of PBS treated EAE spinal cord compared to unaffected normal control cord (data not shown).

Monoclonal antibody (SMI-32) (Sternberger Monoclonal Antibodies, Lutherville, Md.) that reacts with a nonphosphorylated epitope in neurofilament H—was used. The reaction is masked when the epitope is phosphorylated. Briefly, frozen tissue sections (16 µm) were acetone-fixed for 10 minutes and air dried. Antigen retrieval was performed using 1× Target Unmasking Fluid (TUF) (Zymed Laboratories, San Francisco, Calif.). Slides were reacted with TUF at 95° C. for 10 minutes, then at room temperature (25° C.) for 10 minutes. SMI-32 primary antibody was diluted (1:5000) with 2% normal horse serum in PBS (1×) and reacted overnight at 4° C. Additional slides were processed without the primary antibody to provide an appropriate control. Slides then were washed twice with PBS (1×) for 3 minutes each wash, and reacted with a biotinylated anti-mouse antibody (Vector Laboratories, Burlingame, Calif.). The slides were washed twice (PBS (1×), 3 minutes each wash), reacted with an avidin-biotin/horseradish peroxidase complex (Vector Laboratories, Burlingame, Calif.) for 30 minutes at room temperature, and washed (PBS (1×), 3 minutes). Slides were visualized with Tyramide signal amplification/Cyanine-3 dye (Perkin Elmer, Waltham, Mass.) at 1:200 dilution in amplification buffer (Perkin Elmer, Waltham, Mass.). Slides then were mounted in glycerol and examined by fluorescence microscopy.

Acute axonal injury in spinal long tract was assessed by SMI-32 staining for nonphosphorylated neurofilaments (FIG. 3, black DAB staining, bottom 2 panels). Many injured SMI-32 positive axons were present in sham-treated EAE spinal cord (FIG. 3; bottom panel-right) whereas far fewer injured axons were present in JM-4 peptide treated EAE spinal cord (FIG. 3; bottom panel-left).

Example 5

Neuroprotection in Traumatic Brain Injury Using JM-4 Peptide

Groups of brain injured mice were treated i.p. within 30 minutes of trauma with whole molecule EPO (5000 U/kg), short EPO peptide JM-4 peptide (10 µg), or sham treated with saline (PBS) for 3 days. The animals were sacrificed after 3 or 8 days and the injured forebrain lesions were serially sectioned. Cell death within the damaged hemisphere was quantified by DNA fragmentation (TUNEL stain) to determine the degree of neuroprotection. Serial sections containing the entire lesion site and the TUNEL labeled peri-lesional zone were photographed, digitized, and the images used to quantify the number of positive cells by IP lab 4.0 Software (Becton Dickinson, Franklin Lakes, N.J.).

Figure 4:
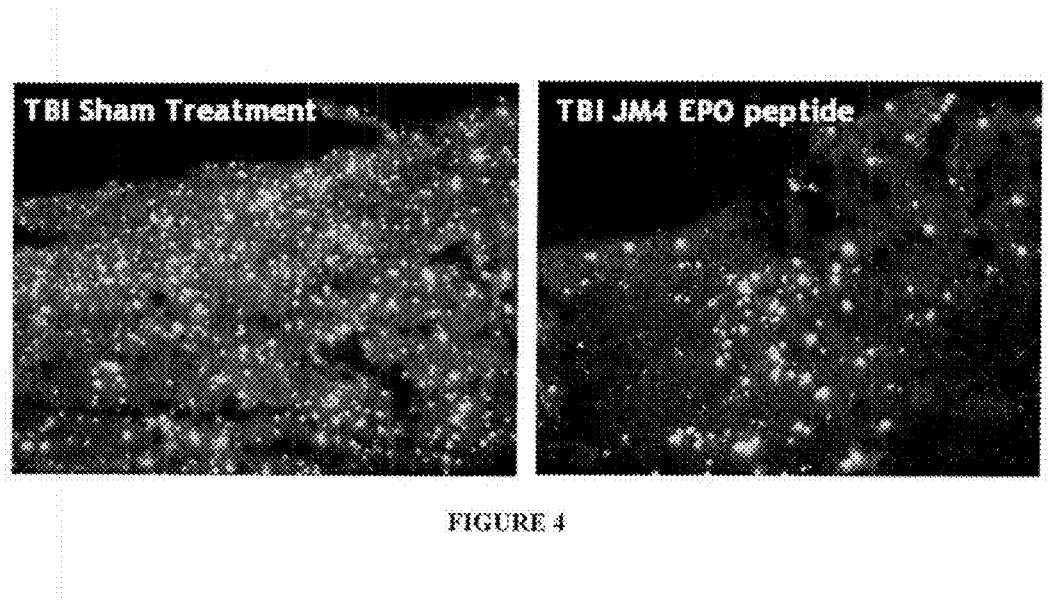
FIG. 4 shows representative low power illustrations of TUNEL stained cerebrum from a sham treated TBI animal versus the same area in an animal treated with small EPO peptide for 3 days after traumatic brain injury.
Figure 5A:
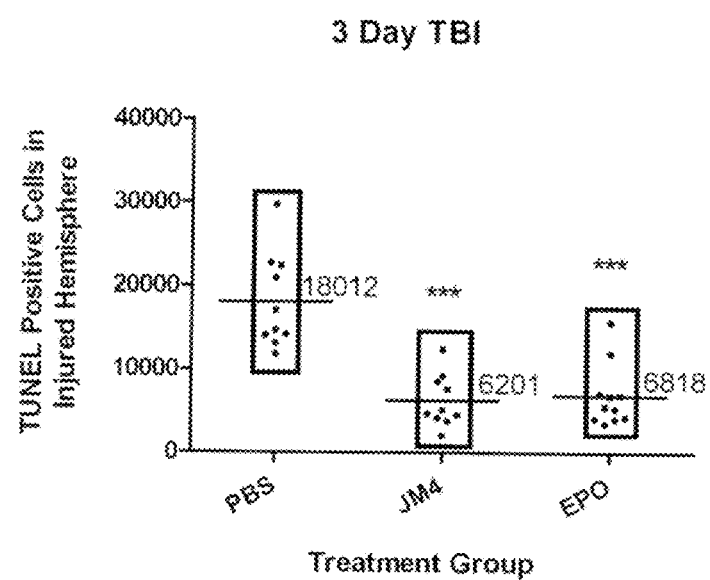
FIG. 5A shows a graph of TUNEL positive cell numbers in the injured hemisphere 3 days post treatment with PBS (n=10), JM-4 peptide (n=10) and EPO (n=10)
Figure 5B:
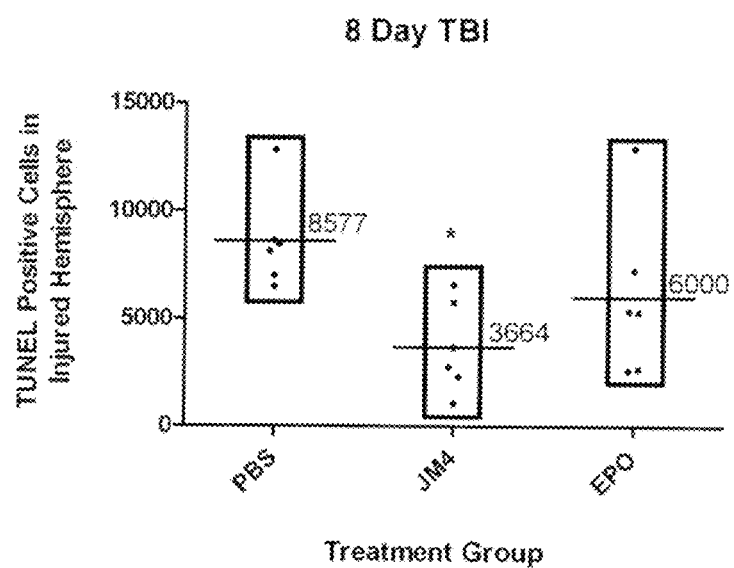
FIG. 5B shows a graph of TUNEL positive cells in the injured hemisphere 8 days post treatment with PBS (n=6), JM-4 peptide (n=6) and EPO (n=6).

FIG. 4 shows representative low power (40× magnification) illustrations of TUNEL stained cerebrum from a sham treated TBI animal versus the same area in an animal treated with JM-4 peptide for 3 days after injury. FIG. 5A shows a graph of TUNEL positive cells in the injured hemisphere 3 days post treatment after receiving either PBS (n=10), JM-4 peptide (n=10) and EPO (n=10); FIG. 5B shows a graph of TUNEL positive cells in the injured hemisphere 8 days post treatment with PBS (n=6), JM-4 peptide (n=6) and EPO (n=6). It is evident that there are far less TUNEL positive cells in the lesioned hemisphere of EPO peptide treated animals; the number of dying cells in the experimental groups was dramatically reduced in the treated arms (t test, $p<0.001$ and $p<0.01$) at both 3 and 8 days post injury.

The data in FIG. 5A shows that JM-4 peptide reduced neural cell death by nearly 70%. The lesional area containing TUNEL positive cells was much reduced at 3 days post-injury. Similarly, FIG. 5B shows by TUNEL that JM-4 is neuroprotective 8 days after treatment with JM-4.

These results therefore show that the neuroprotective effect of JM-4 peptide is not associated with any increase in red blood cell mass even when administered long term, and that JM-4 is at least as effective as using whole molecule EPO in blocking cell death.

Example 6

Effect of JM-4 Peptide Therapy on the Summed Area Containing TUNEL Positive Cells Within the Lesioned Hemisphere The effect of JM-4 peptide therapy on the summed area containing TUNEL positive cells within the lesioned hemisphere was evaluated 3 days post-injury. In this experiment, the same TUNEL stained sections (from Example 5) used to quantify the number of TUNEL positive cells were used to quantify the total area containing dying cells within the injured hemisphere. The digitized images containing TUNEL positive cells were manually traced and subsequently quantified using IP lab 4.0 software (Becton Dickinson, Franklin Lakes, N.J.).

Figure 6:
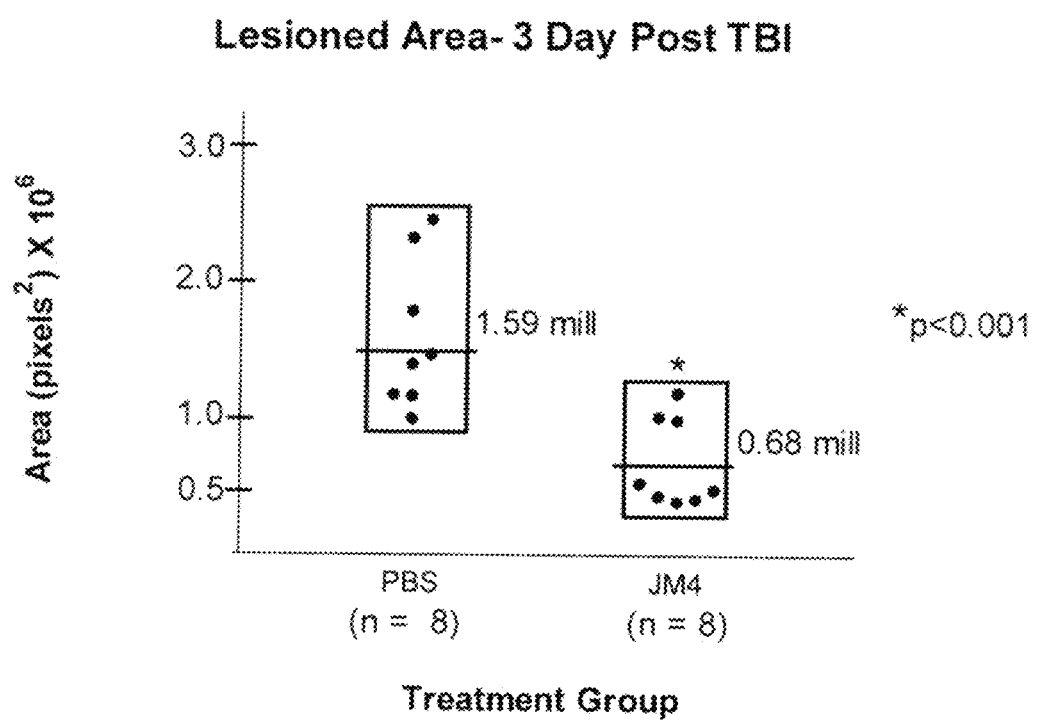
FIG. 6 shows a graph of lesioned area ((pixels$^2$)×10$^6$) of the PBS treatment group (n=8) versus JM-4 peptide treatment group (n=8).

FIG. 6 shows a graph of the lesioned area (($pixels^2$)×$10^6$) within the PBS treatment group (n=8) and JM-4 peptide treatment group (n=8). FIG. 6 shows that JM-4 peptide treated animals show a marked reduction (greater than 50%) of lesioned volume (area) (p<0.001).

Example 7

Simple Neuroassessment of Asymmetric Impairment (SNAP)

SNAP is a scoring system, based on six tests, developed and validated to assess neurological deficits induced in a mouse model of traumatic brain injury. Mice are evaluated to assess neurological parameters for: (1) interaction with a handler, (2) cage grasp, (3) visual placing, (4) pacing/circling, (5) posture and head tilt, and (6) the baton test. The results from each of the six tests are summed to derive the overall SNAP score. SNAP scores are high when asymmetric deficits are apparent; thus, a neurologically intact animal would be expected to have a SNAP score of "0." SNAP allows for ambiguous results (for example, a score of '1') and test scores of 2 to 5 are assigned when asymmetric deficits were apparent. In addition, a range is allowed when the deficit appears to span more than one definition for a test score; ranges then are averaged to derive the test score (for example, a range of 2 to 3 would be scored as 2.5 for that test).

7.1. Interaction with a Handler

Observations of the interaction of the mouse with the handler assess the animal's level of alertness and its integration of vision that is required escape the handler's hand. This interaction was tested upon removal of the mouse from the home cage. An alert active mouse that avoided handling was assigned a score of "0", whereas an injured mouse was expected to show impairment and respond slower. If a mouse froze before escaping and/or could be captured by the skin on its back, then it would receive a score of "2."

7.2. Cage Grasp

A cage grasp test was used to evaluate grip strength and paw symmetry. Briefly, a mouse was removed from its home cage, immediately suspended by the tail over the cage lid (metal bars, 1.5 mm diameter, 6 mm apart), and allowed to grasp a bar with both forepaws. The mouse then was slowly pulled away from the cage, and the paw which released first was observed. An injured mouse was expected to have a contralateral grip weakness; therefore, if the contralateral forepaw was the first to release greater than 50% of the observations, but less than 100% of the observations, the score would be "2."

7.3. Visual Placing

A visual placing test was utilized to evaluate vision, torso strength, forelimb coordination, proprioception, and tactile input. Briefly, a mouse was suspended by the tail and slowly advanced toward a countertop, or a ledge, level with its torso. An uninjured mouse extended its upper torso to simultaneously reach out toward the edge of the countertop with both forepaws. An injured mouse typically exhibited contralateral weakness in the paw as demonstrated by occasionally failing to reach with the contralateral paw (which may result from decreased contralateral vision, decreased proprioception and/or tactile input from the contralateral paw).

7.4. Pacing/Circling

The mouse was observed for pacing/circling in a test chamber (18 cm by 40 cm). An uninjured mouse would ambulate in a random pattern (for example, turning either to the right or turning to the left when facing a corner). An injured mouse was expected to ambulate in a consistent pattern (for example, consistently turn toward one direction, and not be readily coaxed in the opposite direction).

7.5. Posture and Head Tilt

The mouse was observed for its posture and head tilt. An uninjured mouse kept all limbs tucked beneath its body when still or ambulating. A brain injured mouse was expected to demonstrate weakness, dragging or abduction of contralateral limbs.

Varying degress of head tilt were present if the head was rotated within the coronal plane (a result of gait or impairment of posture).

7.6. Baton Test

The baton test was utilized to evaluate coordination and proprioception. Briefly, a mouse was suspended by the tail and allowed to grasp a fiber tippled applicator with all four paws. The applicator then was released while the mouse remained suspended.

The baton test was divided into two subcategories: (1) speed, and (2) accuracy. An uninjured mouse would grasp the applicator tightly with all four paws quickly and accurately, often attempting to climb onto it. An injured mouse was expected to grasp the applicator more slowly and less accurately, requiring several attempts until the paws closed in on the applicator. The injured mouse's grasp would be too weak to hold onto the applicator for a prolonged period.

The effect of JM-4 peptide therapy on neurologic deficits (SNAP scores) was evaluated 10 days post-injury by blinded observers.

Figure 7:
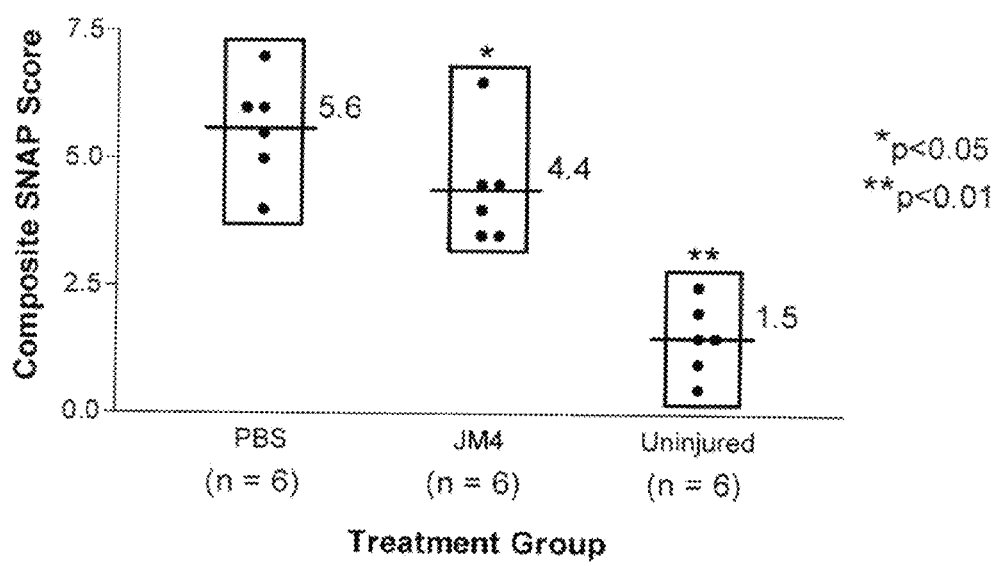
FIG. 7 shows a graph of composite SNAP score from the PBS treatment group (n=6), JM-4 peptide treatment group (n=6), and the uninjured group (n=6) ("*"=p<0.05; "**"=p<0.01).

FIG. 7 shows a graph of composite SNAP scores from the PBS treatment group (n=6), JM-4 peptide treatment group (n=6), and the uninjured group (n=6) ("*"=$p<0.05$; "**"=$p<0.01$).

JM-4 peptide treated TBI mice showed significant improvement in neurologic deficits compared to vehicle treated TBI mice on a 40 point scale (score 1.5 indicates normal exam). The findings reached significance in spite of the small numbers of animals in each experimental group. When evaluating animals by neurobehavioral paradigms, the inter-animal variation may be large and a sample group size of 12-15 may be required for most data to readily achieve significance.

Figure 8A:
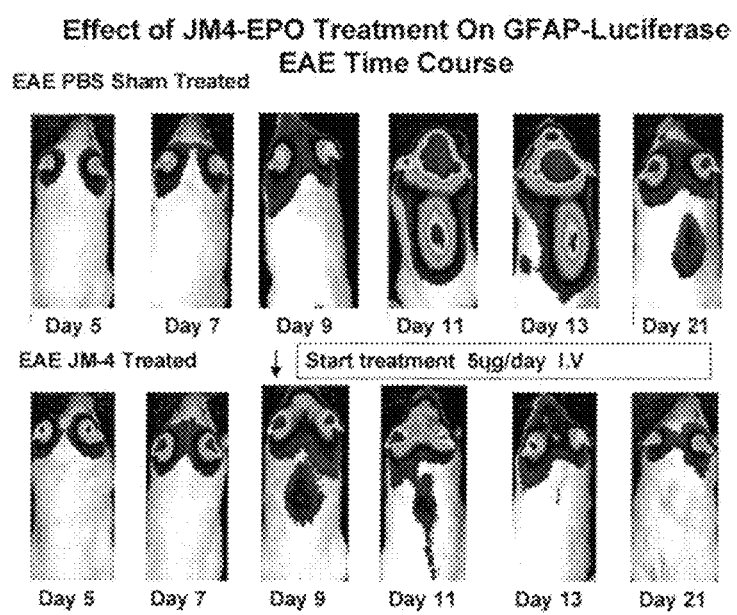
FIG. 8A shows CNS imaging in living animals generated from transgenic mice containing a GFAP-Luciferase construct that have undergone EAE induction.
Figure 8B:
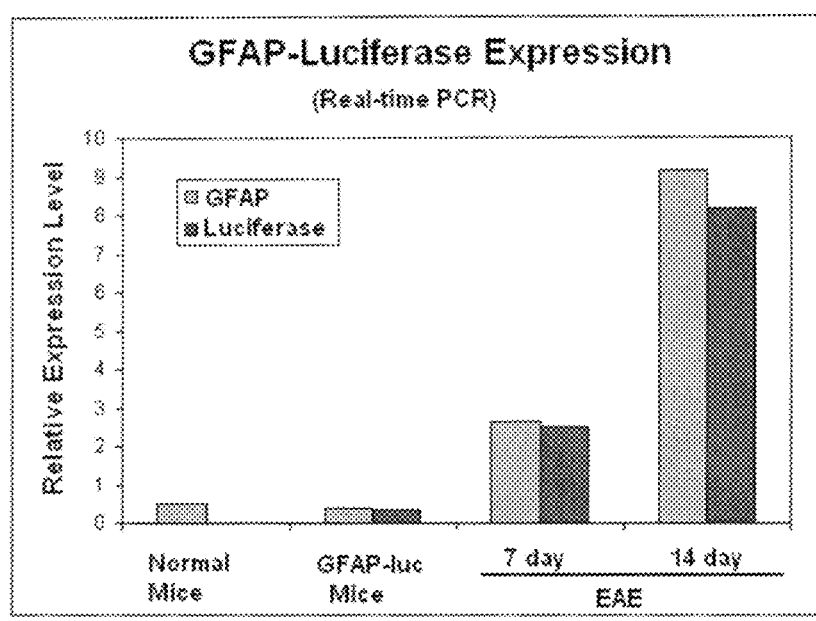
FIG. 8B shows a graph of relative expression level of GFAP-luciferase mRNA from 1) normal mice, 2) GFAP-luc mice, 3) 7-day EAE mice, and 4) 14-day EAE mice.

FIG. 8A shows CNS imaging in living animals generated from transgenic mice containing a GFAP-Luciferase construct that have undergone EAE induction. Following a CNS injury, the GFAP enhanced response of these animals has been linked to luciferase expression. By injecting luciferin, the time course of brain injury in EAE and its early resolution when treated with short EPO peptide JM-4 peptide can be chartered by bioluminescence and correlated with neurologic recovery. The bioluminescence can be determined and the relative neuroprotective effects of the therapeutic compound can be quantified. The increase from controls levels in GFAP expression also can be confirmed by quantifying GFAP-Luc message abundance using real-time PCR (as shown in FIG. 8B).

Example 8

Determination of Therapeutic Window for JM-4 Peptide

The therapeutic time window for achieving a beneficial effect with JM-4 peptide was determined. Briefly, the administration (i.p.) of JM-4 peptide to mice was initiated at different times post-TBI. Table 1 shows the amounts of active agent administered to each group of mice and the times of administration post-TBI.

TABLE 1

| Group (mice) | Active Agent | Amount per mouse | Time post-TBI | Subsequent treatment dose(s) |
|---|---|---|---|---|
| 1 | PBS | 200 µl | 15 minutes | 24 hours, 48 hours |
| 2 | JM-4 peptide | 10 µg | 15 minutes | 24 hours, 48 hours |
| 3 | JM-4 peptide | 10 µg | 3 hours | 24 hours, 48 hours |
| 4 | JM-4 peptide | 10 µg | 9 hours | 24 hours, 48 hours |
| 5 | JM-4 peptide | 10 µg | 24 hours | 48 hours |

Groups 2-4 received delayed initial JM-4 administration, and received subsequent treatment doses at 24 hours and 48 hours following injury; Group 5 received only one subsequent additional dose at 48 hours post-injury. Mice were sacrificed 3 days post-TBI. The effect of treatment delay was determined by TUNEL staining.

Figure 9:
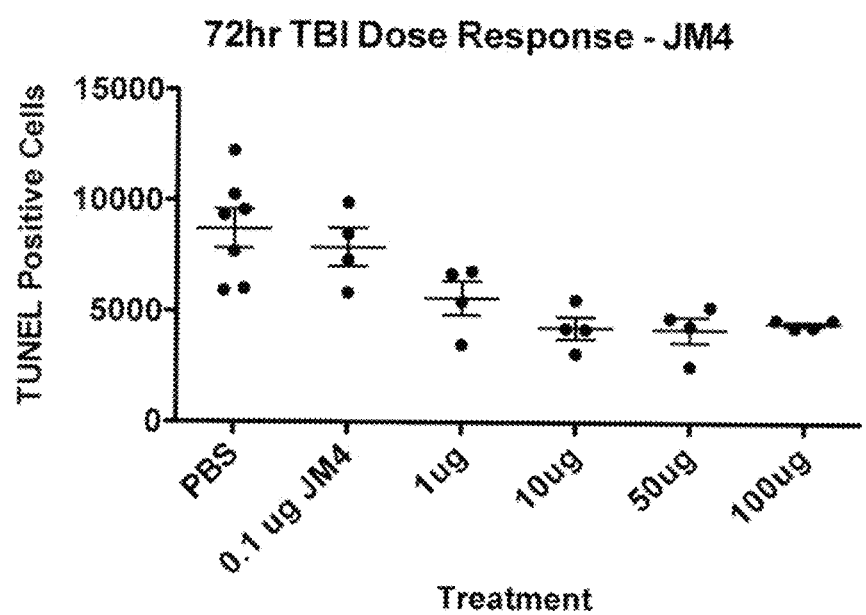
FIG. 9 is a dose response curve showing TUNEL positive cells in the injured brain hemisphere under sham treatment conditions (PBS), and five additional groups of brain injured animals that were treated intraperitoneally with JM-4.

FIG. 9 is a dose response curve showing the effect of treatment delay with JM-4 on number of TUNEL positive cells in the injured brain hemisphere under SHAM treatment conditions (PBS) and for four groups of brain injured animals treated intraperitoneally with JM-4 either at 0.1 microgram, 1 microgram, 10 microgram, 50 micrograms or 100 micrograms daily for 72 hours (n per group). The lowest two doses of JM-4 therapy (0.1 µg and 1 µg JM-4, respectively) failed to significantly block cell death as judged by TUNEL positivity. In contrast, 10 micrograms, 50 micrograms and 100 micrograms daily doses of JM-4 significant protected against cell death (p=0.005). There was, however, no additional protection provided by going to higher drug levels such as 50 or 100 micrograms daily.

Figure 10:
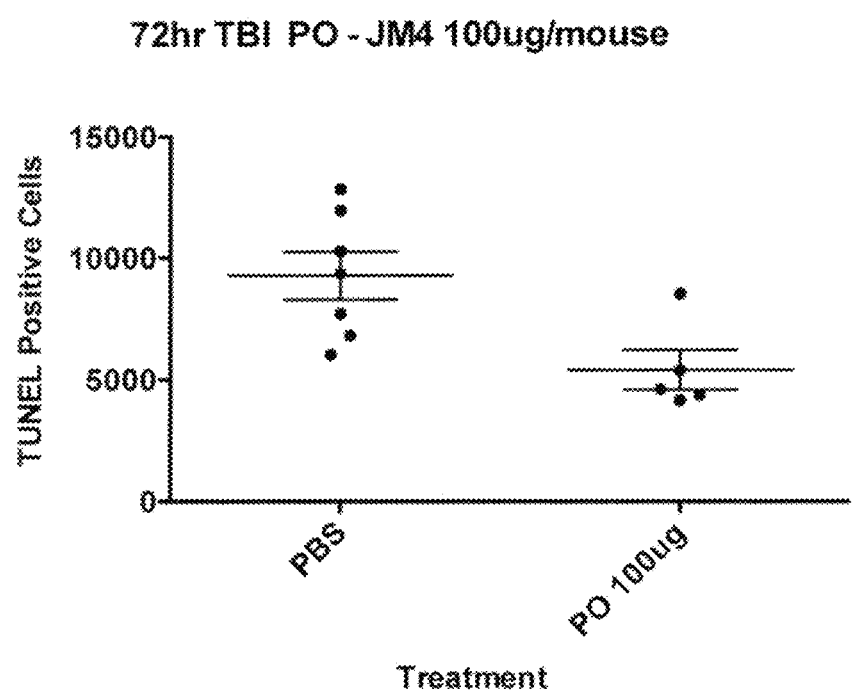
FIG. 10 is a plot of TUNEL-positive cells versus treatment, showing that JM-4 is effective when administered PO (orally) at a dose of 100 micrograms daily by gavage (force feeding) using a stomach tube when compared to sham treatment (phosphate-buffered saline) conditions (unpaired t test, p=0.01).

FIG. 10 shows that JM-4 is also effective blocking cell death when administered PO (orally) 3 hours after injury to mice at a dose of 100 micrograms daily by gavage using a stomach tube (unpaired t test, p=0.01)

Figure 11:
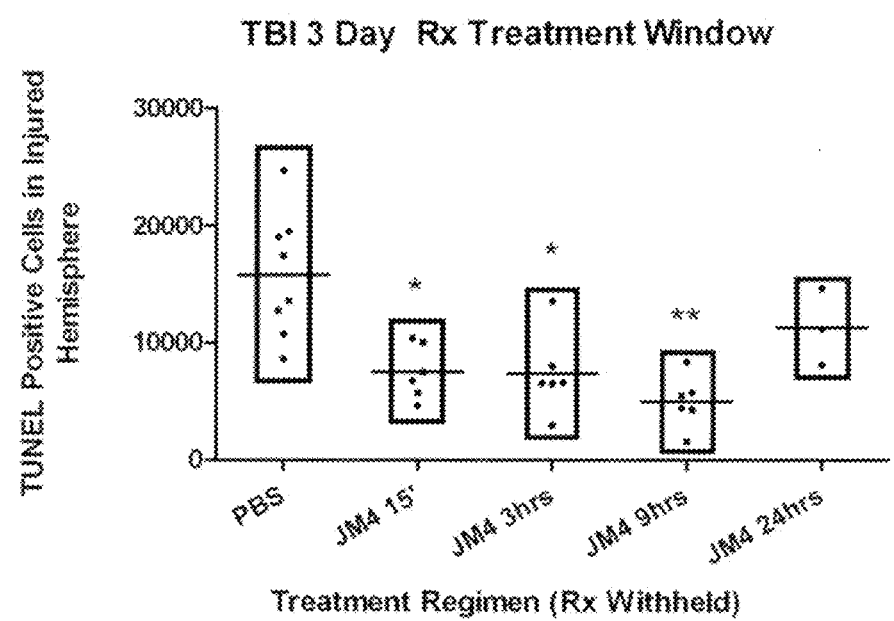
FIG. 11 is a plot of TUNEL-positive cells in injured hemispheres versus time interval after injury till treatment. This shows the duration of the treatment window following acute brain trauma.

FIG. 11 is a graph of TUNEL positive cells in injured hemisphere versus treatment regimen. Mice were treated with JM-4 at 15 minutes (n=6), 3 hours (n=6), 9 hours (n=6), and 24 hours (n=3) post-injury and results compared to sham treatment with PBS (n=8). It shows the duration of the treatment window following acute brain trauma. The largest number of dying cells is observed in the graph of TUNEL positive dying cells in the injured brain hemisphere from the PBS sham treatment group. The 15 minute post injury JM-4 peptide treatment group already shows a statistically significant neuroprotective effect as judged by the reduction in dying TUNEL positive cells, compared to the sham treated controls. Treatment with JM-4 peptide 3 and 9 hours post-injury was equally effective, indicating that the therapeutic window is at least 9 hours long following severe head trauma. Very little treatment effect was observed when treatment was delayed 24 hours.

While the described invention has been described with reference to the specific embodiments thereof it should be understood by those skilled in the art that various changes may be made and equivalents may be substituted without departing from the true spirit and scope of the invention. In addition, many modifications may be made to adopt a particular situation, material, composition of matter, process, process step or steps, to the objective spirit and scope of the described invention. All such modifications are intended to be within the scope of the claims appended hereto.

What is claimed is:

1. A method for treating an inflammatory brain disease or traumatic brain injury in a subject, the method comprising:
   (a) providing a pharmaceutical composition comprising:
      (i) a therapeutically effective amount of an erythropoietin (EPO)-derived oligopeptide of JM-4 (SEQ ID NO:1); and
      (ii) a pharmaceutically acceptable carrier;
   (b) administering the pharmaceutical composition of (a) to a subject in need thereof;
   wherein the composition is effective in treating or alleviating the inflammatory brain disease or traumatic brain injury, wherein inflammatory brain disease is a condition selected from the group consisting of multiple sclerosis, demyelinating disease, and chronic inflammatory brain disease.

2. The method according to claim 1, wherein the erythropoietin (EPO)-derived oligopeptide is a cyclic peptide.

3. The method according to claim 1, wherein the at least one isolated erythropoietin (EPO)-derived oligopeptide is a stabilized isolated erythropoietin (EPO)-derived oligopeptide, wherein the stabilized isolated erythropoietin (EPO)-derived oligopeptide comprises at least one small bicyclic compound added to either an N-terminal end or a C-terminal end of the isolated erythropoietin (EPO)-derived oligopeptide.

4. The method according to claim 1, wherein administering step (b) occurs within about 15 minutes after the traumatic brain injury.

5. The method according to claim 1, wherein administering step (b) occurs within about 1 hour after the traumatic brain injury.

6. The method according to claim 1, wherein administering step (b) occurs within about 3 hours after the traumatic brain injury.

7. The method according to claim 1, wherein administering step (b) occurs within about 6 hours after the traumatic brain injury.

8. The method according to claim 1, wherein administering step (b) occurs within 9 hours after the traumatic brain injury.

9. The method according to claim 1, wherein administering step (b) occurs within about 24 hours of the traumatic brain injury.

10. The method according to claim 1, wherein the method further comprises reducing infiltration of a population of a mononuclear cell into the brain of the subject.

11. The method according to claim 1, wherein the method further comprises reducing axonal damage in at least one region of the brain of the subject affected by the traumatic brain injury.

12. The method according to claim 1, further comprising maintaining a hematocrit at a stable level.

13. The method according to claim 1, further comprising maintaining a hematocrit within about 20% of a reference value or baseline level.

* * * * *

SEQUENCE LISTING

```
<160> NUMBER OF SEQ ID NOS: 31

<210> SEQ ID NO 1
<211> LENGTH: 19
<212> TYPE: PRT
<213> ORGANISM: unknown
<220> FEATURE:
<223> OTHER INFORMATION: mammal

<400> SEQUENCE: 1

Gly Cys Ala Glu His Cys Ser Leu Asn Glu Asn Ile Thr Val Pro Asp
1               5                   10                  15

Thr Lys Val

<210> SEQ ID NO 2
<211> LENGTH: 25
<212> TYPE: PRT
<213> ORGANISM: unknown
<220> FEATURE:
<223> OTHER INFORMATION: mammal

<400> SEQUENCE: 2

Gln Gln Ala Val Glu Val Trp Gln Gly Leu Ala Leu Leu Ser Glu Ala
1               5                   10                  15

Val Leu Arg Gly Gln Ala Leu Leu Val
            20                  25

<210> SEQ ID NO 3
<211> LENGTH: 20
<212> TYPE: PRT
<213> ORGANISM: unknown
```

```
<220> FEATURE:
<223> OTHER INFORMATION: mammal

<400> SEQUENCE: 3

Thr Thr Gly Cys Ala Glu His Cys Ser Leu Asn Glu Asn Ile Thr Val
1               5                   10                  15

Pro Asp Thr Lys
            20

<210> SEQ ID NO 4
<211> LENGTH: 25
<212> TYPE: PRT
<213> ORGANISM: unknown
<220> FEATURE:
<223> OTHER INFORMATION: mammal

<400> SEQUENCE: 4

Ala Glu His Cys Ser Leu Asn Glu Asn Ile Thr Val Pro Asp Thr Lys
1               5                   10                  15

Val Asn Phe Tyr Ala Trp Arg Met Glu
            20                  25

<210> SEQ ID NO 5
<211> LENGTH: 18
<212> TYPE: PRT
<213> ORGANISM: unknown
<220> FEATURE:
<223> OTHER INFORMATION: mammal

<400> SEQUENCE: 5

Cys Ala Glu His Cys Ser Leu Asn Glu Asn Ile Thr Val Pro Asp Thr
1               5                   10                  15

Lys Val

<210> SEQ ID NO 6
<211> LENGTH: 17
<212> TYPE: PRT
<213> ORGANISM: unknown
<220> FEATURE:
<223> OTHER INFORMATION: mammal
<220> FEATURE:
<221> NAME/KEY: MISC_FEATURE
<222> LOCATION: (1)..(1)
<223> OTHER INFORMATION: wherein Ala is covalently linked to d-biotin

<400> SEQUENCE: 6

Ala Glu His Cys Ser Leu Asn Glu Asn Ile Thr Val Pro Asp Thr Lys
1               5                   10                  15

Val

<210> SEQ ID NO 7
<211> LENGTH: 6
<212> TYPE: PRT
<213> ORGANISM: unknown
<220> FEATURE:
<223> OTHER INFORMATION: mammal

<400> SEQUENCE: 7

Cys Ala Glu His Cys Ser
1               5

<210> SEQ ID NO 8
<211> LENGTH: 8
<212> TYPE: PRT
<213> ORGANISM: unknown
```

```
<220> FEATURE:
<223> OTHER INFORMATION: mammal

<400> SEQUENCE: 8

Gly Cys Ala Glu His Cys Ser Leu
1               5

<210> SEQ ID NO 9
<211> LENGTH: 14
<212> TYPE: PRT
<213> ORGANISM: unknown
<220> FEATURE:
<223> OTHER INFORMATION: mammal

<400> SEQUENCE: 9

Cys Ala Glu His Cys Ser Leu Asn Glu Asn Ile Thr Val Pro
1               5                   10

<210> SEQ ID NO 10
<211> LENGTH: 21
<212> TYPE: PRT
<213> ORGANISM: unknown
<220> FEATURE:
<223> OTHER INFORMATION: mammal

<400> SEQUENCE: 10

Thr Thr Gly Cys Ala Glu His Cys Ser Leu Asn Glu Asn Ile Thr Val
1               5                   10                  15

Pro Asp Thr Lys Val
            20

<210> SEQ ID NO 11
<211> LENGTH: 17
<212> TYPE: PRT
<213> ORGANISM: unknown
<220> FEATURE:
<223> OTHER INFORMATION: mammal

<400> SEQUENCE: 11

Thr Thr Gly Cys Ala Glu His Cys Ser Leu Asn Glu Asn Ile Thr Val
1               5                   10                  15

Pro

<210> SEQ ID NO 12
<211> LENGTH: 13
<212> TYPE: PRT
<213> ORGANISM: unknown
<220> FEATURE:
<223> OTHER INFORMATION: mammal

<400> SEQUENCE: 12

Ser Leu Asn Glu Asn Ile Thr Val Pro Asp Thr Lys Val
1               5                   10

<210> SEQ ID NO 13
<211> LENGTH: 20
<212> TYPE: PRT
<213> ORGANISM: unknown
<220> FEATURE:
<223> OTHER INFORMATION: mammal

<400> SEQUENCE: 13

Cys Ala Glu His Cys Ser Leu Asn Lys Asn Ile Asn Leu Asp Ser Val
1               5                   10                  15

Asp Gly Val Pro
```

20

<210> SEQ ID NO 14
<211> LENGTH: 18
<212> TYPE: PRT
<213> ORGANISM: unknown
<220> FEATURE:
<223> OTHER INFORMATION: mammal

<400> SEQUENCE: 14

Gly Cys Ala Glu His Cys Ser Leu Met Glu Asn Asn Leu Arg Arg Pro
1               5                   10                  15

Asn Leu

<210> SEQ ID NO 15
<211> LENGTH: 17
<212> TYPE: PRT
<213> ORGANISM: unknown
<220> FEATURE:
<223> OTHER INFORMATION: mammal

<400> SEQUENCE: 15

Ala Glu His Cys Ser Leu Asn Glu Asn Ile Thr Val Pro Asp Thr Lys
1               5                   10                  15

Val

<210> SEQ ID NO 16
<211> LENGTH: 20
<212> TYPE: PRT
<213> ORGANISM: unknown
<220> FEATURE:
<223> OTHER INFORMATION: mammal

<400> SEQUENCE: 16

Tyr Val Lys His Gln Gly Leu Asn Lys Asn Ile Asn Leu Asp Ser Val
1               5                   10                  15

Asp Gly Val Pro
            20

<210> SEQ ID NO 17
<211> LENGTH: 11
<212> TYPE: PRT
<213> ORGANISM: unknown
<220> FEATURE:
<223> OTHER INFORMATION: mammal

<400> SEQUENCE: 17

Leu Met Glu Asn Asn Leu Arg Arg Pro Asn Leu
1               5                   10

<210> SEQ ID NO 18
<211> LENGTH: 16
<212> TYPE: PRT
<213> ORGANISM: unknown
<220> FEATURE:
<223> OTHER INFORMATION: mammal

<400> SEQUENCE: 18

Ala Glu His Cys Ser Leu Met Glu Asn Asn Leu Arg Arg Pro Asn Leu
1               5                   10                  15

<210> SEQ ID NO 19
<211> LENGTH: 193
<212> TYPE: PRT
<213> ORGANISM: Homo sapiens

<400> SEQUENCE: 19

Met Gly Val His Glu Cys Pro Ala Trp Leu Trp Leu Leu Leu Ser Leu
1               5                   10                  15

Leu Ser Leu Pro Leu Gly Leu Pro Val Leu Gly Ala Pro Pro Arg Leu
            20                  25                  30

Ile Cys Asp Ser Arg Val Leu Glu Arg Tyr Leu Leu Glu Ala Lys Glu
        35                  40                  45

Ala Glu Asn Ile Thr Thr Gly Cys Ala Glu His Cys Ser Leu Asn Glu
    50                  55                  60

Asn Ile Thr Val Pro Asp Thr Lys Val Asn Phe Tyr Ala Trp Lys Arg
65                  70                  75                  80

Met Glu Val Gly Gln Gln Ala Val Glu Val Trp Gln Gly Leu Ala Leu
                85                  90                  95

Leu Ser Glu Ala Val Leu Arg Gly Gln Ala Leu Leu Val Asn Ser Ser
            100                 105                 110

Gln Pro Trp Glu Pro Leu Gln Leu His Val Asp Lys Ala Val Ser Gly
        115                 120                 125

Leu Arg Ser Leu Thr Thr Leu Leu Arg Ala Leu Gly Ala Gln Lys Glu
    130                 135                 140

Ala Ile Ser Pro Pro Asp Ala Ala Ser Ala Ala Pro Leu Arg Thr Ile
145                 150                 155                 160

Thr Ala Asp Thr Phe Arg Lys Leu Phe Arg Val Tyr Ser Asn Phe Leu
                165                 170                 175

Arg Gly Lys Leu Lys Leu Tyr Thr Gly Glu Ala Cys Arg Thr Gly Asp
            180                 185                 190

Arg

<210> SEQ ID NO 20
<211> LENGTH: 27
<212> TYPE: PRT
<213> ORGANISM: Homo sapiens

<400> SEQUENCE: 20

Met Gly Val His Glu Cys Pro Ala Trp Leu Trp Leu Leu Leu Ser Leu
1               5                   10                  15

Leu Ser Leu Pro Leu Gly Leu Pro Val Leu Gly
            20                  25

<210> SEQ ID NO 21
<211> LENGTH: 166
<212> TYPE: PRT
<213> ORGANISM: Homo sapiens

<400> SEQUENCE: 21

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asp Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp

```
                    85                  90                  95
Lys Ala Val Ser Gly Leu Arg Ser Leu Thr Thr Leu Leu Arg Ala Leu
                100                 105                 110

Gly Ala Gln Lys Glu Ala Ile Ser Pro Pro Asp Ala Ala Ser Ala Ala
            115                 120                 125

Pro Leu Arg Thr Ile Thr Ala Asp Thr Phe Arg Lys Leu Phe Arg Val
        130                 135                 140

Tyr Ser Asn Phe Leu Arg Gly Lys Leu Lys Leu Tyr Thr Gly Glu Ala
145                 150                 155                 160

Cys Arg Thr Gly Asp Arg
                165

<210> SEQ ID NO 22
<211> LENGTH: 165
<212> TYPE: PRT
<213> ORGANISM: Homo sapiens

<400> SEQUENCE: 22

Ala Pro Pro Arg Leu Ile Cys Asp Ser Arg Val Leu Glu Arg Tyr Leu
1               5                   10                  15

Leu Glu Ala Lys Glu Ala Glu Asn Ile Thr Thr Gly Cys Ala Glu His
            20                  25                  30

Cys Ser Leu Asn Glu Asn Ile Thr Val Pro Asn Thr Lys Val Asn Phe
        35                  40                  45

Tyr Ala Trp Lys Arg Met Glu Val Gly Gln Gln Ala Val Glu Val Trp
    50                  55                  60

Gln Gly Leu Ala Leu Leu Ser Glu Ala Val Leu Arg Gly Gln Ala Leu
65                  70                  75                  80

Leu Val Asn Ser Ser Gln Pro Trp Glu Pro Leu Gln Leu His Val Asp
                85                  90                  95

Leu Ala Val Ser Gly Leu Arg Ser Leu Thr Thr Leu Leu Arg Ala Leu
                100                 105                 110

Gly Ala Gln Leu Glu Ala Ile Ser Pro Pro Asp Ala Ala Ser Ala Ala
            115                 120                 125

Pro Leu Arg Thr Ile Thr Ala Asn Thr Phe Arg Lys Leu Phe Arg Val
        130                 135                 140

Tyr Ser Asn Arg Leu Arg Gly Lys Leu Lys Leu Tyr Thr Gln Glu Ala
145                 150                 155                 160

Cys Arg Thr Gly Asp
                165

<210> SEQ ID NO 23
<211> LENGTH: 19
<212> TYPE: PRT
<213> ORGANISM: unknown
<220> FEATURE:
<223> OTHER INFORMATION: mammal
<220> FEATURE:
<221> NAME/KEY: MISC_FEATURE
<222> LOCATION: (1)..(1)
<223> OTHER INFORMATION: wherein Gly is covalently linked to d-biotin

<400> SEQUENCE: 23

Gly Cys Ala Glu His Cys Ser Leu Asn Glu Asn Ile Thr Val Pro Asp
1               5                   10                  15

Thr Lys Val

<210> SEQ ID NO 24
```

```
<211> LENGTH: 13
<212> TYPE: PRT
<213> ORGANISM: unknown
<220> FEATURE:
<223> OTHER INFORMATION: mammal
<220> FEATURE:
<221> NAME/KEY: MISC_FEATURE
<222> LOCATION: (1)..(1)
<223> OTHER INFORMATION: wherein Ala is covalently linked to d-biotin

<400> SEQUENCE: 24

Ala Glu His Cys Ser Leu Asn Glu Asn Ile Thr Val Pro
1               5                   10

<210> SEQ ID NO 25
<211> LENGTH: 17
<212> TYPE: PRT
<213> ORGANISM: unknown
<220> FEATURE:
<223> OTHER INFORMATION: mammal
<220> FEATURE:
<221> NAME/KEY: MISC_FEATURE
<222> LOCATION: (17)..(17)
<223> OTHER INFORMATION: wherein Val is covalently linked to biotin

<400> SEQUENCE: 25

Ala Glu His Cys Ser Leu Asn Glu Asn Ile Thr Val Pro Asp Thr Lys
1               5                   10                  15

Val

<210> SEQ ID NO 26
<211> LENGTH: 20
<212> TYPE: PRT
<213> ORGANISM: unknown
<220> FEATURE:
<223> OTHER INFORMATION: mammal
<220> FEATURE:
<221> NAME/KEY: MISC_FEATURE
<222> LOCATION: (20)..(20)
<223> OTHER INFORMATION: wherein Pro is covalently linked to biotin

<400> SEQUENCE: 26

Tyr Val Lys His Gln Gly Leu Asn Lys Asn Ile Asn Leu Asp Ser Val
1               5                   10                  15

Asp Gly Val Pro
            20

<210> SEQ ID NO 27
<211> LENGTH: 18
<212> TYPE: PRT
<213> ORGANISM: unknown
<220> FEATURE:
<223> OTHER INFORMATION: mammal

<400> SEQUENCE: 27

Gly Cys Ala Glu His Cys Ser Leu Met Glu Asn Asn Leu Arg Arg Pro
1               5                   10                  15

Asn Leu

<210> SEQ ID NO 28
<211> LENGTH: 12
<212> TYPE: PRT
<213> ORGANISM: unknown
<220> FEATURE:
<223> OTHER INFORMATION: mammal
<220> FEATURE:
<221> NAME/KEY: MISC_FEATURE
<222> LOCATION: (1)..(1)
```

```
-continued

<223> OTHER INFORMATION: wherein Ile is covalently linked to d-biotin

<400> SEQUENCE: 28

Ile Leu Met Glu Asn Asn Leu Arg Arg Pro Asn Leu
1               5                   10

<210> SEQ ID NO 29
<211> LENGTH: 16
<212> TYPE: PRT
<213> ORGANISM: unknown
<220> FEATURE:
<223> OTHER INFORMATION: mammal
<220> FEATURE:
<221> NAME/KEY: MISC_FEATURE
<222> LOCATION: (1)..(1)
<223> OTHER INFORMATION: wherein Ala is covalently linked to d-biotin

<400> SEQUENCE: 29

Ala Glu His Cys Ser Leu Met Glu Asn Asn Leu Arg Arg Pro Asn Leu
1               5                   10                  15

<210> SEQ ID NO 30
<211> LENGTH: 13
<212> TYPE: PRT
<213> ORGANISM: unknown
<220> FEATURE:
<223> OTHER INFORMATION: mammal
<220> FEATURE:
<221> NAME/KEY: MISC_FEATURE
<222> LOCATION: (13)..(13)
<223> OTHER INFORMATION: wherein Pro is covalently linked to d-biotin

<400> SEQUENCE: 30

Ala Glu His Cys Ser Leu Asn Glu Asn Ile Thr Val Pro
1               5                   10

<210> SEQ ID NO 31
<211> LENGTH: 4
<212> TYPE: PRT
<213> ORGANISM: unknown
<220> FEATURE:
<223> OTHER INFORMATION: mammal

<400> SEQUENCE: 31

Thr Gly Asp Arg
1
```